US007240882B2

(12) United States Patent
Degentesh et al.

(10) Patent No.: US 7,240,882 B2
(45) Date of Patent: Jul. 10, 2007

(54) MEDICAL CONTAINER LOADING SYSTEM AND METHOD FOR USE WITH FLUID CONTAINERS, SYRINGES AND MEDICAL INJECTORS

(75) Inventors: Drew Degentesh, Pittsburgh, PA (US); Matthew Beale, Pittsburgh, PA (US); John Crowley, Pittsburgh, PA (US); Matthew Goodworth, Pittsburgh, PA (US); David M. Reilly, Glenshaw, PA (US); Frederick W. Trombley, III, Gibsonia, PA (US); Mark Trocki, Cheswick, PA (US)

(73) Assignee: Medrad, Inc., Indianola, PA (US)

( * ) Notice: Subject to any disclaimer, the term of this patent is extended or adjusted under 35 U.S.C. 154(b) by 455 days.

(21) Appl. No.: 10/718,260

(22) Filed: Nov. 20, 2003

(65) Prior Publication Data

US 2004/0210192 A1  Oct. 21, 2004

Related U.S. Application Data

(60) Provisional application No. 60/429,056, filed on Nov. 25, 2002.

(51) Int. Cl.
*A47F 5/08* (2006.01)
(52) U.S. Cl. ............................ 248/231.91; 248/309.1; 604/151
(58) Field of Classification Search ............... 604/151; 248/231.9, 309.1, 310, 311.3, 312, 314
See application file for complete search history.

(56) References Cited

U.S. PATENT DOCUMENTS

| 2,463,113 A | 3/1949 | Klein |
| 2,821,193 A | 1/1958 | Ziherl et al. |
| 3,517,668 A | 6/1970 | Brickson |
| 3,872,868 A * | 3/1975 | Kline .......................... 604/403 |
| 4,006,736 A | 2/1977 | Kranys et al. |

(Continued)

FOREIGN PATENT DOCUMENTS

EP  0584531  3/1994

(Continued)

OTHER PUBLICATIONS

Medrad MCT & MCT Plus Front Load Injector Operation Manual (1993), pp. 1-1 to 1-3, 2-1, 4-22 and 6-1 to 6-11.

(Continued)

*Primary Examiner*—Ramon O Ramirez
(74) *Attorney, Agent, or Firm*—Gregory Bradley; Jill Denesvich

(57) ABSTRACT

A medical container loading system includes a medical container loading device and a fill station. The fill station is located proximate to the medical container loading device and includes a mounting plate and a holding assembly. The holding assembly is connected to the mounting plate for supporting a medical fluid container adapted for fluid communication with a medical container, such as a syringe, used in the medical container loading device. The holding assembly may include a fixed support and a movable support, which maintain the medical fluid container in the holding assembly. The fixed support may be funnel-shaped with a smooth or stepped inner wall. The fixed support may also be rectangular shaped and have an inclined inner wall or support for supporting the body of the medical fluid container. The movable support may be a resiliently biased support arm or an adjustable strap.

35 Claims, 38 Drawing Sheets

U.S. PATENT DOCUMENTS

| | | | |
|---|---|---|---|
| 4,465,474 A | | 8/1984 | Mardorf et al. |
| 4,472,141 A | | 9/1984 | Dragan |
| 4,677,980 A | | 7/1987 | Reilly et al. |
| 4,681,566 A | | 7/1987 | Fenton, Jr. et al. |
| 4,696,447 A | * | 9/1987 | Strecker ................. 248/206.3 |
| 4,838,857 A | | 6/1989 | Strowe et al. |
| 4,880,192 A | * | 11/1989 | Vom Braucke et al. ..... 248/110 |
| 4,957,260 A | * | 9/1990 | Shelley ................... 248/311.3 |
| 4,969,447 A | * | 11/1990 | Di Nunzio et al. ......... 123/645 |
| 5,322,511 A | | 6/1994 | Armbruster et al. |
| 5,383,858 A | | 1/1995 | Reilly et al. |
| 5,507,727 A | | 4/1996 | Crainich |
| 5,520,653 A | | 5/1996 | Reilly et al. |
| 5,830,194 A | | 11/1998 | Anwar et al. |
| 5,927,351 A | * | 7/1999 | Zhu et al. ................... 141/330 |
| 6,048,334 A | | 4/2000 | Hirschman et al. |
| 6,068,164 A | | 5/2000 | Totaro |
| 6,090,064 A | | 7/2000 | Reilly et al. |
| 6,306,117 B1 | * | 10/2001 | Uber, III .................... 604/151 |
| 6,569,127 B1 | | 5/2003 | Fago et al. |
| 7,025,757 B2 | | 4/2006 | Reilly et al. |
| 2001/0047153 A1 | | 11/2001 | Trocki et al. |
| 2002/0107481 A1 | | 8/2002 | Reilly et al. |
| 2003/0045789 A1 | | 3/2003 | Thompson et al. |

FOREIGN PATENT DOCUMENTS

| | | |
|---|---|---|
| WO | WO 01/08727 | 2/2001 |
| WO | WO 02/070049 | 9/2002 |

OTHER PUBLICATIONS

EFD Syringe Filling Stations, web pages, www.efd-inc.com, EFD, Inc., East Providence, RI 02914 (1998-2002).

I & J Fisnar Automatic Barrell Loaders, web pages, www.ijfisnar.com, no date.

Oxford Compounding Products, web pages, www.nutrinox.com, Oxford Nutrition, no date.

* cited by examiner

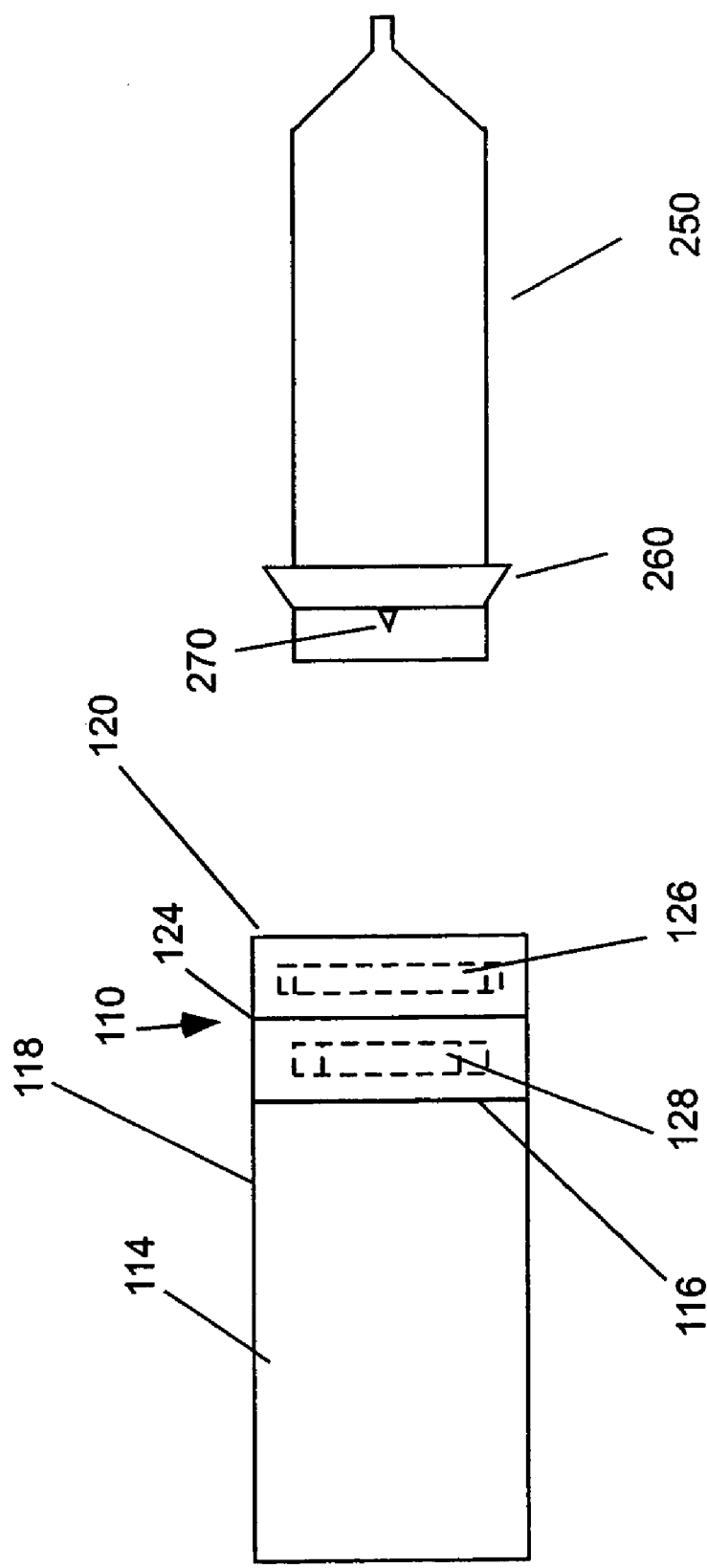

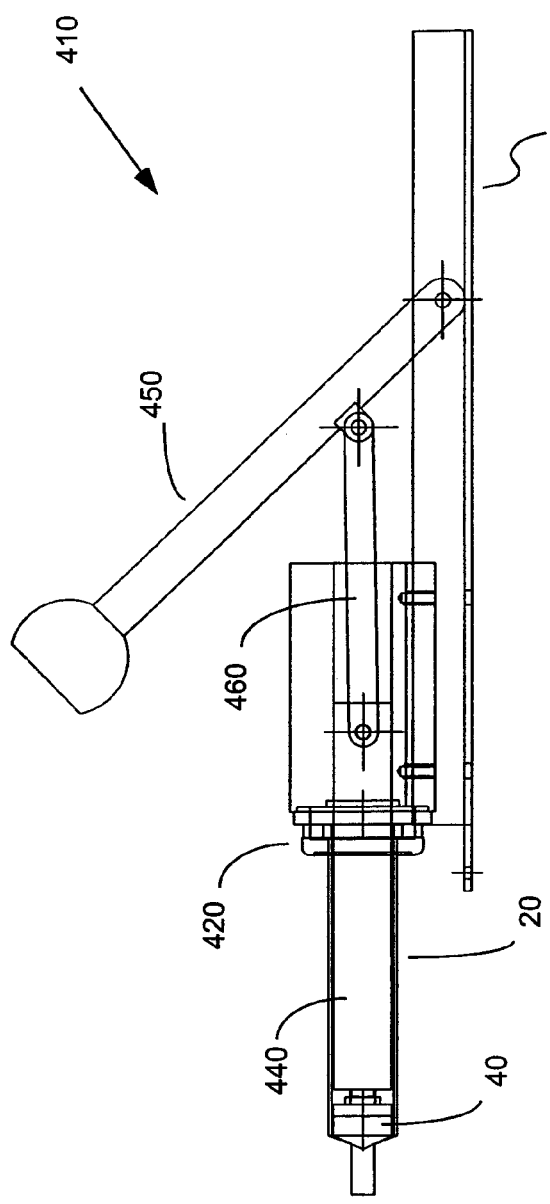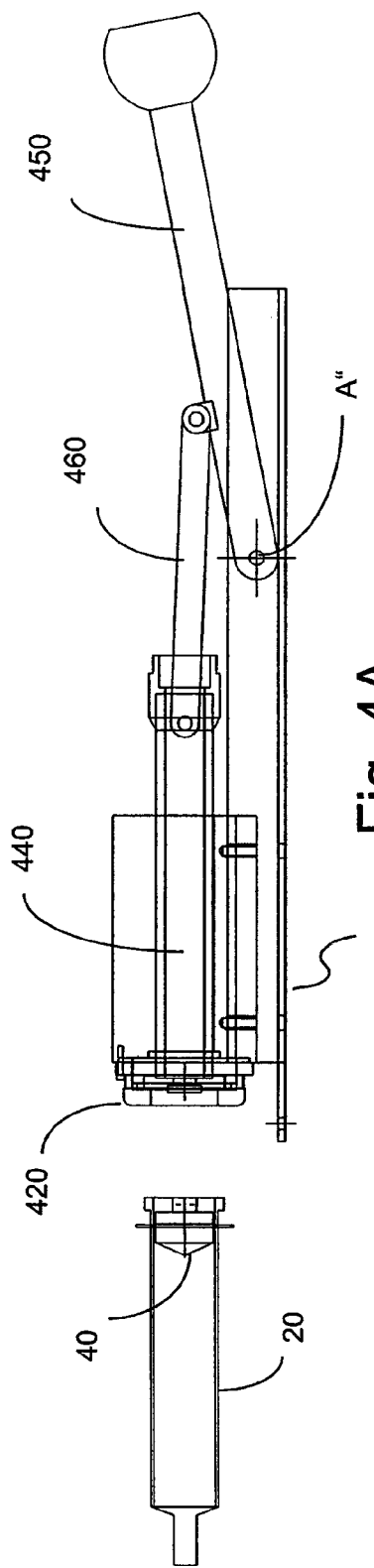
Fig. 4B
Fig. 4A

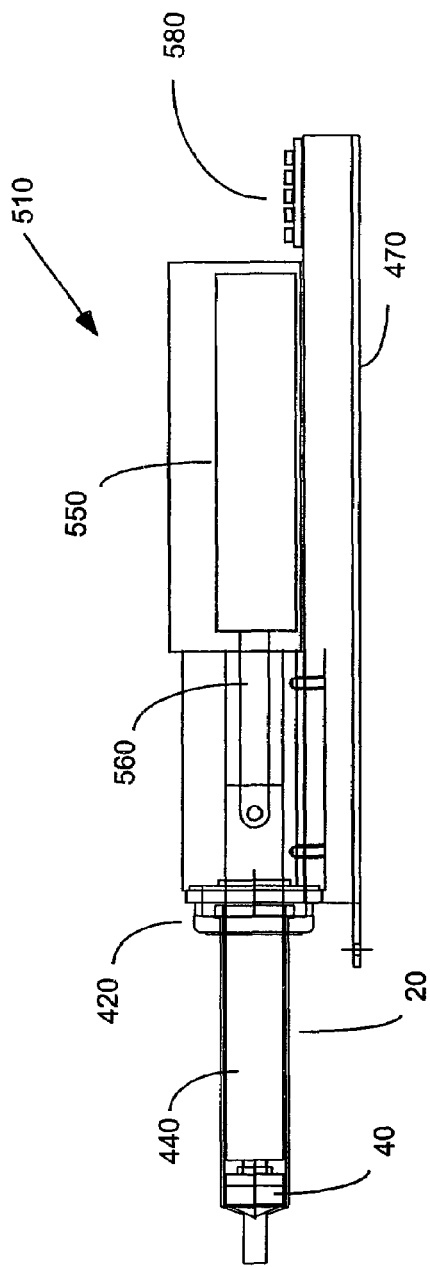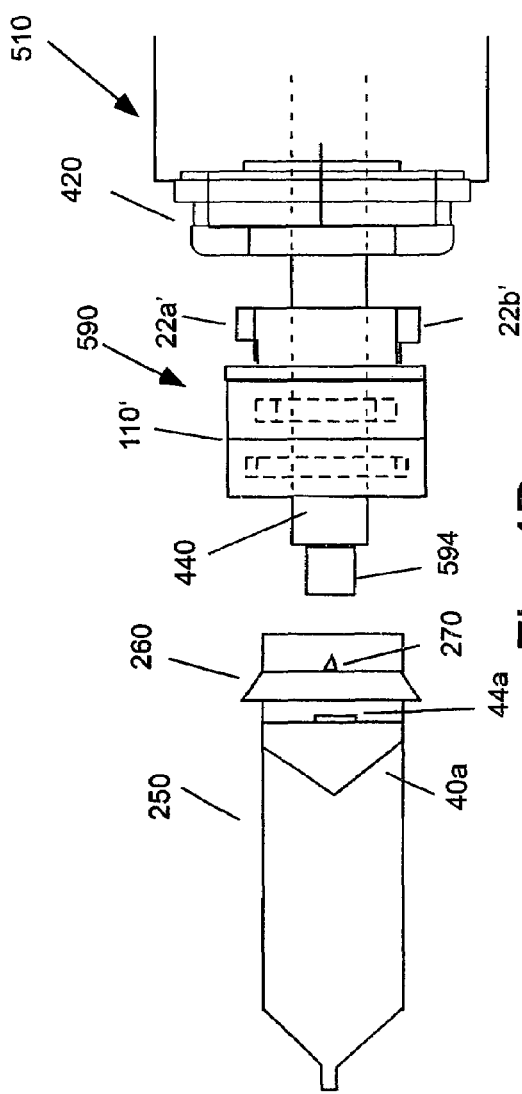

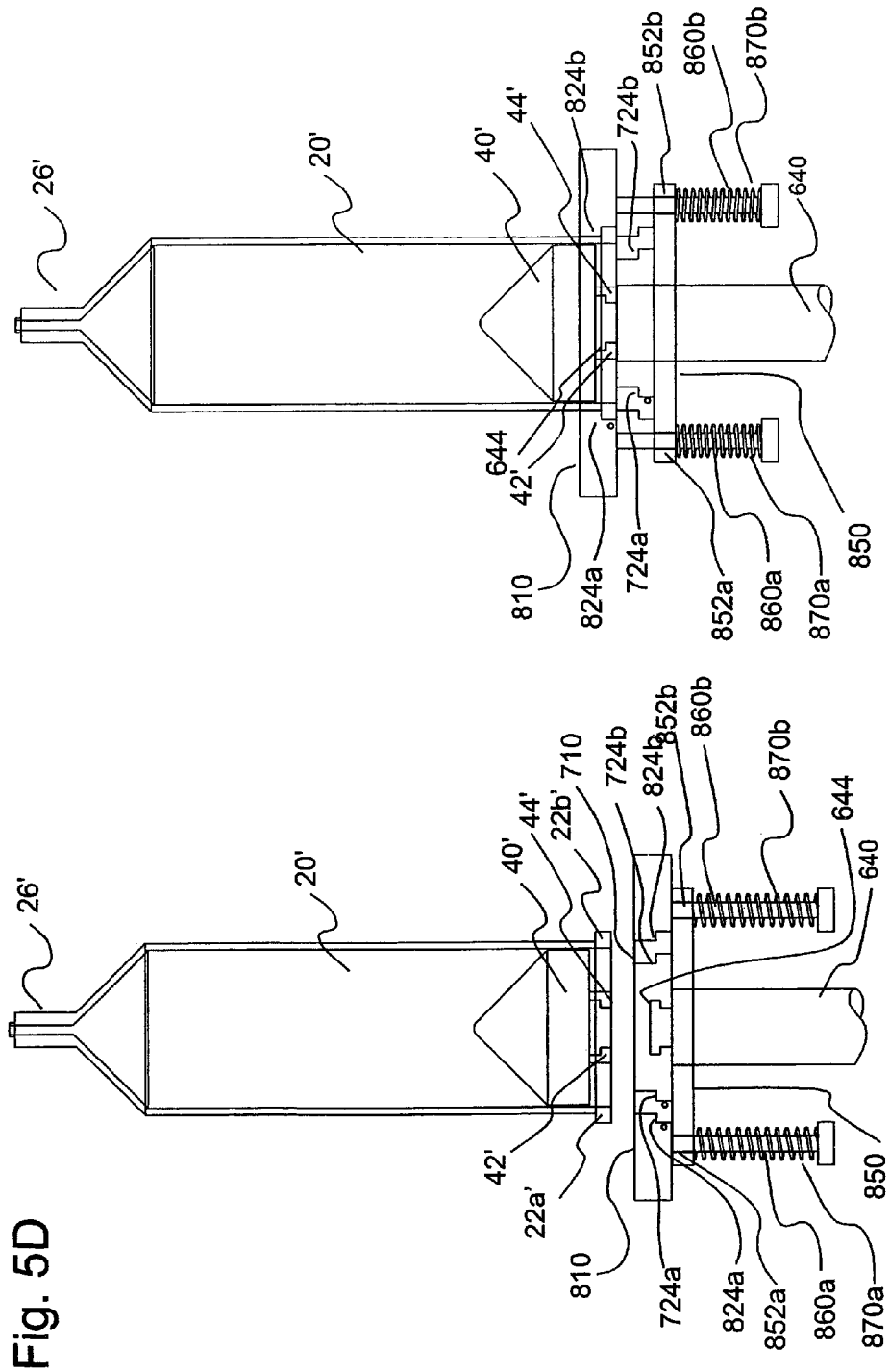

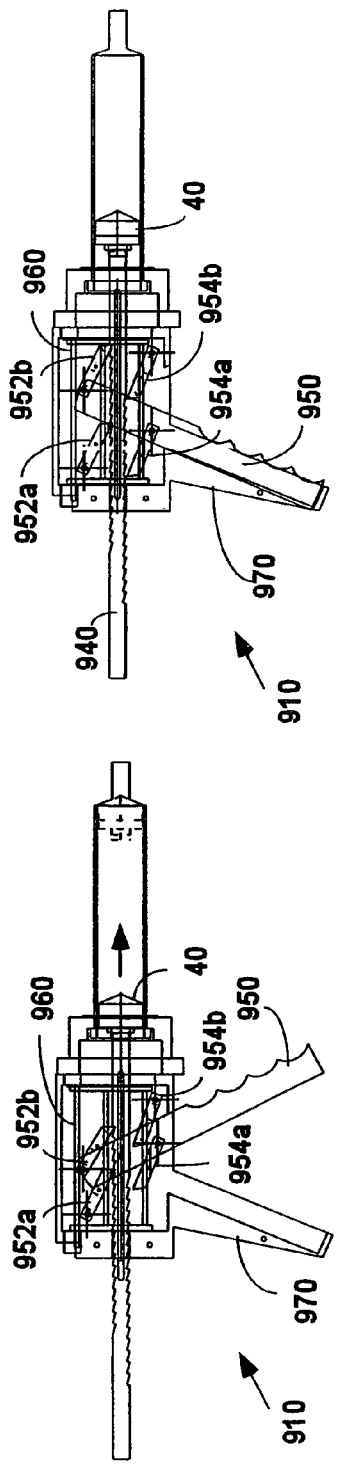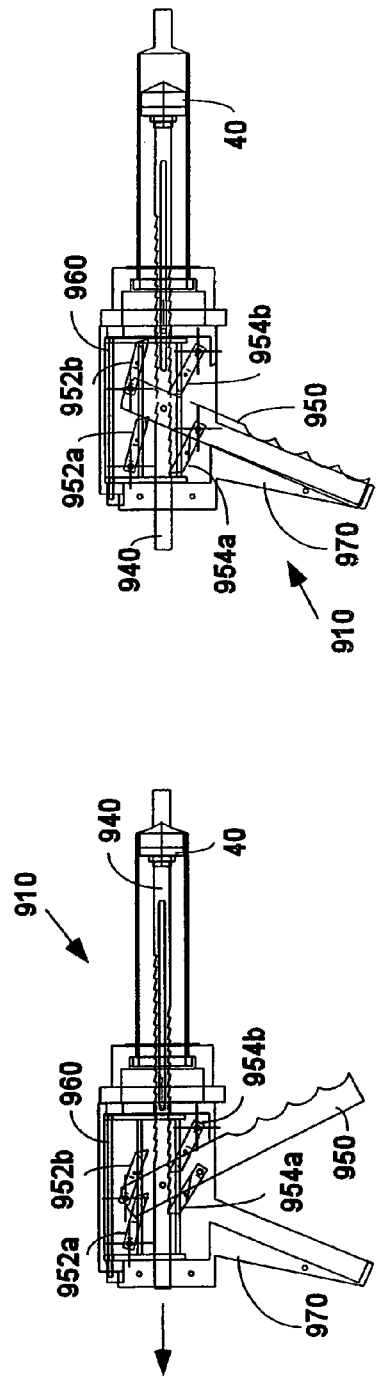
Fig. 6B

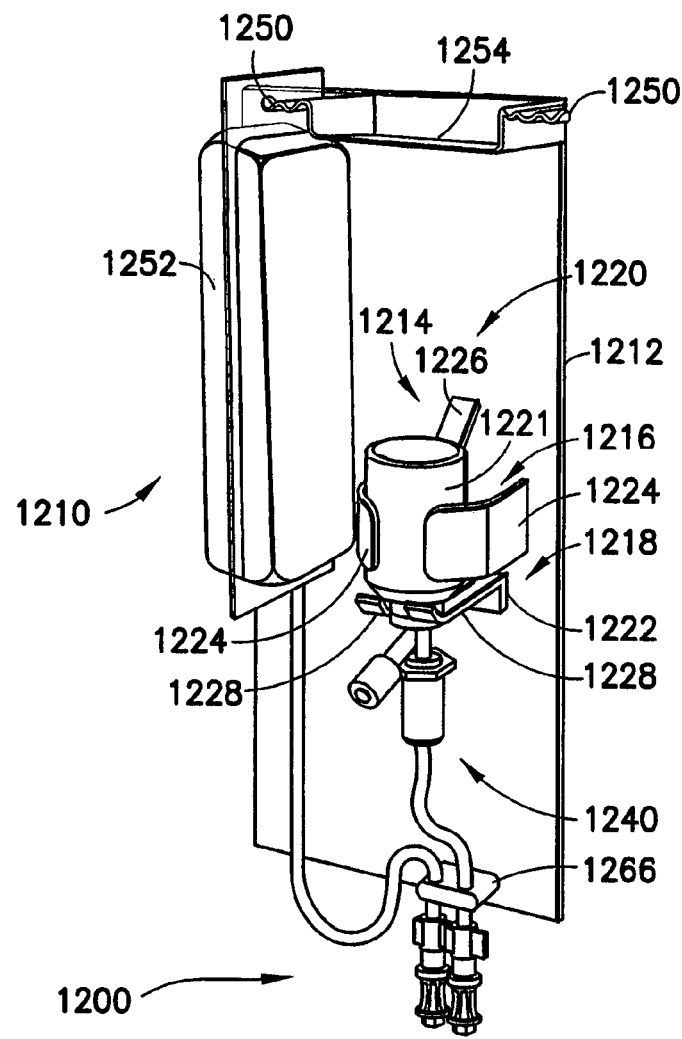
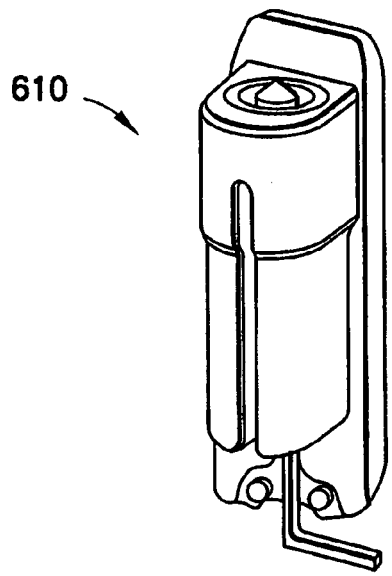
FIG.8

MEDICAL CONTAINER LOADING SYSTEM AND METHOD FOR USE WITH FLUID CONTAINERS, SYRINGES AND MEDICAL INJECTORS

CROSS REFERENCE TO RELATED APPLICATION

This application claims the benefit of Provisional Application Ser. No. 60/429,056, filed on Nov. 25, 2002, the contents of which are incorporated herein by reference.

RELATED APPLICATION

This application contains subject matter that is related to U.S. patent application Publication No. 2002-0107481, filed on Feb. 4, 2002, the contents of which are incorporated herein by reference.

BACKGROUND OF THE INVENTION

The present invention relates to medical container filling or loading systems and devices and, more particularly, to syringe loading systems and devices for use with medical and fluid containers, hand-held syringes, syringes for use with powered medical injectors or injector systems, and to medical injector systems including such syringes and syringe loading systems and devices. Additionally, the present invention relates to medical container filling systems and devices and to syringe loading systems incorporating fill stations and devices for use with syringes and medical injectors.

A number of injector-actuated syringes and powered injectors for use in medical procedures such as angiography, computed tomography, ultrasound and magnetic resonance imaging (MRI) have been developed. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

The front-loading injector of U.S. Pat. No. 5,383,858 includes a releasable mounting mechanism for securing the syringe to the front wall of the injector. Other types of releasable mounting mechanisms for front-loading syringes are disclosed in U.S. patent application Publication No. 2001-0047153, assigned to the assignee of the present invention, the disclosure of which is incorporated herein by reference.

The use of specifically designed mounting mechanisms generally limits the use of syringes of other various types with front-loading injectors. Syringe adapters attachable to those front-loading injectors are sometimes used to allow the use of such syringes with the front-loading injectors. For example, U.S. Pat. No. 5,520,653 discloses several adapters designed to allow the use of various syringes with a front-loading injector. Other adapters for front-loading injectors are disclosed, for example, in PCT Publication No. WO 01/08727 and U.S. patent application Ser. No. 09/633,299, filed on Aug. 8, 2000, each assigned to the assignee of the present invention, the disclosures of which are incorporated herein by reference.

Syringes are typically purchased either in a "prefilled" state, containing injection fluid supplied by the manufacturer, or in an empty, "fillable" state. Under current practice, empty syringes are typically attached to or loaded onto the power injector (either directly or via an adapter as known in the art) and connected to a source of injection fluid via, for example, tubing. The drive member of the powered injector is then reversed to draw the syringe plunger rearward within the syringe, thereby drawing injection fluid into the syringe for later injection into a patient. In many medical applications, however, powered injectors are used in procedures and areas in which there are substantial time and access constraints. In time and/or access constrained procedures, loading of injection fluid into empty syringes using a powered injector, results in inefficient use of personnel, equipment, time and/or space.

It is, therefore, very desirable to develop improved syringe loading/filling devices, and systems and methods to improve the efficiency of use of personnel, equipment, time and/or space.

SUMMARY OF THE INVENTION

The present invention provides systems and methods for filling a medical container, such as a syringe, with a fluid. The fluid or medical container filling or loading systems described herein may include loading devices, such as a syringe loading device, fill stations and associated tubing and/or valve systems for transferring the fluid to the medical container to be filled. The present invention also includes the separate loading devices, fill stations and associated tubing and valve systems that together may comprise the medical container loading systems. Further, the present invention provides systems and methods for filling or loading a syringe, such as a hand-held syringe, by using the fill stations described herein. Moreover, the present invention broadly contemplates and provides a medical container loading system including a medical injector for use with the fill stations described herein to fill or load a medical container with fluid.

In one aspect, the present invention provides a medical container loading device for loading an injection fluid into a medical container, such as a syringe. In a preferred embodiment, the medical container is a syringe. The syringes for use with the syringe loader include a syringe plunger slidably disposed therein and an attachment mechanism for attachment of the syringe to an injector. The injector includes a mounting mechanism adapted to cooperate with the attachment mechanism on the syringe to mount the syringe on the injector. The syringe loader includes generally a syringe mounting mechanism adapted to cooperate with the attachment mechanism of the syringe to attach the syringe to the syringe loader and a drive member adapted to impart motion to the syringe plunger.

In one embodiment, the drive member includes a flange on a rearward end thereof that is manually operated by a user during loading. In another embodiment, the drive member is linked to a lever arm, which is rotatable to impart reciprocal linear motion to the syringe plunger. An axis of rotation about which the lever arm rotates can be fixed or movable (for example, to adjust the stroke thereof). In a further embodiment, the drive member is powered (for example, via connection with or integration with a powered screw drive).

Virtually any type of power source (for example, electric, hydraulic, pneumatic, etc.) can be used.

In still a further embodiment, the drive member includes one or more ratchet teeth. The syringe loader in this embodiment includes a rotating handle that is rotatable about an axis. The rotating handle has attached thereto on a first side of the axis a first pawl and on a second side of the axis a second pawl. The syringe loader also includes a mechanism to bring only one of the first pawl and the second pawl into cooperation with the ratchet teeth of the drive member at a given time. Rotation of the handle in a first direction causes forward movement of the drive member when the first pawl is brought into cooperation with the ratchet teeth. Rotation of the handle in the first direction causes rearward movement of the drive member with the second pawl is brought into cooperation with the ratchet teeth. The rotating handle is preferably biased in a second, "open" direction, opposite of the first direction.

In another aspect, the present invention provides a medical container loading device for loading an injection fluid into a medical container, such as a syringe including a syringe tip from which pressurized injection fluid exits the syringe during an injection procedure. The syringe loader includes a connector to connect a source of injection fluid to the syringe tip. The connector includes a first connection mechanism to connect to the syringe tip and a second connection mechanism to connect to the source of injection fluid. The connector further includes a valve to open and close the fluid connection between the source of injection fluid and the syringe tip. The connector also includes an inlet between the valve and the second connection mechanism that is adapted to pass a pressurized gas into the source of injection medium when the valve is closed. The valve is preferably openable after pressurized gas is passed into the source of injection fluid so that injection fluid is forced into the syringe via the syringe tip by the pressurized gas within the source of contrast fluid. In one embodiment, the syringe loader includes an air pump in fluid connection with the inlet to pass pressurized air into the source of injection fluid. The air pump can, for example, include a ball pump in fluid connection with a bladder.

In another aspect, the present invention provides a system including a syringe, an injector (preferably a powered injector) to pressurize an injection fluid loaded into the syringe, and a syringe loader to load the injection fluid into the syringe. The syringe loader is preferably operable independent of the injector. However, in an alternate embodiment, the operation of the syringe loader and the injector can be coordinated and/or interdependent, by means, for example, of a common control unit.

In a further aspect, the present invention provides a medical container loading device for loading an injection fluid into a medical container, such as a syringe, independent of an injector. The syringe includes a syringe plunger slidably disposed therein and an attachment mechanism for attachment of the syringe to the injector, as described above. Likewise, the injector includes a mounting mechanism to cooperate with the attachment mechanism on the syringe to mount the syringe on the injector. The syringe loader includes a syringe mounting mechanism adapted to cooperate with the attachment mechanism of the syringe to attach the syringe to the syringe loader and a drive member to impart motion to the syringe plunger.

In one embodiment, the drive member of the syringe loader is in operative connection with a manual lever arm. The lever arm can, for example, be in operative connection with the drive member via a linkage assembly. In one embodiment, the syringe loader includes a support frame having a first slot therein. In this embodiment, the lever arm can be rotatably connected to the drive member via a first pin positioned intermediate between the forward end and the rearward end of the lever arm. The first pin travels in the first slot during rotation of the lever arm. The support frame can further include a second slot formed therein. The lever arm in this embodiment has a second pin attached thereto at a position forward of the position of the first pin. The second pin travels in the second slot during rotation of the lever arm.

The syringe loader can also include a mount that is attachable to a surface, such as a wall or a table. Preferably, the support frame is removably attachable to the mount.

In still another aspect, the present invention provides a method of injecting a fluid into a patient using a medical container, such as a syringe, in which an injection fluid loaded into the syringe is pressurized by an injector. The method includes the step of loading the injection fluid into the syringe using a syringe loader that is operable independent of the powered injector.

The method can further include the step of mounting the syringe loader on a surface prior to loading the injection fluid. For example, the syringe loader can be mounted on a wall. The method further includes the steps of attaching the syringe to the syringe loader prior to loading the injection fluid into the syringe and removing the syringe from the syringe loader after loading of the syringe. The syringe can be attached to the syringe loader in generally the same manner in which the syringe is attached to the injector.

Moreover, the present invention provides a medical container loading system comprised of the medical container loading device for loading fluid into a medical container, such as a syringe, and a fill station, which is associated or used with the medical container loading device. The fill station is preferably located proximate to the medical container loading device. The fill station generally includes a mounting plate and a holding assembly. The holding assembly is connected to the mounting plate for supporting a medical fluid container generally adapted for fluid communication with the medical container to be loaded with fluid. The medical container loading device may be replaced by an injector, such that the injector is operable directly with the fill station.

The holding assembly may include a fixed support and a movable support connected to the mounting plate. The movable support is movable between an engaged position supporting the body of the medical fluid container to maintain the medical fluid container in the holding assembly and a disengaged position out of contact with the body of the medical fluid container.

A hook member may be connected to the mounting plate for supporting a medical fluid bag, such as those used to contain intravenous fluids often used with a syringe, including a hand-held syringe and/or a syringe to be used with an injector. The mounting plate may be configured to be wall-mounted. A shelf may be connected to the mounting plate. One or more hook members may be connected to the shelf. A clip may be connected to the mounting plate and be configured to receive and restrain fluid transfer tubing used with the medical fluid container and the medical container, in particular to place the medical fluid container in fluid communication with the medical container, such as a syringe.

The fixed support may comprise a U-shaped bracket connected to the mounting plate. The fixed support may further comprise a pair of support arms connected to the mounting plate. The movable support and the support arms, in combination, are preferably adapted to maintain the medical fluid container in the holding assembly. The movable support may comprise an adjustable strap.

The medical container loading system may further comprise a fluid transfer set for placing the medical container, such as a syringe, in fluid communication with the medical fluid container. The fluid transfer set may comprise a spike member configured to puncture a lid of the medical fluid container, a luer connection, a fluid transfer tube connecting the spike member and luer connection for fluid communication therebetween, and a stopper valve connected to the luer connection and configured for connection to a lid of the medical container.

In another embodiment, the medical container loading system comprises a loading device for loading fluid into the medical container and a fill station adapted for use with the loading device. The fill station is located proximate to the loading device and comprises a mounting plate and a holding assembly connected to the mounting plate for receiving and supporting the medical fluid container, which is adapted for fluid communication with the medical container. The fixed support and the movable support are each mounted to a base plate connected to the mounting plate. The movable support is preferably a resiliently biased support arm. The support arm preferably defines a central recess formed to cooperate with the body of the medical fluid container. The support arm may be supported on a pivot pin and be resiliently biased by torsion springs. The fixed support may include a pair of support arms, such that the movable support and the support arms, in combination, are adapted to maintain the medical fluid container in the holding assembly. The support arms may define apertures for viewing the contents of the medical fluid container. The support arms may curve inward and comprise integral support legs for supporting the body of the medical fluid container. A hook assembly may be connected to the mounting plate. The hook assembly comprises one or more hook members mounted to a support base, which in turn is connected to the mounting plate. The mounting plate may be wall-mounted. A transfer tubing clip may also be connected to the mounting plate.

In another embodiment, the fill station may comprise a holding assembly with at least one substantially funnel-shaped fixed support connected to the mounting plate for receiving and supporting the medical fluid container. A hook member may be connected to the fixed support for supporting the medical fluid bag. The mounting plate and fixed support may be formed integrally from plastic. The inner wall of the fixed support may be stepped to accommodate different sized medical fluid containers. The fixed support may comprise a split sidewall for passing fluid transfer tubing therethrough.

In a further embodiment, the fill station may comprise a holding assembly with a substantially rectangular shaped fixed support connected to the mounting plate for receiving and supporting the medical fluid container. The fixed support may include an inclined inner support or wall for supporting the body of the medical fluid container. The mounting plate and the rectangular shaped fixed support may be formed integrally from plastic.

An additional method of preparing a medical container, such as a syringe, for connection to the injector may generally follow the sequence of connecting a medical container to a loading device adapted to load fluid into the medical container, loading a medical fluid container in a fill station located proximate to the loading device, connecting the medical fluid container to the medical container with a fluid transfer set, loading medical fluid from the medical fluid container into the medical container, disconnecting the medical container from the medical fluid container, disconnecting the medical container from the loading device, and connecting the medical container to the injector. The medical container may be a syringe.

The present invention also provides a fluid transfer set generally used to place the medical container used in the loading device in fluid communication with the medical fluid container supported in the fill station. The fluid transfer set generally comprises a spike member, a luer connection, a fluid transfer tube, and a valve. The spike member is configured for fluid communication with the medical fluid container. The spike member preferably has a distal end formed to puncture a lid of the medical fluid container and a proximal end. The tube connects the spike member and the luer connection for fluid communication therebetween. The valve, for example a stopper valve, is connected to the luer connection and is configured for connection to the medical container. The tube preferably connects the proximal end of the spike member to the luer connection. The luer connection may comprise a female luer connection.

The tube may be secured adhesively to the spike member and the luer connection. The valve may be a one-way stopper-type valve. The valve and the luer connection may be connected by a threaded connection. The valve and luer connection may be formed integrally from plastic, such as polycarbonate. The luer connection may comprise a pair of wings for grasping by a user of the fluid transfer set.

The valve may be configured for threaded connection to the syringe. The valve may comprise a tubular housing and an internal closure member within the housing for closing the valve. The closure member may have an exposed end at one end of the housing. The exposed end may define a substantially planar surface for ease in sterilizing the exposed end and the end of the housing. The luer connection and housing may be formed integrally of plastic, such as polycarbonate. The luer connection and housing may be connected by a threaded connection. The housing may be configured for a threaded connection to the syringe.

The present invention also provides a valve for medical fluid transfer applications. The valve generally comprises a tubular housing and an internal closure member within the housing for closing the valve. The closure member has an exposed end at one end of the housing. The exposed end defines a substantially planar surface for ease in sterilizing the exposed end and the end of the housing. The end of the housing may be configured for threaded connection to a syringe. The other end of the tubular housing may be configured for threaded connection to a luer connection. The housing and closure member are preferably made of plastic, such as polycarbonate.

The medical container loading/filling devices, fill stations, systems and methods of the present invention improve the efficiency of use of personnel, equipment, time and/or space in injection procedures as compared to current practices. Moreover, the medical container loading/filling devices, fill stations, systems and methods of the present invention are relatively inexpensive to manufacture and implement. Furthermore, spills or leaks of injection fluid often occur during loading of injection fluid. Such spills or leaks of injection fluid can be very harmful to powered injectors if the injection fluid passes into the injector housing. The medical container loading/filling devices, fill stations, systems and methods of the present invention assist in preventing damage to injectors from such spills or leaks.

Moreover, the medical container loaders of the present invention are readily made suitable for use in or near an MR environment. In that regard, the materials and operation of the loaders of the present invention preferably do not substantially interfere with MRI equipment, and preferably the loader does not experience excessive forces as a result of the relatively strong magnetic fields generated in an MR environment. In general, polymeric materials and nonferrous metals (for example, aluminum or TEFLON® impregnated aluminum) are preferred construction materials for use in the loaders of the present invention when such loaders are to be used in or near an MR environment. Nonferrous metals and/or polymeric materials that are, for example, lubricious, low friction and/or "non-stick" can be used in the mounts or interfaces of the loaders of the present invention. Examples of suitable polymeric materials include polycarbonate and DELRIN® available from E.I. duPont de Nemours & Co. of Wilmington, Del.

Further details and advantages of the inventions summarized hereinabove will become apparent from the following detailed description when read in conjunction with the drawings.

BRIEF DESCRIPTION OF THE DRAWINGS

FIG. 2 is a side view of another embodiment of a front-loading injector having a different releasable mounting mechanism in accordance with the present invention;

FIG. 4A is a side, cross-sectional view of a second embodiment of a syringe loader of the present invention with the plunger extension thereof in a rearward or retracted position;

FIG. 4B is a side, cross-sectional view of the syringe loader of FIG. 4A with the plunger extension thereof in a forward position;

FIG. 4C is a side, cross-sectional view of a syringe loader of the present invention including a powered plunger extension;

FIG. 4D illustrates the syringe loader of FIG. 4C with a syringe adapter and a plunger adapter for use with an alternative syringe and the syringe loader;

FIG. 5D is a top, cross-sectional view of an embodiment of a syringe interface of the syringe loader of FIG. 5A with a syringe of a second size connected thereto;

FIG. 5I illustrates top views of one embodiment of a process for using the syringe loader of FIG. 5A;

FIG. 6B illustrates side, cross-sectional views of the syringe loader of FIG. 6A during a fluid expelling cycle and a fluid loading cycle;

FIG. 8 is a perspective view of a syringe loading system of the present invention incorporating a syringe loader and a fill station according to one embodiment of the present invention;

FIG. 16 is a top plan view of the fill station shown in FIG. 15, with the fluid container illustrated in FIG. 15 removed for clarity;

DETAILED DESCRIPTION OF THE INVENTION

The medical container loading systems and devices of the present invention can be used separately or in combination together with a wide variety of medical containers, such as syringes (including hand-held syringes), and injectors, including powered injectors. A couple of powered injectors and syringes in connection with which the medical container loaders of the present invention can be used are described below.

Figure 1:
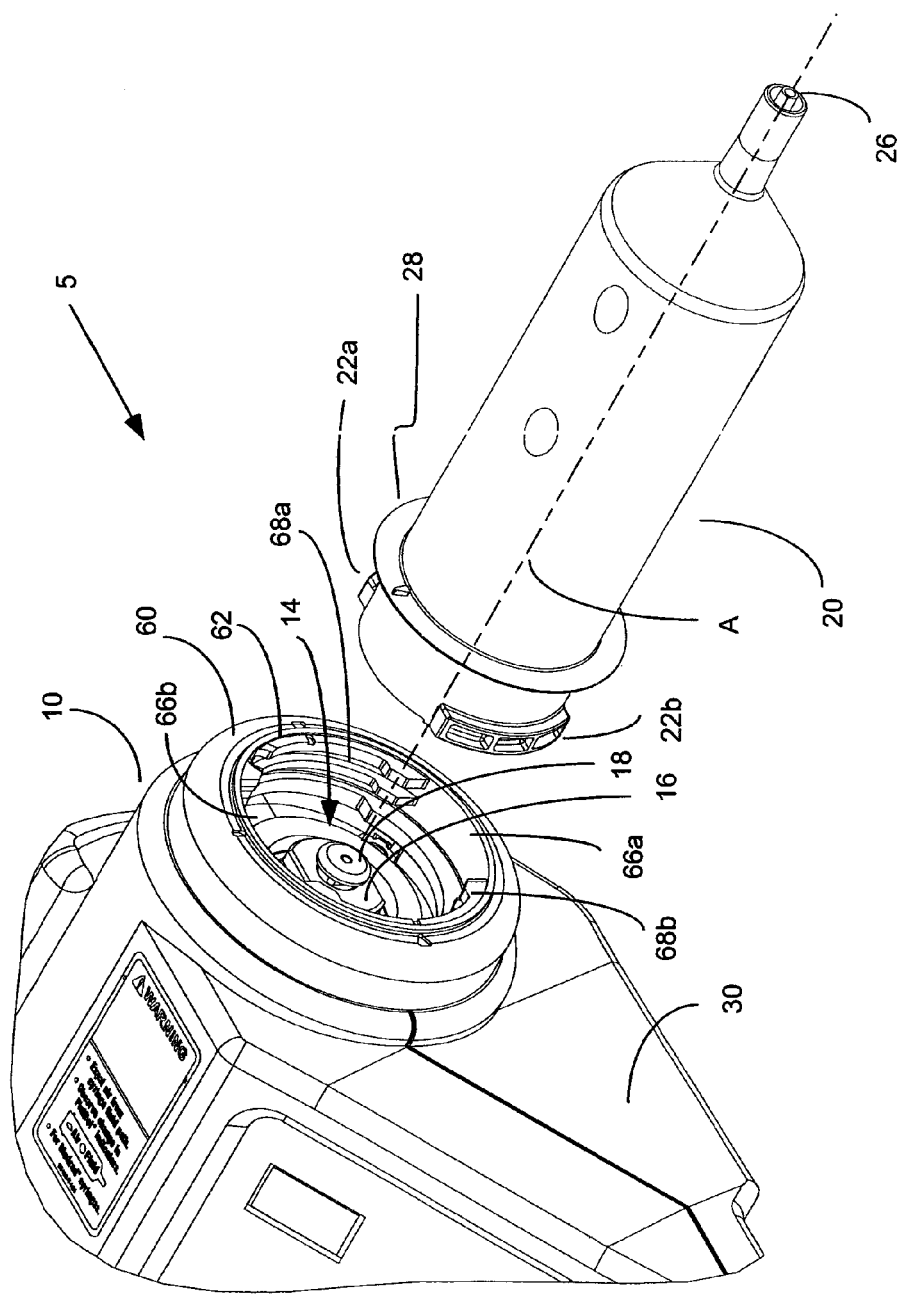
FIG. 1 is a perspective view of an embodiment of an injector system according the present invention including a powered injector and a front-loading syringe.

An embodiment of a front-loading injector system 5 is illustrated in FIG. 1. Injector system 5 includes a powered injector 10 and a syringe 20 for injection of, for example, a contrast medium. As illustrated in FIG. 1, injector housing 30 of injector 10 preferably includes a first drive member or piston 14 therein which cooperates with a syringe plunger 40 (not shown in FIG. 1; see, for example, FIGS. 3E or 5C) slidably disposed in syringe 20 to inject a fluid from the interior of syringe 20 into a patient.

As used herein, the terms "axial" or "axially" refer generally to, for example, an axis A around which syringe 20 and piston 14 are preferably formed (although not necessarily symmetrically therearound) and to directions collinear with or parallel to such an axis. The terms "proximal" or "rearward" refer generally to an axial or a longitudinal direction toward the end of syringe 20 opposite a syringe tip 26 (from which pressurized fluid exits syringe 20). The terms "distal" or "forward" refer generally to an axial or a longitudinal direction toward the syringe tip 26 of syringe 20. The term "radial" refers generally to a direction normal to an axis such as axis A.

Syringe 20 is removably connected to injector 10 as described, for example, in U.S. Pat. No. 5,383,858, the disclosure of which is incorporated herein by reference. In that regard, front-loading injector 10 preferably includes a front portion or interface 60 having a first recess 62 formed therein. Piston or drive member 14 is reciprocally mounted within injector 10 and is extendible through recess 62. Piston 14 preferably includes a piston flange or head 16 to assist in forming a connection with the syringe plunger. Interface 60 includes receiving slots, 66a and 66b, which are preferably positioned opposite one another around recess 62. Receiving flanges 68a and 68b are preferably positioned opposite one another and between receiving slots 66a and 66b, and extend inwardly into recess 62.

The rearward end of syringe 20 preferably includes a releasable mounting mechanism such as a pair of mounting flanges 22a and 22b for mounting syringe 20 in a desired position relative to the housing 30 of injector 10. Flange 22a is not well shown in FIG. 1 but is generally identical to flange 22b and positioned opposite flange 22b (see, for example, FIG. 5C).

To attach syringe 20 to injector 10, the rearward end of syringe 20 is inserted into injector recess 62 such that mounting flanges 22a and 22b are inserted into receiving slots 66a and 66b, respectively. In one embodiment, piston flange 16 is preferably simultaneously aligned to engage a capture mechanism (including, for example, L-shaped capture members 42 and 44—see, for example, FIGS. 3E or 5C) on the rear of syringe plunger 40 (as, for example, described in U.S. Pat. No. 5,383,858). As clear to one skilled in the art, however, many other plunger and piston designs are possible to connect the piston 14 to the plunger 40.

Figure 3A:
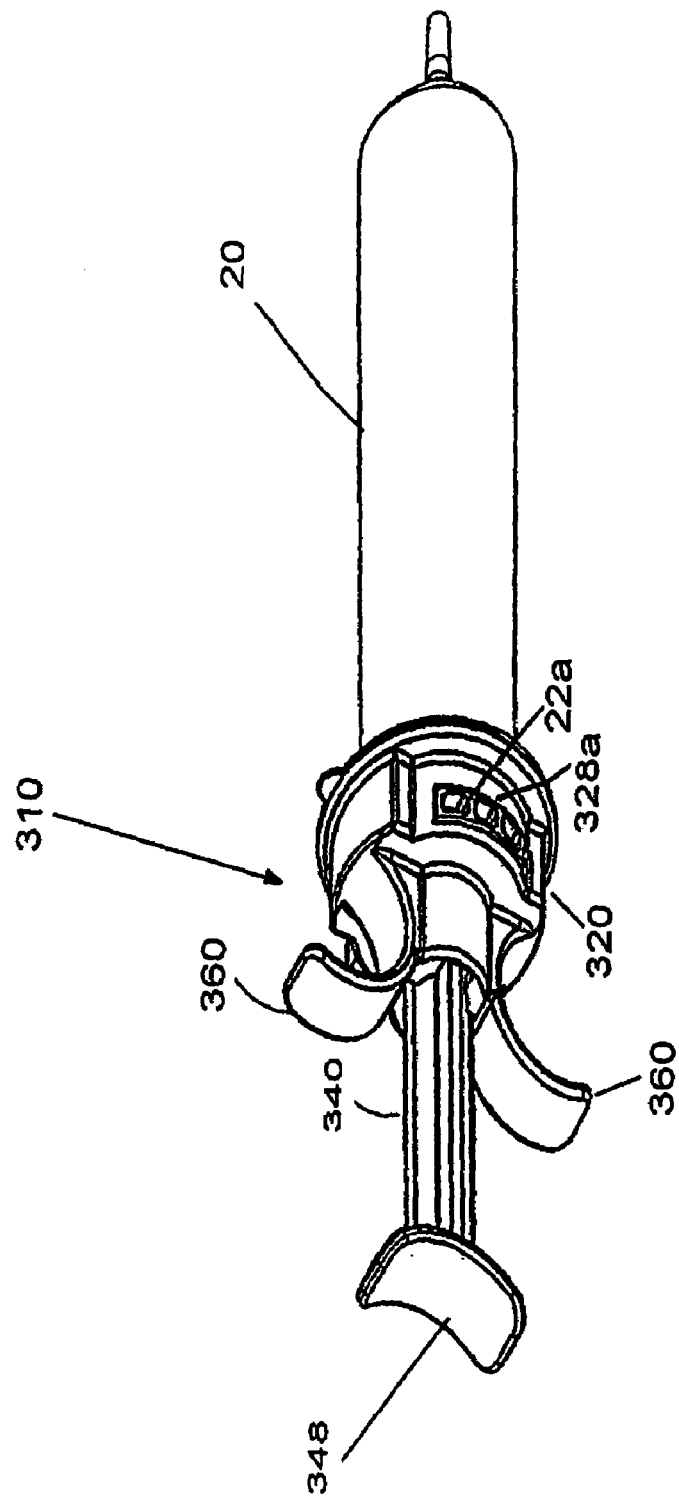
FIG. 3A is a perspective view of a first embodiment of an off-injector syringe loader of the present invention in which the syringe loader is connected to the syringe.
Figure 3B:
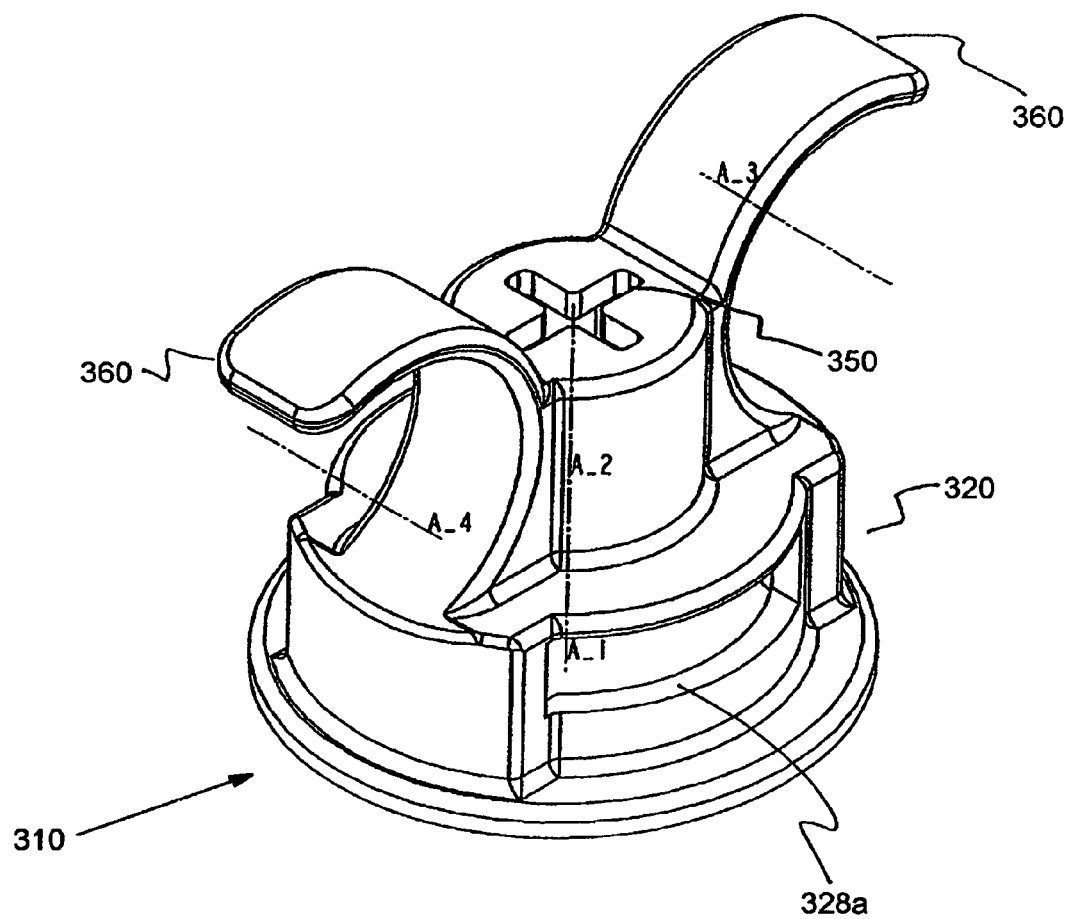
FIG. 3B is a perspective view of the syringe loader of FIG. 3A in which the syringe has been disconnected from the loader.
Figure 3C:
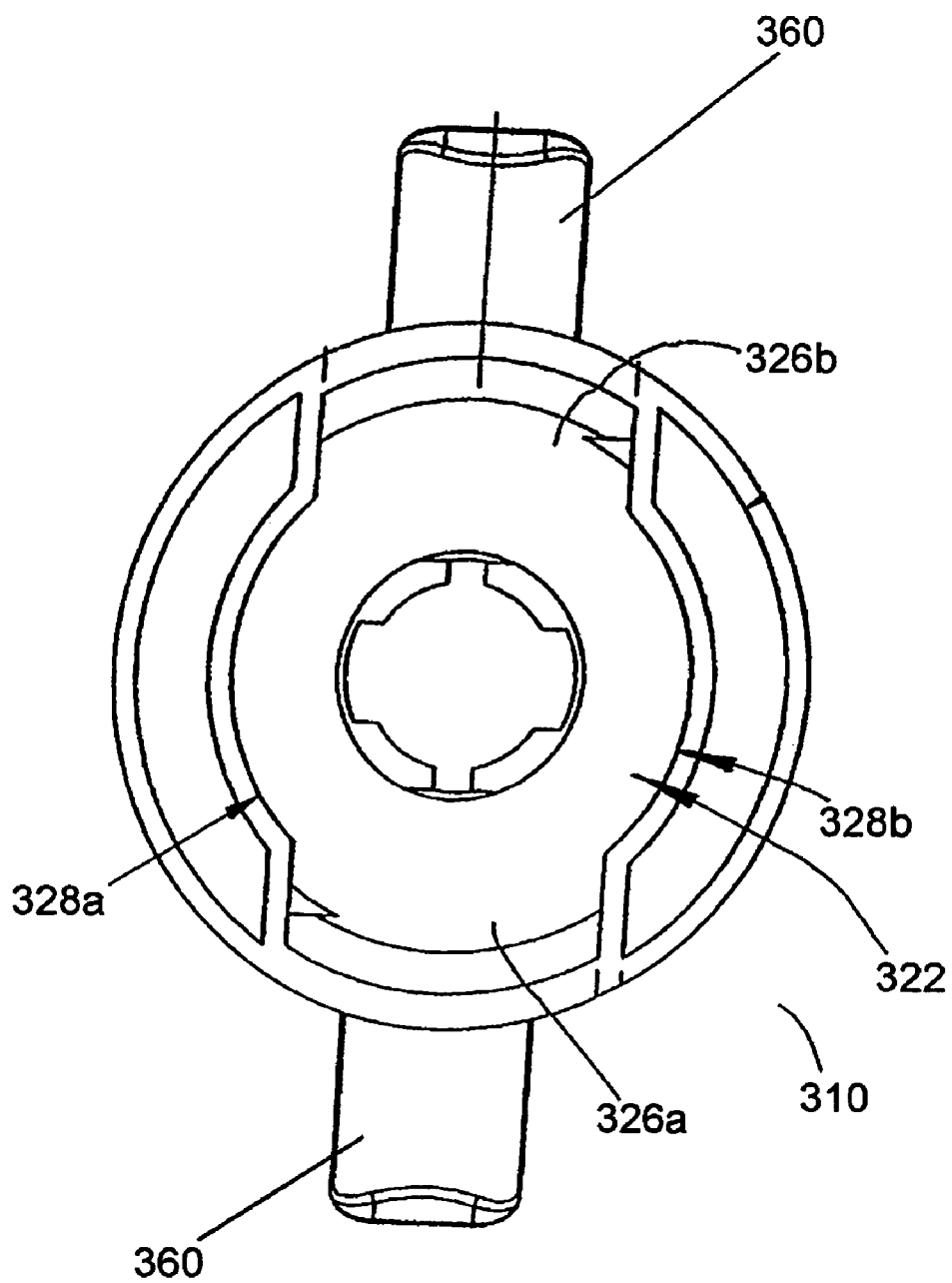
FIG. 3C is a front view of the syringe loader of FIG. 3A.
Figure 3D:
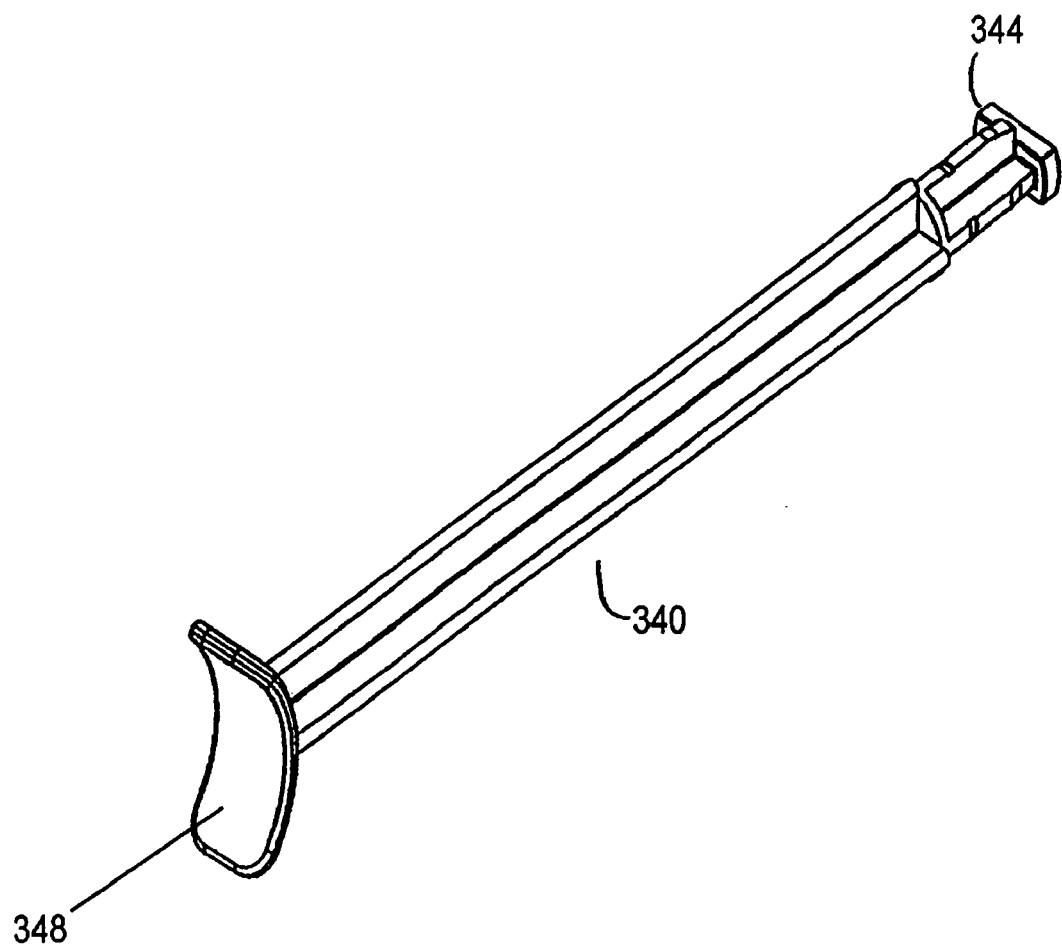
FIG. 3D is a perspective view of the plunger extension of the syringe loader of FIG. 3A.
Figure 3E:
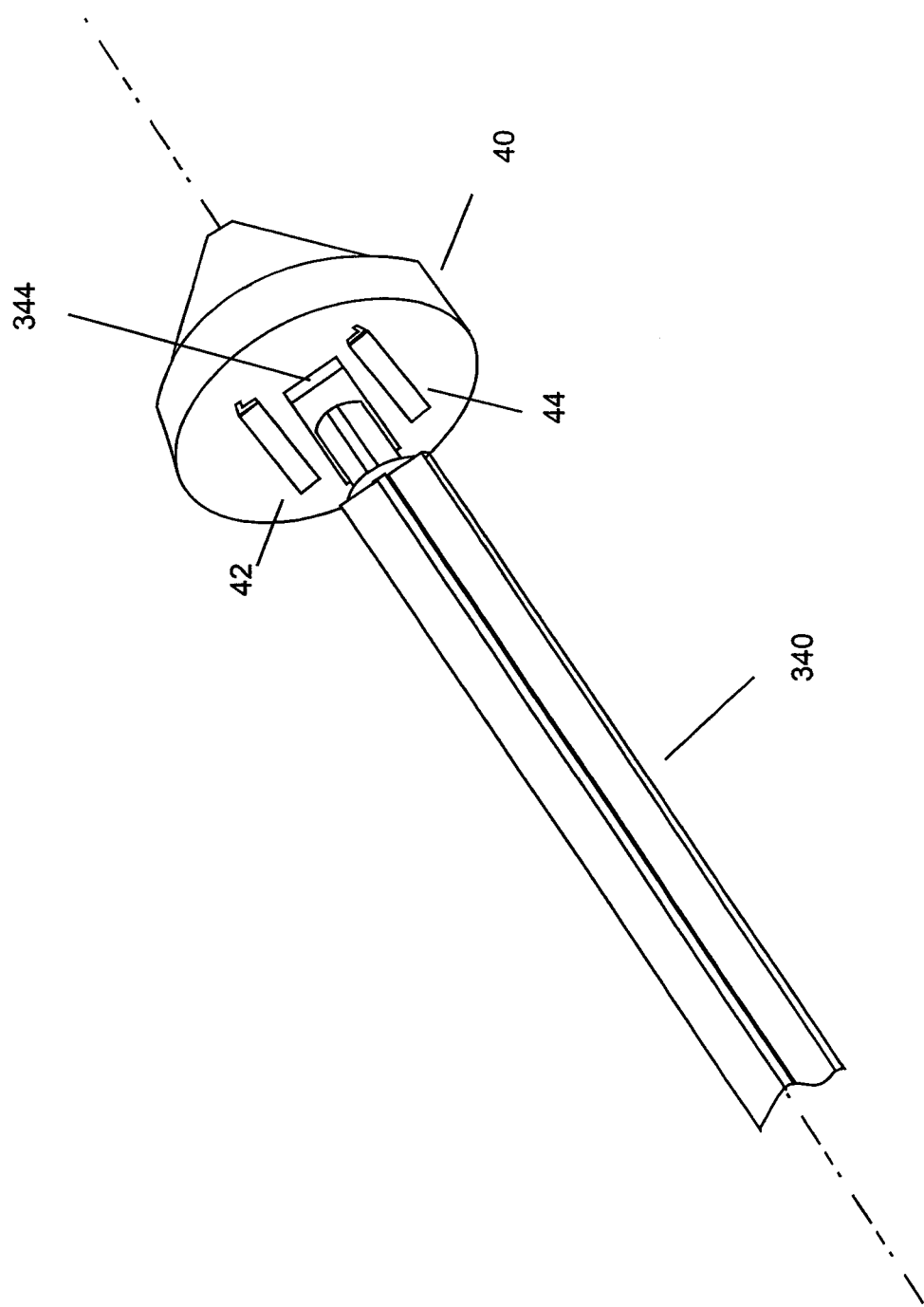
FIG. 3E is a perspective view of the plunger extension of the syringe loader of FIG. 3A aligned with the syringe plunger.
Figure 5A:
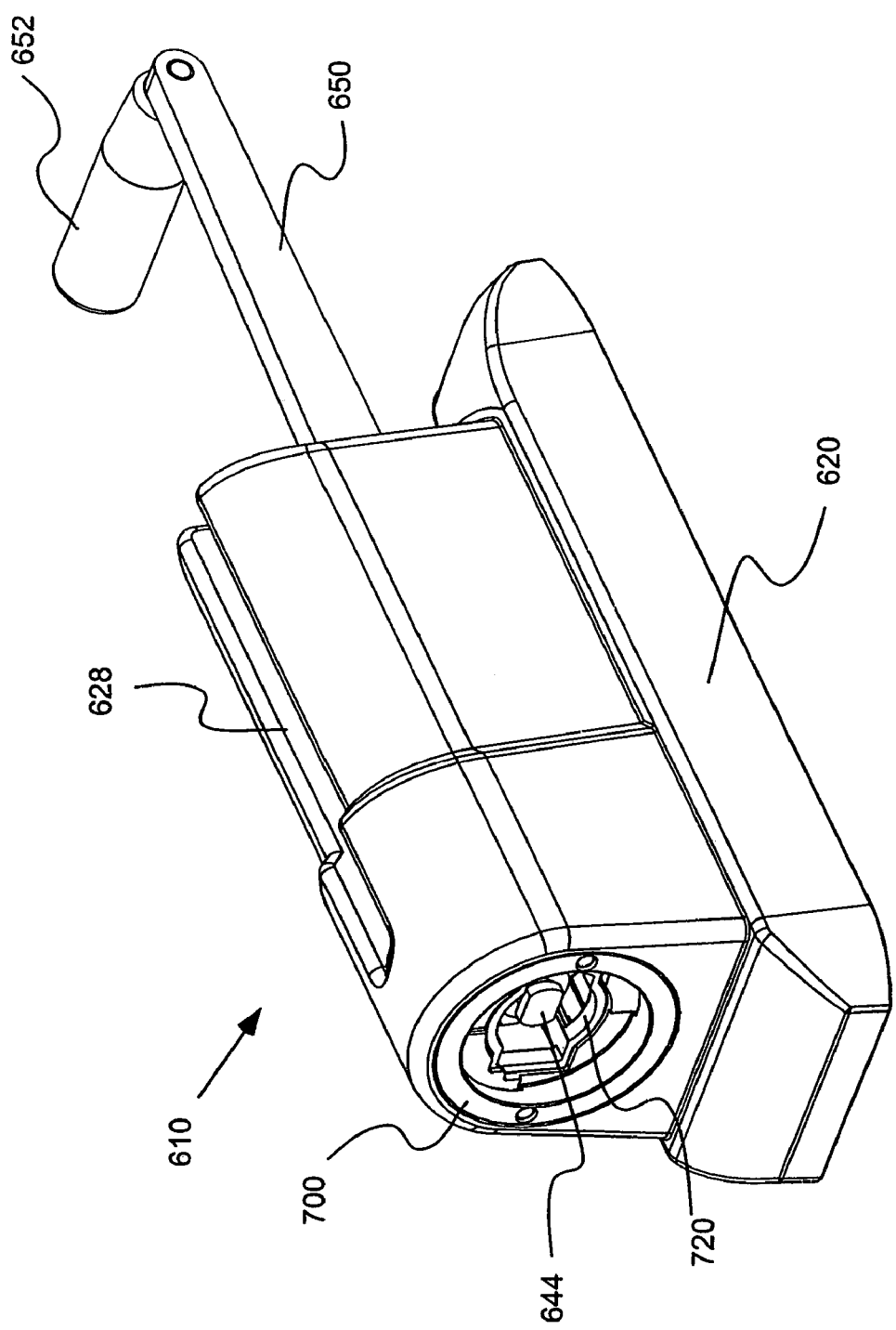
FIG. 5A is a perspective view of another embodiment of a syringe loader of the present invention.
Figure 5B:
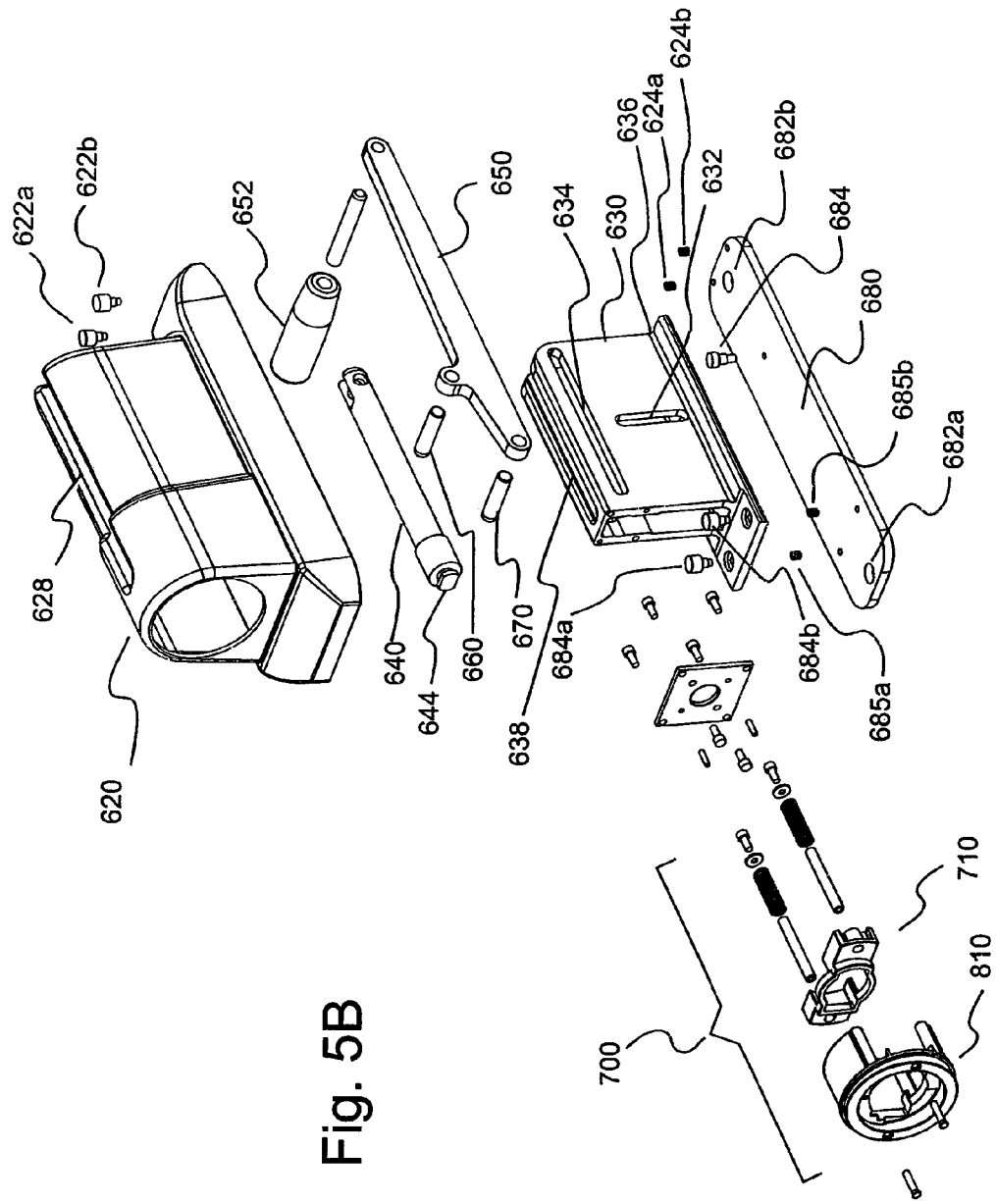
FIG. 5B is a perspective, exploded or disassembled view of the syringe loader of FIG. 5A.
Figure 5C:
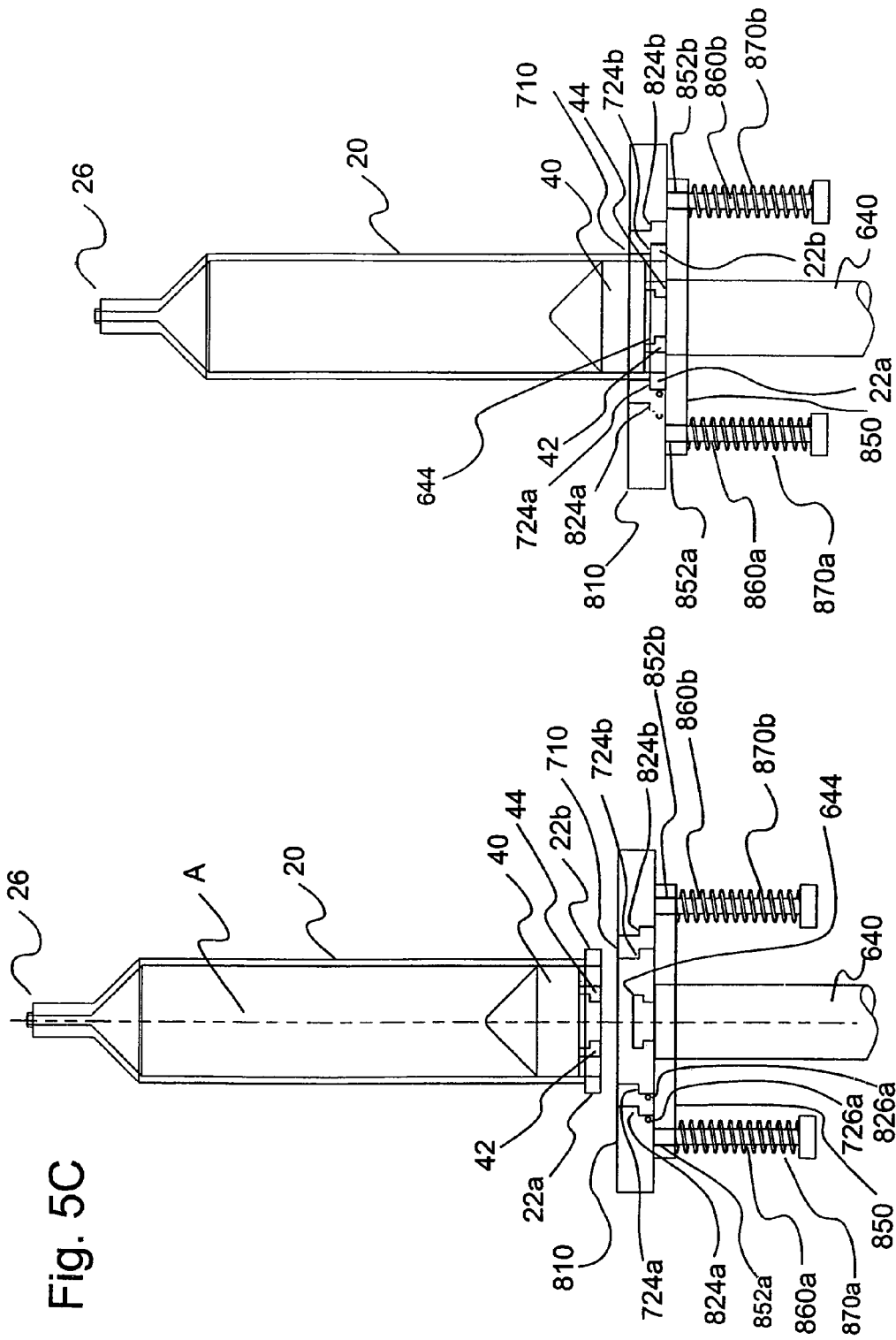
FIG. 5C is a top, cross-sectional view of an embodiment of a syringe interface of the syringe loader of FIG. 5A with a syringe of a first size connected thereto.

Once mounting flanges 22a and 22b are inserted into receiving slots 66a and 66b, respectively, and piston 14 is in position to be received by plunger 40, the operator rotates syringe 20 approximately 90 degrees such that mounting flanges 22a and 22b move behind and are engaged by receiving flanges 68a and 68b, respectively, and piston flange 14 is retained by, for example, L-shaped capture members 42 and 44 on plunger 40 (see, for example, FIG. 3E or 5C). Injector 10 may include a stop mechanism (not shown), for example, extending from at least one of the retaining slots 68a and 68b, to prevent rotation of syringe 20 more than 90 degrees. Tactile, visual or audible feedback can be provided to the operator via, for example, cooperating members on syringe 20 and injector 10 to inform the operator that secure connection has been achieved. After securely attaching syringe 20 to injector 10, advancing piston 14 in a forward direction will apply a motive force to plunger 40 to advance plunger 40 forward within syringe 20, thereby forcing the contents of syringe 20 out of syringe tip 26 into the fluid path to the patient. Retracting piston 14 in a rearward direction will cause plunger 40 to move rearward within syringe 20, thereby drawing fluid into syringe 20.

As known in the art, syringes can be attached to a wide variety of front-loading injectors through use of syringe adapters. In that regard, FIG. 2 illustrates another embodiment of an injector 114 and a syringe 250 having a different releasable mounting mechanism 110 than described above for injector 10. Release mechanism 110 includes a connector housing 124, which contains at least two elements that facilitate connection of syringe 250 to an injector 114. The first element is a flexible ring 126 disposed within release mechanism 110 near front end 120. The second element is a rotating ring 128 disposed within release mechanism 110 near rearward end 116. Flex ring 126 and rotating ring 128 cooperate with one another to permit connection and release of syringe 250 to and from release mechanism 110 (and, accordingly, to and from injector 114). Injector 114 and release mechanism 110 are described in detail in U.S. patent application Publication No. 2001-0047153, the contents of which are incorporated herein by reference.

In general flex ring 126 distends to an "open" shape when contacted by a sloped shoulder 260 on a rearward end of syringe 250 and then snaps back to a relaxed state once shoulder 260 passes thereby to retain syringe 250 within releasable mounting mechanism 110. After connection, rotation of syringe 250 about its axis (for example, approximately 90°) causes rotation of rotating ring 128 disposed within release mechanism 110 via cooperation of tab 270 with abutment members or grooves (not shown) on rotating ring 128. Rotation of ring 128 causes flex ring 126 to distend to its open shape to allow shoulder 260 to pass forward of flex ring 126 for removal of syringe 250 from releasable mounting mechanism 110.

Under current practice, powered injectors such as injector 10 or injector 114 are often used to load or fill empty syringes with injection fluid (for example, a contrast medium). As discussed above, this methodology often results in inefficient use of equipment, personnel, time and/or space. FIGS. 3A–3E illustrate an embodiment of an off-injector, syringe loader 310 that can be used to load injection fluid into, for example, syringe 20 before syringe 20 is mounted upon injector 10. Syringe loader 310 includes a syringe mount 320 to removably attach syringe 20 thereto. In general, syringe 20 is connected to syringe mount 320 in the same way that syringe 20 is mounted to injector 10. In that regard, as best shown in FIG. 3B syringe mount 320 includes an opening 322 having receiving slots 326a and 326b positioned around the perimeter thereof. To attach syringe 20 to syringe mount 320 of loader 310, the rearward end of syringe 20 is inserted into opening 322 such that mounting flanges 22a and 22b are inserted into receiving slots 326a and 326b, respectively.

Once mounting flanges 22a and 22b are inserted into receiving slots 326a and 326b, respectively, the operator rotates syringe 20 approximately 90 degrees such that mounting flanges 22a and 22b move behind and are engaged by receiving flanges 328a and 328b, respectively. Tactile, visual or audible feedback can be provided to the operator as described above to inform the operator that secure connection has been achieved. After securely attaching syringe 20 to syringe loader 310, advancing a plunger extension or stem 340 in a forward direction will apply a motive force to the syringe plunger to advance the plunger forward within syringe 20, thereby expelling injection fluid from syringe tip 26. Likewise, retracting plunger extension 340 in a rearward direction will cause the plunger to move rearward within syringe 20, thereby drawing fluid into syringe 20. Syringe loader 310, when syringe 20 is connected thereto, thus operates similarly to a manual syringe and can be manually operated to load a desired amount of injection fluid into syringe 20. The loaded or filled syringe can then be mounted upon injector 10 as described above for injection of the fluid into a patient.

In one embodiment (see FIG. 3D), a flange 344 on a distal end of plunger extension 340 preferably engages a capture mechanism such as L-shaped capture members 42 and 44 on the rear of a syringe plunger 40 (see FIG. 3E; as, for example, described in U.S. Pat. No. 5,383,858). Preferably, this engagement occurs as syringe 20 is connected to loader 310. For example, plunger extension 340 is preferably in position to be received by plunger 40 when syringe 20 is inserted into opening 320. In that regard, syringe manufacturers typically ship syringes with the syringe plunger in a known position (for example, fully retracted). Loader 310 is preferably designed such that, for example, the fully retracted position of plunger extension 340 positions flange 344 to be received by plunger 40 when syringe 20 is fully inserted within opening 320.

When the operator rotates syringe 20 approximately 90 degrees such that mounting flanges 22a and 22b move behind and are engaged by receiving flanges 368a and 368b, respectively, flange 344 preferably rotates to engage L-shaped capture members 42 and 44. In this embodiment, plunger extension 340 is preferably slidably disposed within loader 310 such that plunger extension 340 cannot rotate about its axis relative to syringe mount 320 to ensure suitable alignment as described above. In the embodiment of FIGS. 3A through 3E, for example, plunger extension has a generally cross-shaped cross section which is slidably disposed within an correspondingly shaped opening 350 of loader 310 to prevent rotation of plunger extension 340 relative to the remainder of syringe loader 310.

Syringe loader 310 further includes finger grips 360 to facilitate manual operation thereof. Likewise, plunger extension 340 includes a rear flange 348 to facilitate manual operation of syringe loader 310.

FIGS. 4A and 4B illustrate another embodiment of an off-injector syringe loader 410 of the present invention. Syringe loader 410 includes a syringe mount 420 that operates generally in the manner of the mounting mechanism of interface 60 of injector 10 as well as syringe mount 320. A plunger extension 440, which imparts motion to plunger 40 as described above, is slidably disposed within the housing of syringe loader 410 to pass through a passage in syringe mount 420. Plunger extension 440 is in operative connection with a lever arm 450 via a linkage assembly arm 460. Lever arm 450 is rotatable about axis A" defined, for example, by a pin attached to a base member 470 to which syringe mount 420 is also preferably attached. Lever arm 450 provides mechanical advantage for ease of operation. Base 470 is preferably attachable to a surface (for example, a counter top or a wall) via any suitable attachment means (for example, screws). FIG. 4B illustrates rotation of lever arm 450 to a forward position to advance plunger 40 to a forward position within syringe 20. FIG. 4A illustrates rotation of lever arm 450 to a rearward position to allow syringe 20 to be mounted to syringe loader 410 (or to retract plunger 40 to a rearward position within syringe 20).

FIG. 4C illustrates an off-injector syringe loader 510, similar in operation to syringe loader 410. However, lever arm 450 of syringe loader 410 is replaced by a powered drive mechanism 550, such as a screw drive. Powered screw drive 550 is operatively connected to plunger extension 440 via a connecting member 560. Drive screw 550 and thereby plunger extension 440 and plunger 40 can, for example, be controlled via a control pad 580. Because syringe loader 510 preferably is not used to inject fluid into a patient, but only to load injection fluid into syringe 20, any control circuitry/software used to operate drive screw 550 can be much less complicated and costly than similar control circuitry/software required in, for example, a powered injector such as injector 10 or injector 114.

FIG. 4D illustrates use of an adapter 590 including a forward portion 110' that operates in generally the same manner as releasable mounting mechanism 110 described above to attach syringe 250 thereto. A rearward portion of adapter 590 includes flanges 22a' and 22b' to attach adapter 590 to syringe mount 420 of syringe loader 410 or 510, thereby adapting syringe 250 for use with syringe loader 410 or 510. In the case that capture member 44a of plunger 40a differs from L-shaped capture members 42 and 44 described above, a plunger adapter 594 can be used to connect plunger extension 440 to plunger 40a of syringe 250.

Figure 4E:
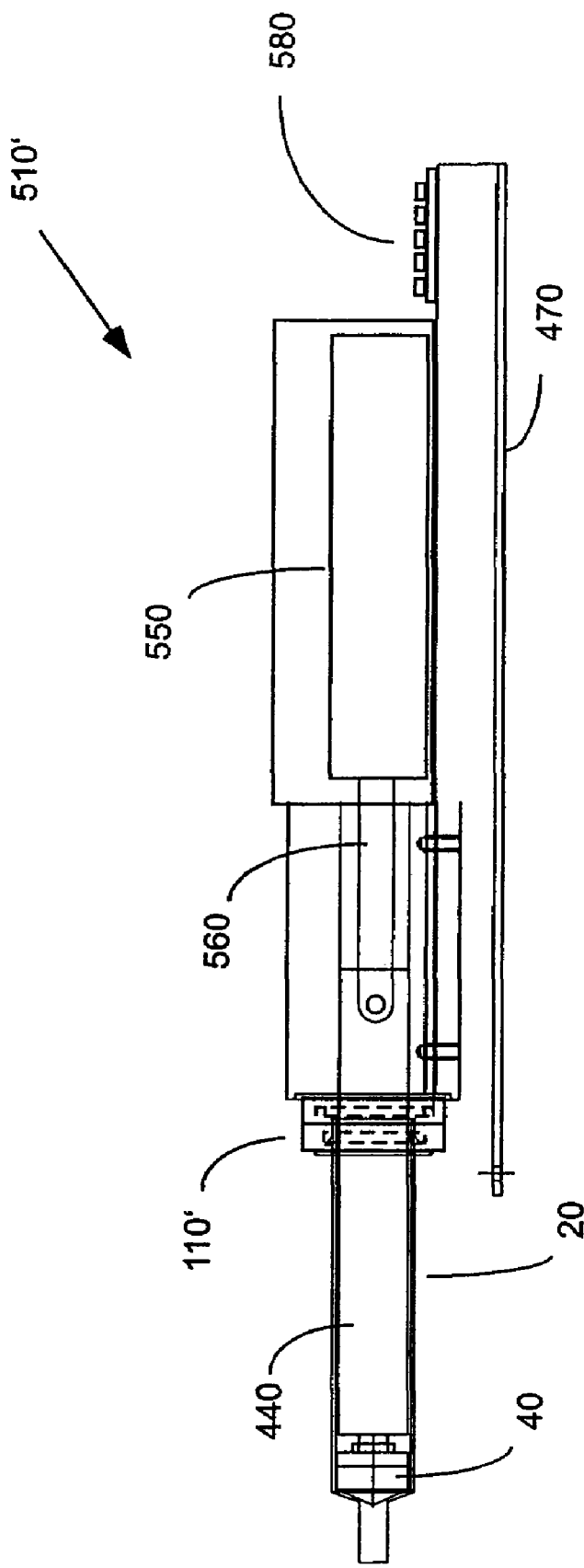
FIG. 4E illustrates the syringe loader of FIG. 4C with a different syringe mount for use with the syringe loader with an alternative syringe.

As illustrated in FIG. 4E, syringe mount 420 can also be replaced with syringe mounting mechanism 110' to connect syringe 250 directly to syringe loader 510' without use of an adapter. As clear to one skilled in the art, many other sizes and/or types of syringes can be accommodated by the syringe loaders of the present invention by use of corresponding syringe mounts or adapters. A syringe mounting mechanism of the syringe loaders of the present invention can easily be made removable (using, for example, cooperating slots and flanges) to facilitate use of different syringe mounts for different syringes. Moreover, more than one syringe mount can be included in a single syringe mounting mechanism, which can, for example, be slidable or rotatable to bring the appropriate syringe mount for a particular syringe into operation.

FIGS. 5A through 5I illustrate another embodiment of an off-injector syringe loader 610 of the present invention. Syringe loader 610 includes a syringe mount or syringe interface 700 that operates similar to the manner of the mounting mechanism of interface 60 of injector 10 as well as syringe mounts 320 and 420. However, syringe interface 700, which is discussed in further detail below, is suitable to attach syringes of different size to syringe loader 610 without the use of any adapter(s) and without user manipulation/adjustment of the mechanics of syringe loader 610.

Syringe loader 610 includes an outer housing 620 and a support frame 630 housed within housing 620. In one embodiment, housing 630 was fabricated from TEFLON-impregnated aluminum. A plunger extension 640 adapted to impart motion to, for example, plunger 40 (as described above), is slidably disposed within support frame 630 of syringe loader 610 to pass through a passage 720 in syringe mount 700. Plunger extension 640 is in operative connection with a lever arm 650 via, for example, a pin 660. Lever arm 650 is rotatable to advance or retract plunger extension 640 via a dual slot arrangement as illustrated, for example, in FIGS. 5B and 5F. In that regard, lever arm 650 is attached to a pin 670 at a forward end thereof. As lever arm 650 is rotated (via, for example, application of force to handle 652) in a forward direction from its rearward position (see, for example, FIGS. 5F and 5I) to advance plunger extension 640, pin 670 travels downward (in the orientation of, for example, FIGS. 5B and 5F) within a slot 632 formed in support frame 630, and pin 660 travels forward within slot 634 formed within support frame 630. The motion of pins 660 and 670 within slots 634 and 632, respectively, and the motion of lever arm 650 are represented by arrows in FIG. 5F. Lever arm 650 provides mechanical advantage for ease of operation. Using the dual slot linkage arrangement of syringe loader 610, the stroke of the lever arm can be reduced as compared to the linkage assemblies used in syringe loaders 410 and 510 while providing similar mechanical advantage. During rotation, lever arm 650 travels through upper slots 638 and 628 formed in support frame 630 and housing 620, respectively.

Figure 5E:
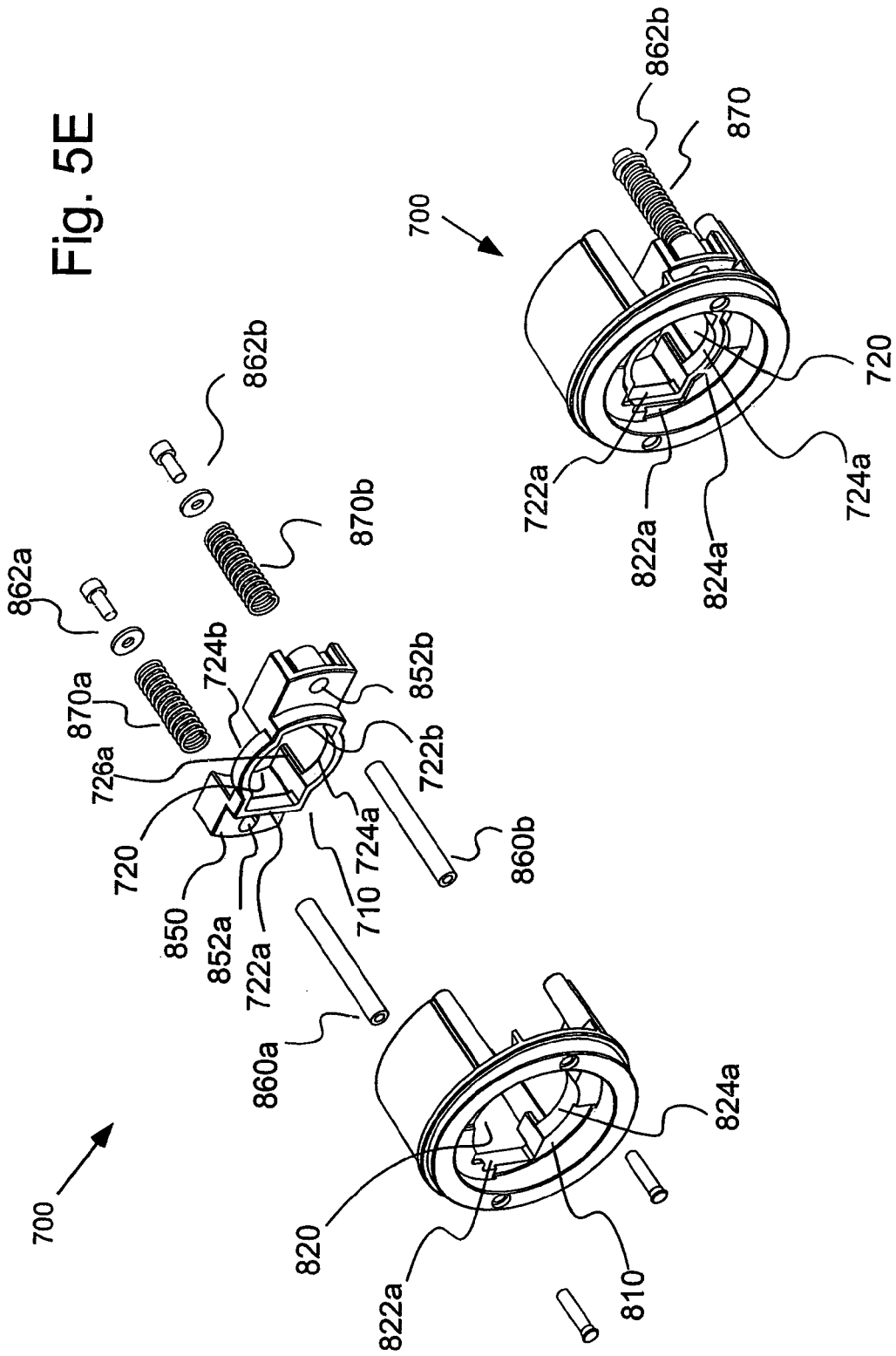
FIG. 5E is a perspective view of the syringe interface of FIGS. 5C and 5D in an exploded or disassembled state and in an assembled state.

Similar to syringe loader 410, syringe loader 610 preferably includes a base or mounting plate 680, which is preferably attachable to a surface (for example, a counter top or a wall) via any suitable attachment means. FIG. 5G illustrates one embodiment of a sequence of steps carried out to mount syringe loader 610 to a wall as follows:

1. Mounting plate 680 is preferably positioned in a desired location (for example, near the entrance outside of or within an MR room) such that top/forward mounting hole 682a is preferably between approximately 49 inches and approximately 53 inches from the floor to facilitate use by personnel of different heights. When mounting upon a wall of stud construction, mounting holes 682a and 682b are preferably positioned over a stud.
2. While maintaining mounting plate 680 in a generally vertical position, the locations of mounting holes 682a and 682b can be marked.
3. Pilot holes can then be drilled into the mounting surface at the marked locations for anchorage of suitable mounting hardware for mounting plate 680 as known in the art (for example, 2¼ inch tap con screws for wood studs and masonry, or hollow wall anchors for metal studs and drywall).
4. Mounting plate 680 is then affixed to the wall via mounting holes 682a and 682b.
5. After attachment of mounting plate 680 to the wall, support frame 630 is connected to mounting plate 680. In one embodiment (as illustrated in FIGS. 5A thorough 5G), support frame 630 is slid onto mounting plate 680 until a slot 683 formed in a base flange 636 of support member 630 is fully seated onto an alignment stud 684 projecting from base plate 680.
6. In this embodiment, support frame 630 is then rotated until generally aligned with mounting plate 680, with lever arm 650 at the bottom (in the orientation of FIG. 5G).
7. At this point, thumb screws 684a and 684b positioned at the top/rear of support frame 630 are tightened to secure support frame 630 to mounting plate 680. Thumbscrews 684a and 684b can be spring loaded using, for example, springs 685a and 685b.
8. Housing 620 is then slid onto support frame 630 until it is fully seated as shown in FIG. 5G.
9. Thumbscrews 622a and 622b positioned at the bottom/front of the housing 620 are then tightened to secure housing 620 to mounting plate 680. Thumbscrews 622a and 622b can be spring loaded using, for example, springs 624a and 624b.

As described above, adapters can be used to attach different types and/or sizes of syringes to the syringe loaders of the present invention. However, attachment of adapters can use valuable operator time and storage/retrieval of multiple types of adapters can be a problem. Alternatively, a syringe mount or interface that is suitable to attach more than one size of syringe thereto can be provided. Such syringe interfaces are described in U.S. patent application Ser. No. 10/233,844, filed on Sep. 3, 2002, assigned to the assignee of the present invention, the disclosure of which is incorporated herein by reference.

In general, such syringe interfaces include a plurality of syringe mount apertures having different dimensions to attach each of a plurality of syringes (equipped with mounting flanges) to the syringe interface. In that regard, each of the plurality of syringes has a different mounting flange dimension. Each of the plurality of syringe mount apertures is in general alignment with the axis of the plunger extension of the syringe loader (or other drive member).

Syringe 20 can, for example, be removably connected to syringe interface 700 generally as described in U.S. Pat. No. 5,383,858. In that regard, as best shown in FIG. 5E, syringe interface 700 can include a first mount or mount aperture 710 having a first opening 720 formed therein. Plunger extension 640 is reciprocally mounted within syringe loader 610 and is extendible through opening 720. Mount 710 includes receiving slots 722a and 722b, which are preferably positioned opposite one another around opening 720. Receiving flanges 724a and 724b are preferably positioned opposite one another and between receiving slots 722a and 722b and extend inwardly into opening 720.

To attach syringe 20 to syringe loader 610 (see FIG. 5C), the rearward end of syringe 20 is inserted into interface 700 (and first mount 710) such that mounting flanges 22a and 22b are inserted into receiving slots 722a and 722b, respectively. In one embodiment, flange 644 of plunger extension 640 preferably simultaneously aligns with and engages capture members 42 and 44 of syringe plunger 40 (as described above) when mounting flanges 22a and 22b are aligned with slots 722a and 722b.

Once mounting flanges 22a and 22b are inserted into receiving slots 722a and 722b, respectively, and plunger extension 640 is in position to be received by the syringe plunger, the operator rotates syringe 20 approximately 90 degrees such that mounting flanges 22a and 22b move behind and are engaged by receiving flanges 724a and 724b, respectively, and syringe plunger 40 is engaged by plunger extension 640. Syringe interface 700 may include one or more stop mechanisms such as, for example, abutment member 726a extending, for example, from at least one of the retaining flanges 724a and 724b, to prevent rotation of syringe 20 more than 90 degrees. Tactile, visual or audible feedback can be provided to the operator via, for example, cooperating members (not shown) on syringe 20 and syringe interface 700 to inform the operator that secure connection has been achieved. After securely attaching syringe 20 to syringe interface 700 (and thereby to syringe loader 610), advancing plunger extension 640 in a forward direction will apply a motive force to syringe plunger 40 to advance syringe plunger 40 forward within syringe 20, thereby forcing the contents of syringe 20 out of syringe tip 26. Retracting plunger extension 640 in a rearward direction will cause the syringe plunger to move rearward within syringe 20, thereby drawing fluid into syringe 20.

As best shown in FIGS. 5E and 5C, syringe interface 700 also includes at least a second mount or mount aperture 810 having an opening 820 formed therein that is larger than opening 720 and has generally the same center as opening 720. Plunger extension 640 is thus also extendible through opening 820 to cooperate with syringe plunger 40 as described above. Mount 810 includes receiving slots (only 822a is shown), which are preferably positioned opposite one another around opening 820. Retaining flanges 824a and 824b are preferably positioned opposite one another and between receiving slots 822a and 822b and extend inwardly into opening 820.

To attach a syringe 20' to syringe loader 610 (as shown in FIG. 5D), the rearward end of syringe 20' is inserted into injector opening 820 such that mounting flanges 22a' and 22b' are inserted into receiving slots 822a and 822b, respectively. The diameter/volume of syringe 20' is greater than the diameter of syringe 20. As syringe 20' is moved rearward, it contacts mount 710. Mount 710 is preferably movable (for example, slidable in an axial direction) such that mount 710 moves rearward when contacted by syringe 20'. Axial rearward movement of mount 710 allows syringe 20' to move rearward and, subsequently, to be rotated relative to mount 810 so that flanges 22a' and 22b' of syringe 20' are rotated into engagement with (i.e., behind) retaining flanges 824a and 824b, as described above for syringe 20 and retaining flanges 724a and 724b.

In one embodiment, mount 710 is attached to or formed integrally with a plate 850 that is slidably mounted on posts 860a and 860b via holes or passages 852a and 852b, respectively, formed in plate 850. Preferably, mount 710 is biased in a forward position as illustrated, for example, in FIG. 5C. In the embodiment of FIGS. 5A through 5I, springs 870a and 870b are positioned on posts 860a and 860b to bias mount 710 in a forward position. Springs 870a and 870b are retained on posts 860a and 860b by plate 850 and abutment elements 862a and 862b (see FIG. 5E) positioned on a rearward end of posts 860a and 860b, respectively.

Other syringe interfaces for attachment of syringes of various sizes are suitable for use in the present invention. As described in U.S. patent application Ser. No. 10/233,844, filed on Sep. 3, 2002, a syringe interface 890a (see FIG. 5H) suitable for use with the syringe loaders of the present invention can also include a plurality of syringe mounts 890aa, 890ab and 890ac that are fixed at different axial positions. Moreover, a syringe interface 890b can include a generally cone-shaped or frustum-shaped threaded flange 890ba to cooperate with a corresponding threaded flange on each of a plurality of syringes (each syringe size having a frustum-shaped threaded flange of a different diameter). The radius of threaded flange 890ba decreases as one moves rearward within the syringe interface. A syringe interface 890c can also include one or more retention members that are movable to adjust the radial position of retaining flanges formed on a radially inward end thereof to cooperate with and retain each of a plurality of syringes. For example, each retention member 890ca of the syringe interface 890c can be rotatable in a plane generally parallel to an axis of the syringe to adjust the radial position of retaining flanges 890cb.

Alternatively, each retention member 890da of a syringe interface 890d can alternatively be rotatable in a plane generally parallel to the radius of the syringe to adjust the radial position of retaining flanges 890db.

An example of the use of syringe loader 610 with a 65 ml syringe sold by Medrad, Inc, for use with its Spectris® MR injector is illustrated generally in FIG. 5I. In this example, the following steps are carried out:

1. First, unused, empty syringe 20 (or 20') is inserted into syringe interface 700 such that the drip flange 28 of syringe 20 is at the bottom/rear, and the graduations (if any) of syringe 20 are facing right. (When loading syringe 20', mount 710 moves down/rearward as described above.)
2. Syringe 20 is then rotated clockwise until it stops (approximately ¼ turn or 90°). The graduations on syringe 20 will now be facing forward.
3. Handle 652 of lever arm 650 is then rotated upward/forward until it stops, thereby advancing plunger 40 to its forward position within syringe 20.
4. Using an appropriate spike/connector, a saline, contrast medium or other injection fluid container 895 is connected to the tip 26 of syringe 20 (preferably using good sterile technique).
5. Handle 652 of lever arm 650 is then pulled downward/rearward until the desired amount of saline or contrast medium has entered syringe 20.
6. Container 895 is then disconnected from syringe 20.
7. Handle 652 of lever arm 650 is then preferably pulled fully downward/rearward until it stops.
8. Syringe 20 is rotated counterclockwise until it stops (approximately ¼ turn or 90°). (Syringe 20' may be pushed upward/forward upon disconnection as a result of the forward bias of plate 850).
9. Loaded syringe 20 may then be withdrawn from syringe loader 610.

At this point, syringe 20 can be capped (for example, with a cap/connector tube) using good sterile technique. Syringe 20 is preferably labeled to identify loaded medium.

Figure 5F:
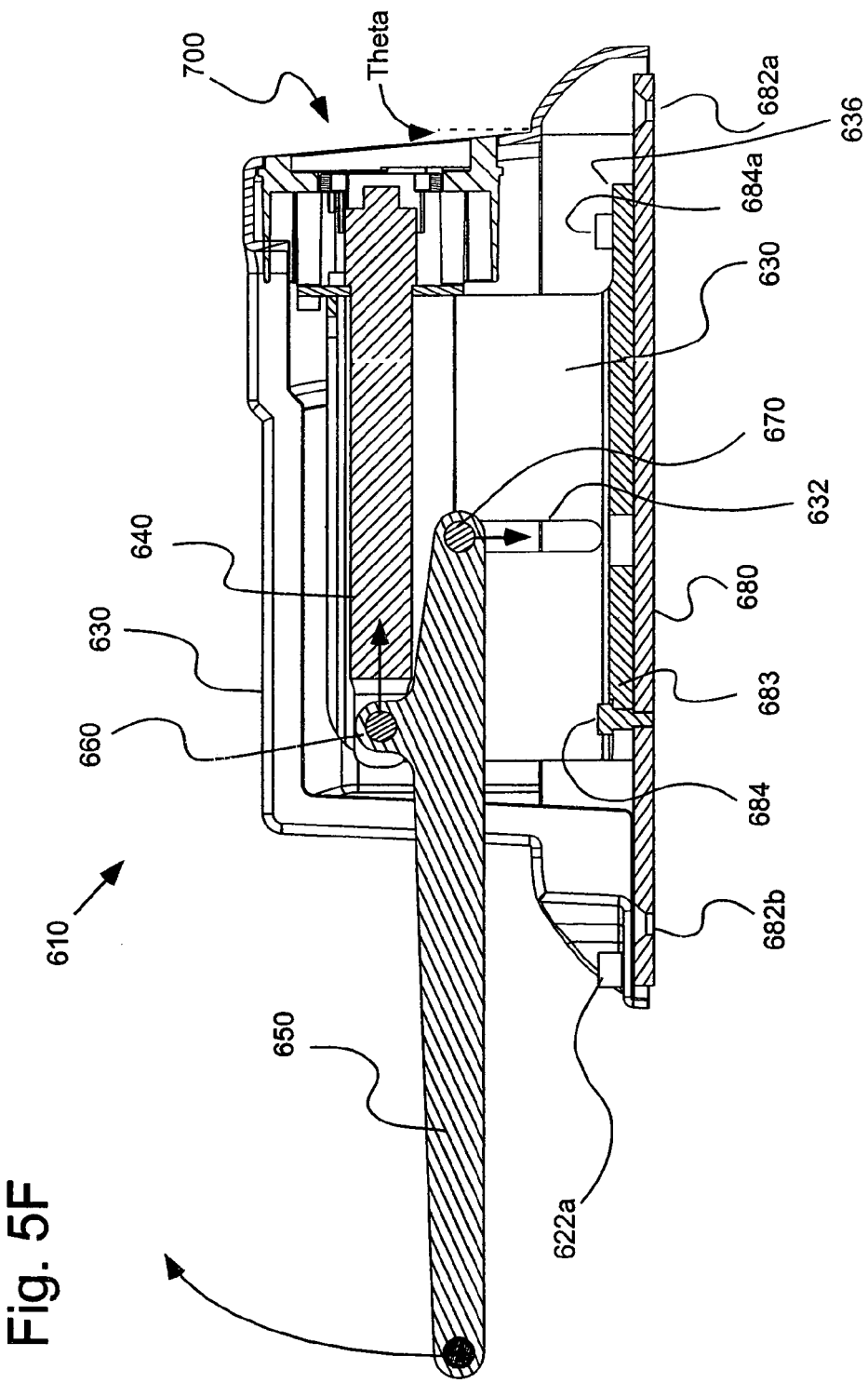
FIG. 5F is a side, cross-sectional view of the syringe loader of FIG. 5A.
Figure 5G:
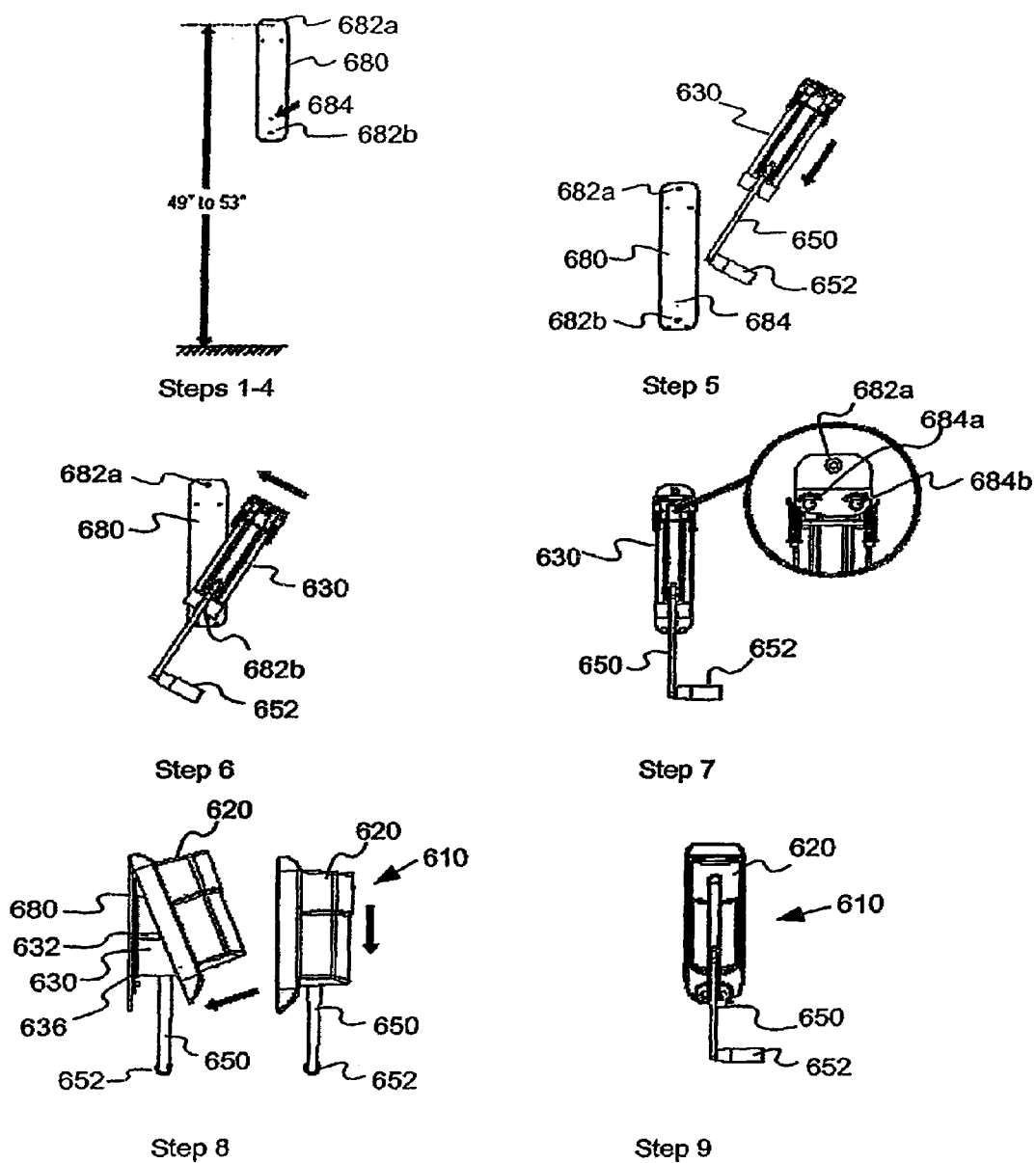
FIG. 5G is one embodiment of a process or method of mounting the syringe loader of FIG. 5A (in which the view of all steps other than step 8 is a top view; step 8 illustrates a side view)
Figure 5H:
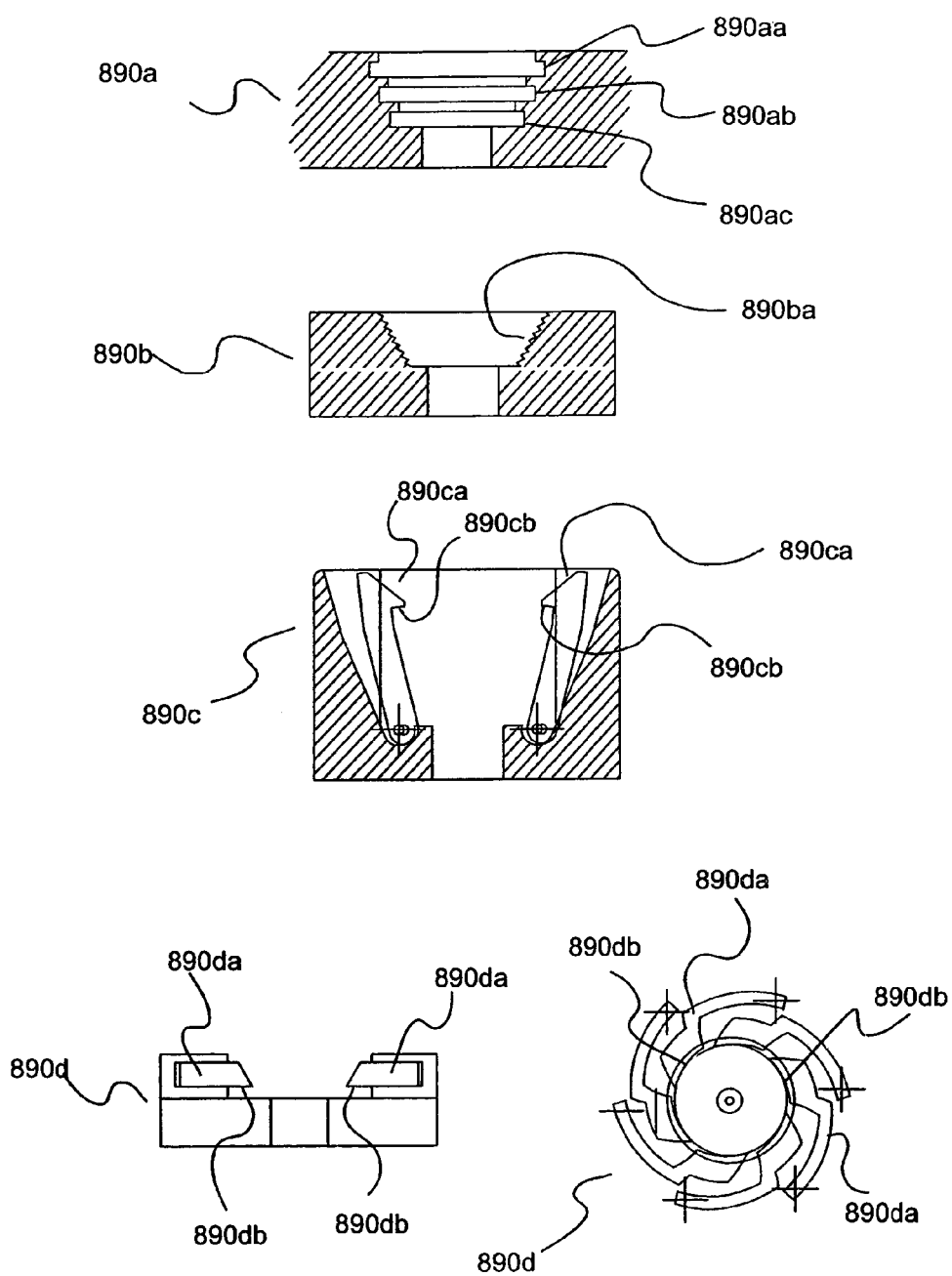
FIG. 5H illustrates several alternative embodiments of syringe interfaces suitable for use with the syringe loaders of the present invention.
Figure 51:
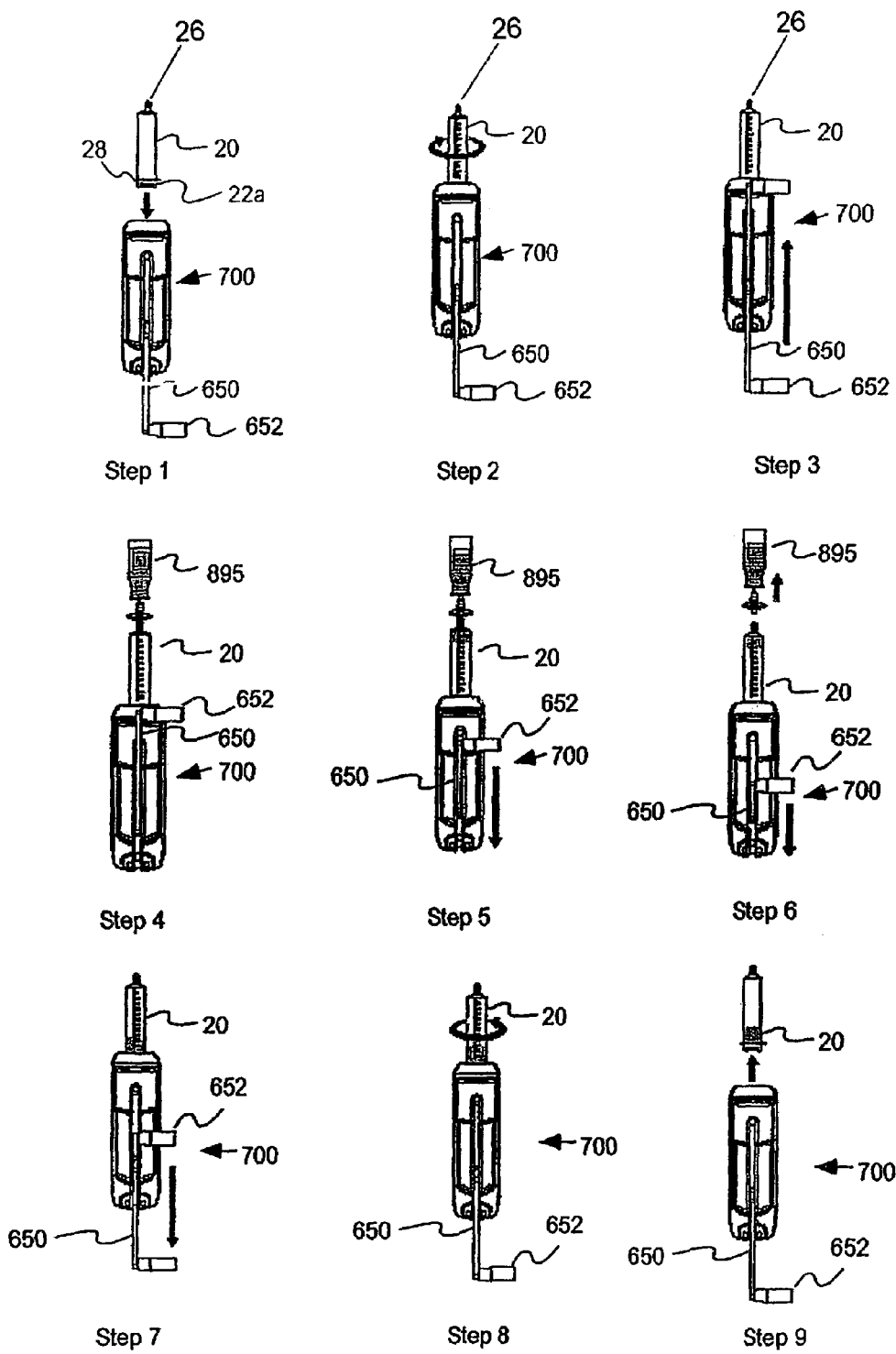

As best illustrated in, for example, FIG. 5F, a front face of syringe loader 610 and of syringe interface 700 can be angled at an angle Theta or θ from the vertical to facilitate runoff of spilled or leaked contrast (and/or other injection media) during a loading procedure as described above in connection with FIG. 5I (particularly when the syringe loader is mounted vertically on a wall). Spillage or leakage during loading of syringes is a common occurrence. Indeed, the syringe loaders of the present invention provide the benefit of eliminating the use of injectors to load empty syringes. Contrast media and other injection fluids can damage the internal components of powered injectors. Although to a much lesser extent, buildup of such injection fluids can also be detrimental to the syringe loaders of the present invention.

Figure 6A:
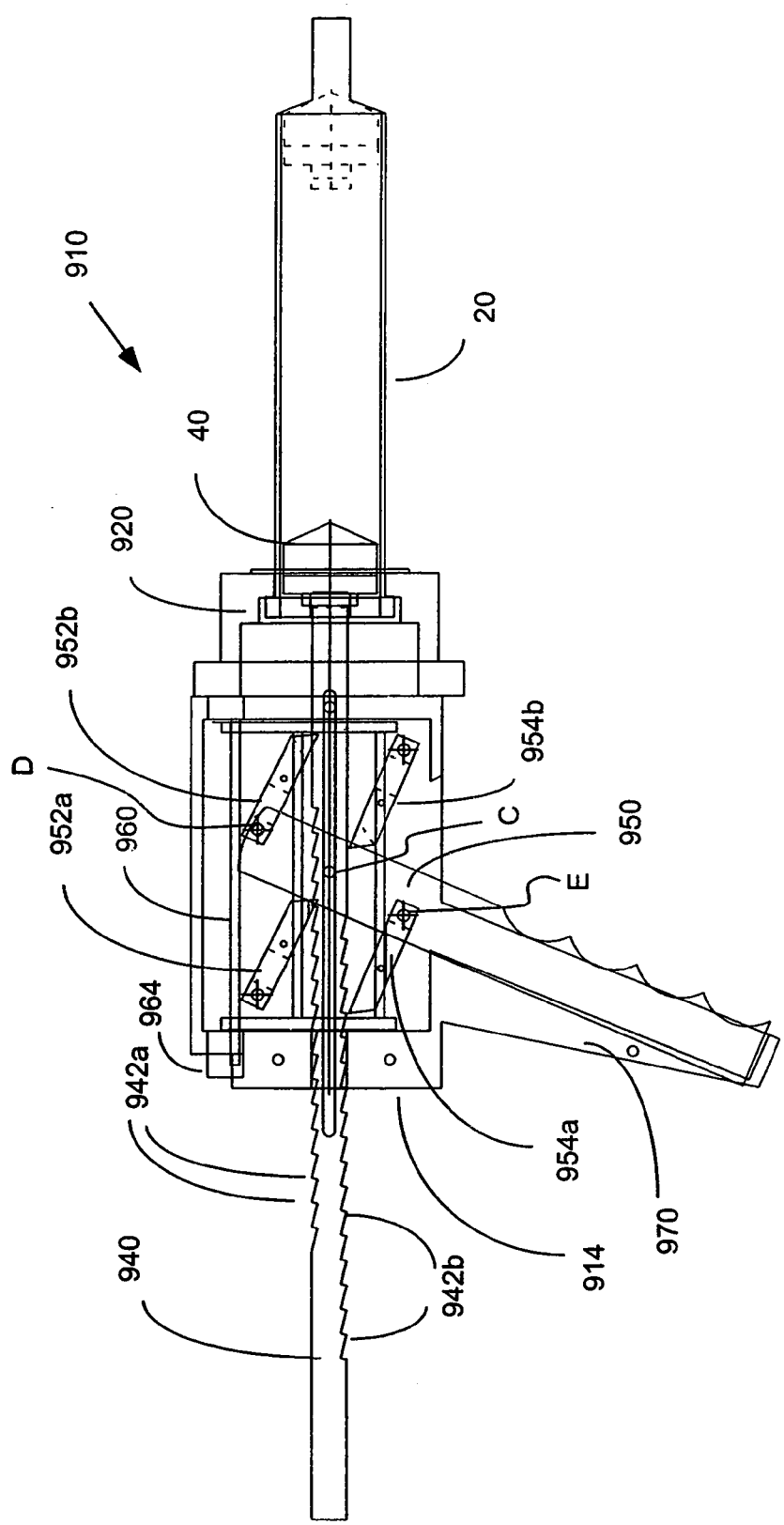
FIG. 6A is a side, cross-sectional view of another embodiment of a syringe loader of the present invention in which the syringe loader is set-up to advance the plunger.

FIGS. 6A and 6B illustrate another embodiment of an off-injector syringe loader 910. Syringe loader 910 includes a syringe mount 920 as described above. Syringe loader 910 also includes a plunger extension 940 that operates to impart motion to plunger 40. In this embodiment, plunger extension 940 includes ratchet teeth 942a on an upper side thereof and ratchet teeth 942b on a lower side thereof. Upper pawls 952a and 952b cooperate with upper ratchet teeth 942a to impart forward motion to plunger extension 940. Lower pawls 954a and 954b cooperate with lower ratchet teeth 942b to impart rearward motion to plunger extension 940. In that regard, a rotating grip handle 950 rotates about a point C within housing 914 of syringe loader 910. Pawl 952b is rotatably attached to handle 950 at a point D on a first side of (for example, in the orientation of FIG. 6A, above) point C, while pawl 954a is rotatably attached to handle 950 at a point E on a second side of (for example, in the orientation of FIG. 6A, below) point C.

The position of a carriage 960 is vertically adjustable (using, for example, an adjustment knob 964) to a first position (illustrated in FIG. 6A) to bring upper pawls 952a and 952b into operative connection with plunger extension 940 or to a second position (illustrated in the lower portion of FIG. 6B) to bring lower pawls 954a and 954b into operative connection with plunger extension 940. Pawls 952a, 952b, 954a and 954b are preferably biased towards an engagement position (using, for example springs) as known in the mechanical arts unless prevented therefrom by carriage 960. Pawls 952a and 954b preferably are not provided motive force by rotation of handle 950, but are present to help ensure that plunger extension 940 does not move in a direction other than as determined by the position of carriage 960.

FIG. 6B illustrates the use of rotating handle 950 to expel and load injection fluid into a syringe. Depending on the position of carriage 960, the same pumping, gripping motion can either advance plunger extension 940 or retract plunger extension 940, as illustrated in FIG. 6B. Syringe loader 910 includes a stationary grip handle 970 that is gripped by the thumb of the user's hand. During use of syringe loader 910, the user grips rotating handle 950 with the finger tips of the same hand and either advances or retracts plunger 40 (depending on the position of carriage 960) by alternatively closing and opening and gripping handle 950, similar to the motion used with common caulking guns. Rotating handle 950 is preferably biased in an "open" position (using, for example a spring (not shown)) with the lower end thereof rotated away from stationary handle 970, as illustrated in the left-hand portion of FIG. 6B.

Figure 7A:
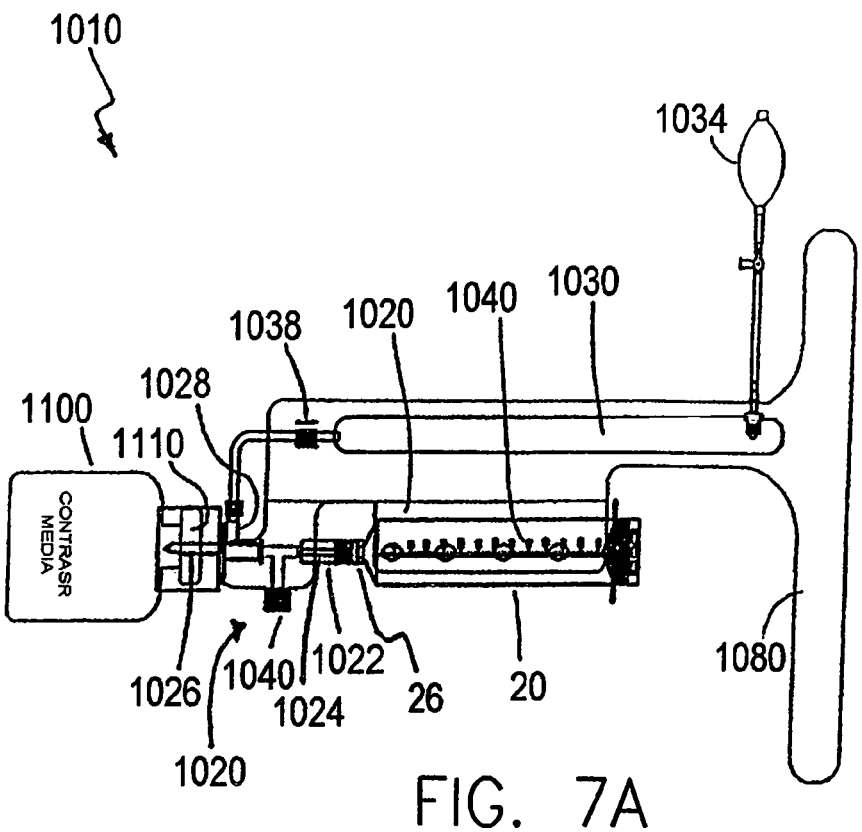
FIG. 7A is a front view of another embodiment of a syringe loader of the present invention in which the syringe loader is wall-mountable.
Figure 7B:
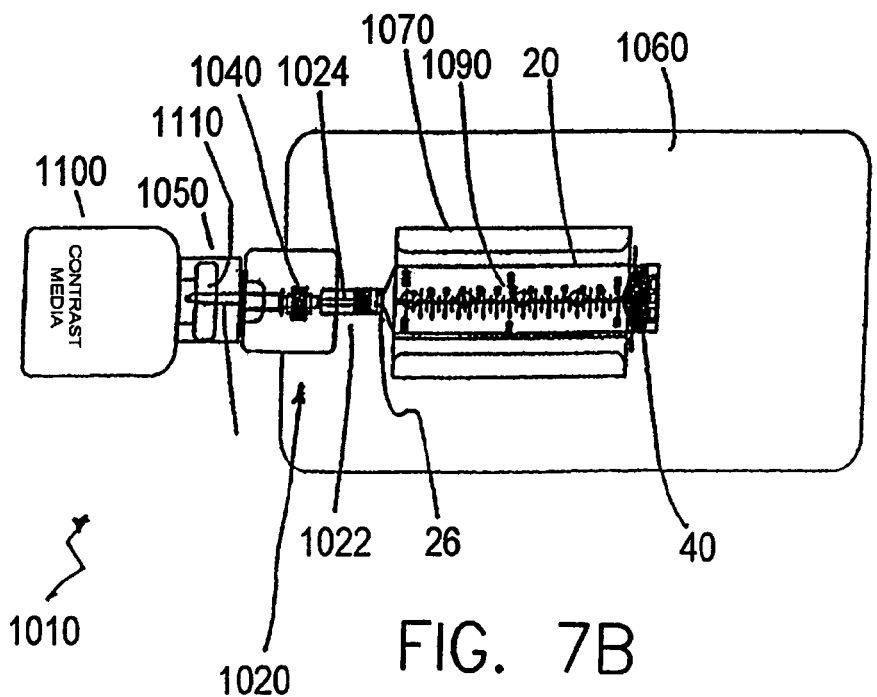
FIG. 7B is a side view of an embodiment of a syringe loader similar in operation to the syringe loader of FIG. 7A except that the syringe loader includes a stand to support the syringe loader on a surface.
Figure 7C:
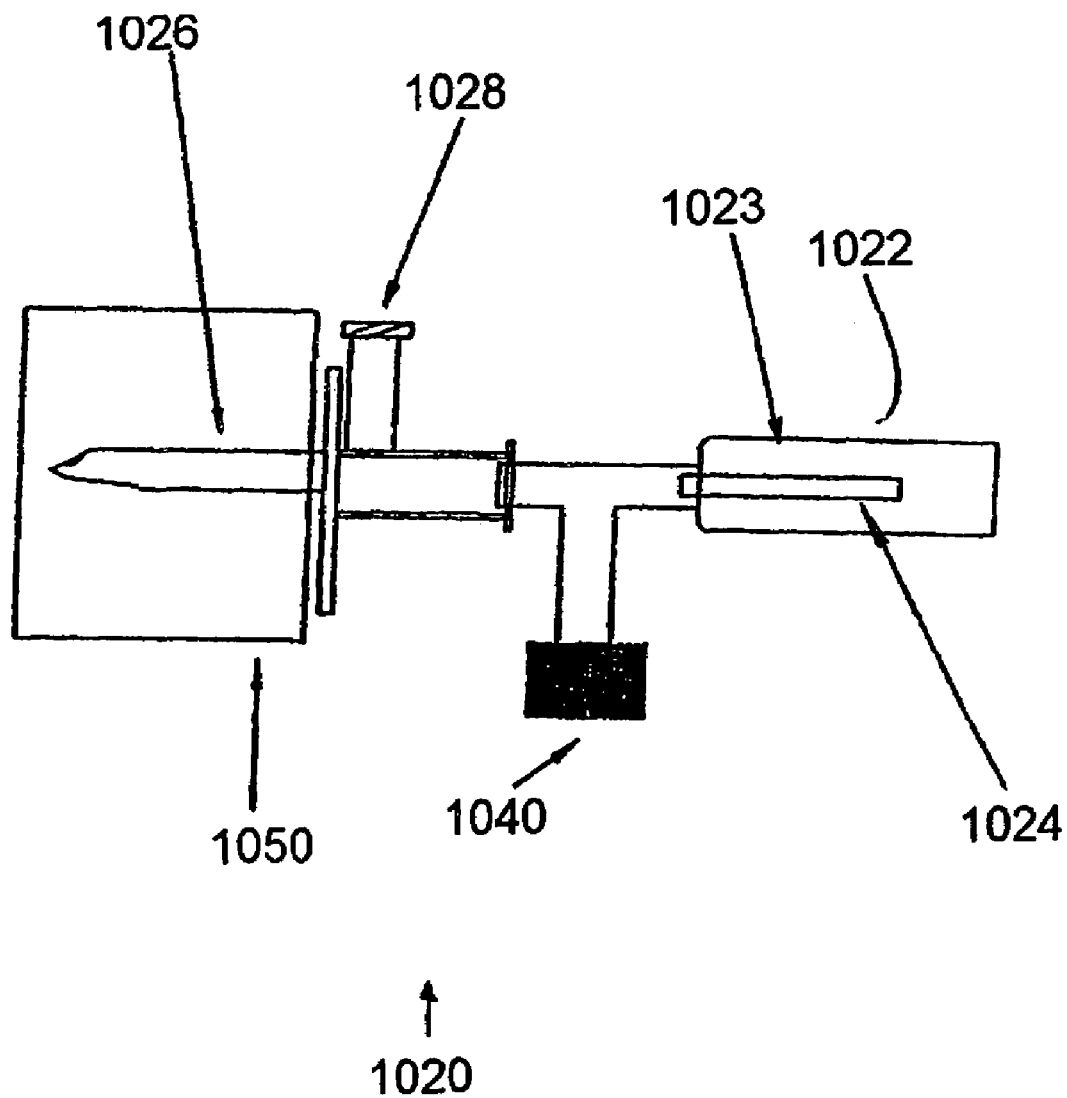
FIG. 7C is a side view of the connector of the syringe loaders of FIGS. 7A and 7B.

FIGS. 7A through 7C illustrate an embodiment of an off-injector syringe loader in which gas pressure is used to force injection fluid into syringe 20. In this embodiment, syringe loader 1010 does not attach to a rear mounting mechanism of a syringe (for example, flanges 22a and 22b of syringe 20) as described above for syringe loaders 310, 410, 510, 510', 610 and 910. Instead, syringe loader 1010 includes a connector 1020 that connects a source of injection fluid (for example, contrast media bottle 1100) with syringe 20. Connector 1020 includes a connection mechanism 1022 on one end thereof to connect to syringe tip 26. Connection mechanism 1022 can, for example, include a luer connection as known in the medical arts. Conduit or passage 1024 of connector 1020 is brought into fluid connection with the interior of syringe 20 when connector 1020 is attached to, for example, syringe 20 or syringe 250. Connector 1020 is readily modifiable to attach to virtually any syringe design. A second connection mechanism 1026 is positioned on another end of connector 1020. In the embodiment of FIGS. 7A through 7C, connection mechanism 1026 includes a spike for connecting connector 1020 to contrast bottle 1100, which includes a septum 1110.

Connector 1020 includes a passage therethrough to place contrast bottle 1100 and syringe 20 in fluid connection when both are connected to connector 1020. Connector 1020 also includes an inlet 1028 to permit a pressurized gas to enter contrast bottle 1100. In one embodiment, pressurized air is used via connection of inlet 1028 to an air bladder 1030 that is in fluid connection with, for example, a ball pump 1034 to pressurize air. Preferably, a check valve 1038 is placed between air bladder 1030 and inlet 1028 to substantially prevent flow of air from inlet 1028 to air bladder 1030. Connector 1020 also preferably includes a valve such as a push valve 1040 that is closed during pressurization of contrast bottle 1100 via air bladder 1030 and ball pump 1034 to prevent air from passing into syringe 20. Once contrast bottle 1100 is sufficiently pressurized by pumping air therein, push valve 1040 is opened to allow pressurized contrast medium to flow into syringe 20 via conduit 1024.

Contrast bottle 1100 is preferably in a generally inverted position as illustrated in FIGS. 7A and 7B during the loading process to ensure that the pressurized gas (for example, air) rises to the bottom of contrast bottle 1100 and above the spike to prevent gas from passing into syringe 20. Moreover, the inverted orientation of contrast bottle 1100 allows gravity to assist in the filling of syringe 20. The top (that is, the opening) of inverted contrast bottle 1100 can, for example, rest within a generally cylindrical retainer or support 1050 provided on connector 1020 during the loading process.

Preferably, connection mechanism 1022 includes an outer portion 1023 that passes over syringe tip 26 during connection of connector 1020 to syringe 20. Conduit 1024 is preferably housed within outer portion 1023 such that conduit 1024 does not extend outside of (that is, beyond the lower edge of) outer portion 1023 to assist in preventing contaminants from contacting conduit 1024 (for example, during connection of connector 1020 to syringe 20), thereby assisting in maintaining the sterility of syringe 20.

In the embodiment of FIG. 7A, syringe loader 1010 is attached to a mounting base 1060 that is preferably adapted to mount syringe loader 1010 to a wall. A syringe retainer 1070 is attached to mounting base 1060 to retain syringe 20 during loading. In the embodiment of FIG. 7B, syringe loader 1020 is attached to a standing base unit 1080. Syringe retainer 1070 is attached to standing base unit 1080. Gradation members 1090 that are syringe dependent can be provided to assist in loading a desired amount of fluid into syringe 20.

Figure 9:
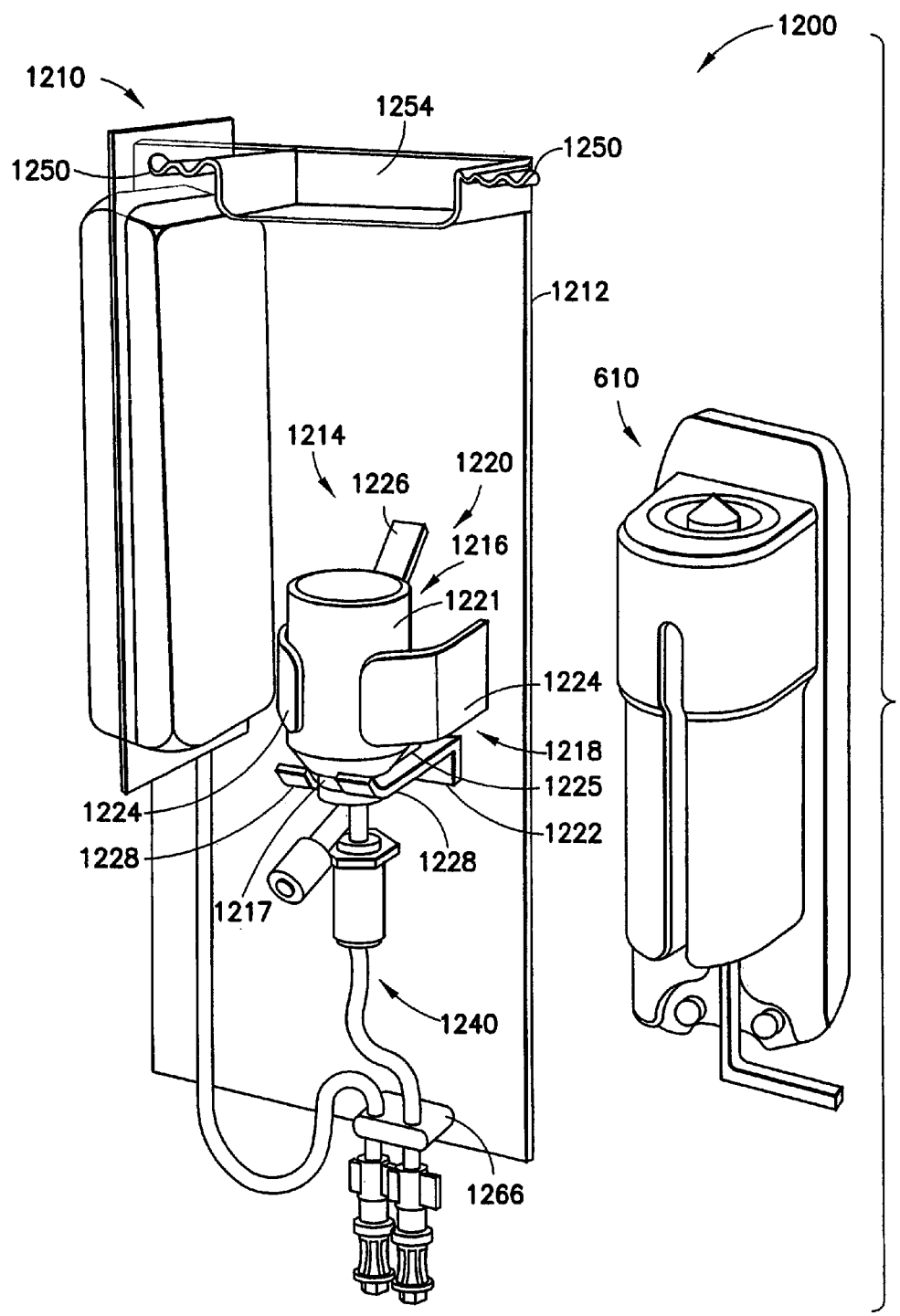
FIG. 9 is a perspective of the syringe loading system of FIG. 8 illustrating an alternative mounting position for the fill station.

Referring to FIGS. 8 and 9, a medical container loading system 1200 in accordance with the present invention is illustrated. The medical container loading system 1200 generally includes one of the loading devices or loaders 310–610, 910, 1010, for example syringe loader 610, discussed previously in connection with FIGS. 3–7, and a fill system or station 1210. Preferably, the loading system 1200 includes the wall-mounted loader 610. The fill station 1210 is also preferably wall-mounted, for example by mechanical fasteners, and located proximate to the loader 610. Preferably, the fill station 1210 is wall-mounted above the loader 610. However, the loader 610 and fill station 1210 may be positioned side-by-side as shown in FIG. 9. Generally, the top of the loader 610 is intended to be located approximately 35–45 inches above floor level. The bottom of the fill station 1210 is located approximately 50–60 inches above floor level. The placement of the loader 610 and fill station 1210 at the height dimensions indicated provide convenient and safe height locations for both short and tall users of the syringe loading system 1210.

Figure 10:
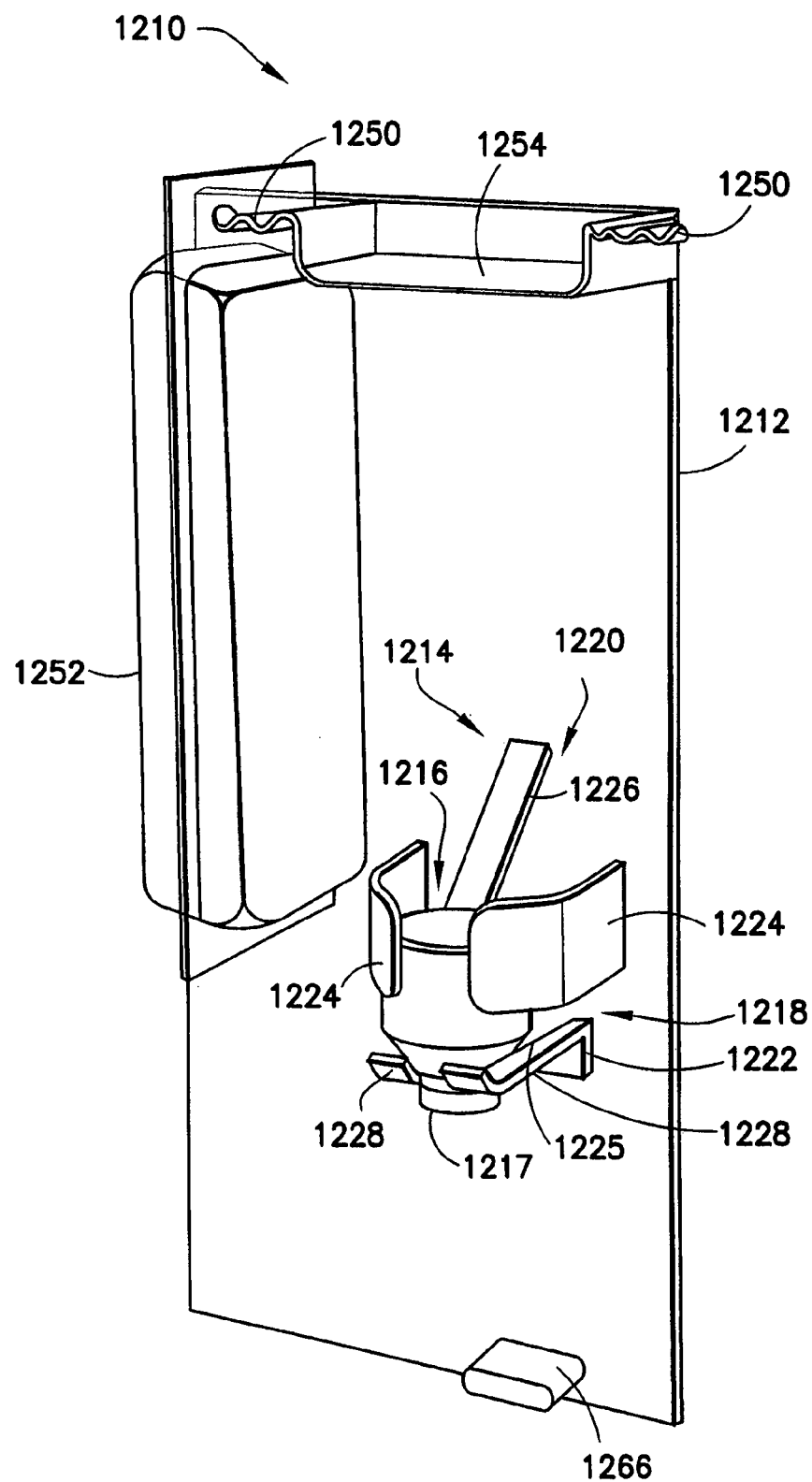
FIG. 10 is a perspective view of the fill station shown in FIG. 8.

FIGS. 8–10 illustrate an embodiment of the fill station 1210 adapted for use with the loader 610. The fill station 1210 is generally comprised of a mounting plate 1212 and a holding assembly 1214 connected to the mounting plate 1212. The mounting plate 1212 is rectangular-shaped and is preferably configured to be wall-mounted. The mounting plate 1212 may also be configured to be mounted on a movable stand, such as an IV pole. In such an arrangement, the mounting plate 1212 could be mounted on the IV pole to be height-adjustable.

The holding assembly 1214 is connected to the mounting plate 1212 and is adapted to support a medical fluid container 1216 as illustrated. The medical fluid container 1216 will typically be filled with medical fluid, which may be used, for example, in a medical imaging procedure such as a CT procedure. The body of the medical fluid container 1216 narrows to a neck 1217, which is customary in the field of solid medical fluid containers. The holding assembly 1214 is comprised of at least one fixed support 1218 connected to the mounting plate 1212 and at least one movable support 1220 also connected to the mounting plate 1212, but typically located above the fixed support 1218. The fixed support 1218 and movable support 1220 generally coact with a body 1221 of the fluid container 1216 to maintain the medical fluid container 1216 in the holding assembly 1214. The fill station 1210 may comprise multiple holding assemblies 1214 for supporting multiple fluid containers 1216 in accordance with the present invention.

In the holding assembly 1214, the fixed support 1218 includes a U-shaped bracket 1222 connected to the mounting plate 1212 and a pair of support arms 1224 connected to the mounting plate 1212 generally above the U-shaped bracket 1222. The U-shaped bracket 1222 is generally sized to receive the neck 1217 of the medical fluid container 1216. In particular, a central opening 1225 defined by the U-shaped bracket 1222 is formed to receive the neck 1217 of the most common sizes of fluid containers 1216 used in the medical field.

The U-shaped bracket 1222 may be attached to the mounting plate 1212 by conventional mechanical fasteners formed integrally with the mounting plate 1212, or attached to the mounting plate 1212 by other means, such as by adhesive. The support arms 1224 may be attached by similar attachment methods to the mounting plate 1212. Preferably, the fixed support arms 1224 are curved to conform to the cylindrical shape of the body 1221 of the medical fluid container 1216, which is typical in the art.

The movable support 1220 is preferably comprised of a resiliently biased movable support arm 1226. The movable support arm 1226 is configured to contact the body 1221 of the medical fluid container 1216 when the medical fluid container 1216 is placed in the holding assembly 1214. More particularly, the medical fluid container 1216 is placed in the holding assembly 1214 by positioning the neck 1217 of the medical fluid container 1216 in the central opening 1225 defined by the U-shaped bracket 1222. The central opening 1225 is defined by legs 1228 of the U-shaped bracket 1222, which support the medical fluid container 1216 in the vertical direction. The medical fluid container 1216 is supported in lateral directions by the two fixed support arms 1224. The movable support arm 1226 is preferably spring-biased outward from the face of the mounting plate 1212, for example by a compression spring, to contact the body 1221 of the medical fluid container 1216. The spring-biased movable support arm 1226 biases the medical fluid container 1216 into contact with the fluid support arms 1224.

Figure 11:
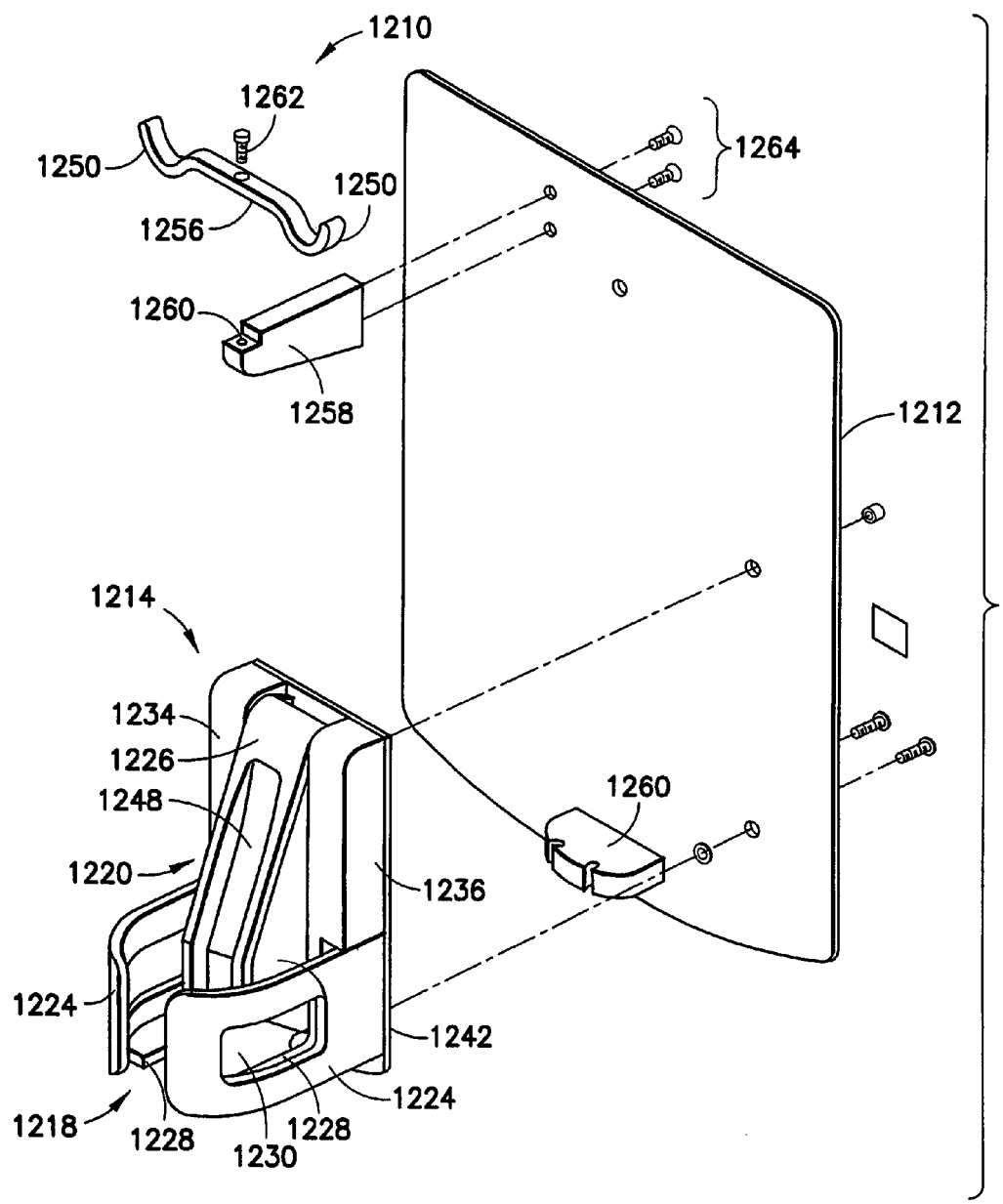
FIG. 11 is an exploded perspective view of another embodiment of a fill station adapted for use in the syringe loading system of FIGS. 8 and 9.
Figure 12:
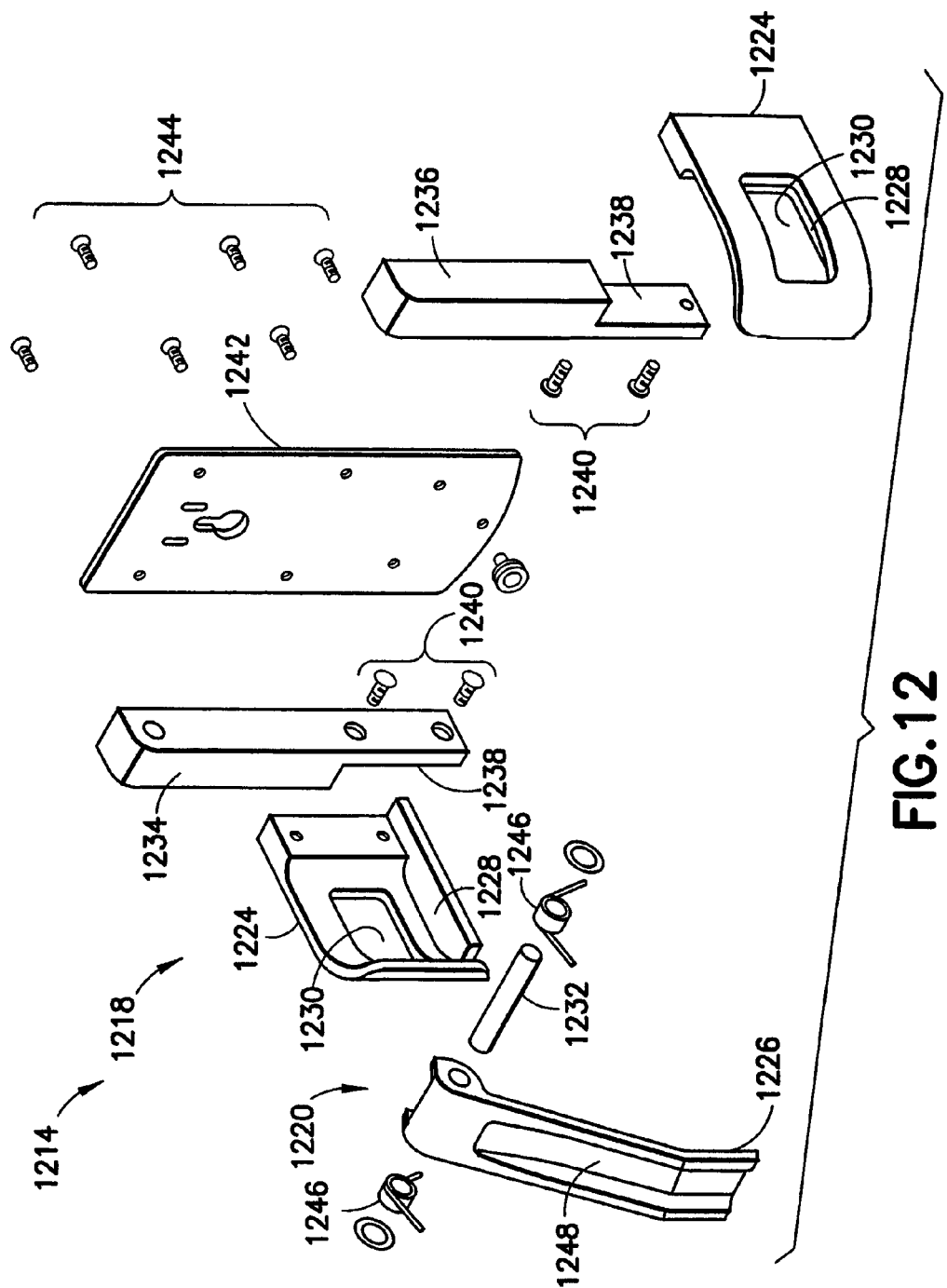
FIG. 12 is an exploded perspective view of a holding assembly of the fill station shown in FIG. 11.

Referring to FIGS. 11 and 12, the holding assembly 1214 may also be constructed as a singular or modular unit adapted to be attached to the mounting plate 1212. The holding assembly 1214 of FIGS. 11 and 12 essentially combines the U-shaped bracket 1222 with the fixed support arms 1224 in the fixed support 1218. In particular, the legs 1228 of the U-shaped bracket 1222 are preferably formed integrally with the curved fixed support arms 1224, respectively, so that the fixed support arms 1224 support both the body 1221 of the medical fluid container 1216 and the neck 1217 of the medical fluid container 1216, as illustrated. Additionally, the fixed support arms 1224 may be formed with openings or apertures 1230 to further facilitate viewing of the medical fluid container 1216 and the contents therein when loaded in the holding assembly 1214.

FIGS. 11 and 12 further show the holding assembly 1214 and the details of the movable support arm 1226. As the stated, the holding assembly 1214 of FIGS. 11 and 12 is provided as a singular or modular unit and is attached to the mounting plate 1212. The movable support arm 1226 is provided as part of the singular or modular holding assembly 1214. The movable support arm 1226 is pivotally supported on a pivot pin 1232. The pivot pin 1232 extends between two support members or columns 1234, 1236, which are oriented substantially parallel to one another. The support members 1234, 1236 each define a recess 1238 configured to receive the fixed support arms 1224 as shown in FIG. 11. The fixed support arms 1224 are connected fixedly to the respective support members 1234, 1236 by conventional means such as with mechanical fasteners 1240. The support members 1234, 1236 are further connected to a mounting or base plate 1242, which serves to support the support members 1234, 1236 that in turn support the movable support arm 1226 and the fixed support arms 1224. The mounting plate 1242 is connected to the mounting plate 1212 of the fill station 1210 by conventional mechanical fasteners 1244 as illustrated in FIG. 12. The mounting plate 1242 serves as a common mounting location for the support members 1234, 1236, movable support member 1226, and the fixed support members 1224, thereby making the holding assembly 1214 illustrated into a singular unit or component that may be attached in one step to the mounting plate 1212 of the fill station 1210.

Additionally, as shown in FIG. 12, a pair of torsion springs 1246 are received on the pivot pin 1232 and are adapted to bias the movable support arm 1226 outward from the mounting plate 1242 and, further, the mounting plate 1212 of the fill station 1210, generally. The movable support arm 1226 further defines a central recess 1248 that preferably extends substantially the length of the movable support arm 1226. The central recess 1248 is formed to cooperate with the rounded, cylindrical shape of the body 1221 of the medical fluid container 1216 to be supported in the holding assembly 1214.

The mounting plate 1212 and the elements of the fixed support 1218 and movable support 1220 are preferably formed of plastic and, more preferably, a medical grade plastic. In particular, the fixed support arms 1224, movable support arm 1226, support members 1234, 1236, and mounting plate 1242 are preferably made of plastic. The pivot pin 1232 and torsion springs 1246 may be made of metal, such as stainless steel, that is resistant to corrosion. The U-shaped bracket 1222 shown in FIGS. 8–10 may also be made of plastic, preferably a medical grade plastic.

Referring to FIGS. 8–12, the medical fluid container 1216 is loaded into the holding assembly 1214 by the following procedure. The medical fluid container 1216 is loaded by a user of the fill station 1210 by placing the body 1221 of the medical fluid container 1216 in contact with the movable support arm 1226. The movable support arm 1226 is biased to an engaged or extended position and the user must overcome the biasing force of the movable support arm 1226 to insert the body 1221 of the medical fluid container 1216 between the fixed support arms 1224. The body 1221 of the medical fluid container 1216 will further cooperate with the recess 1248 formed in the movable support arm 1226. As the user further inserts the medical fluid container 1216 into the holding assembly 1214, the neck 1217 of the medical fluid container 1216 is received between the legs 1228 of the fixed support arms 1224. Thus, the body 1221 of the medical fluid container 1216 is generally used to depress the movable support arm 1226 to provide sufficient clearance for the medical fluid container 1216 to "drop" into engagement between the fixed support arms 1224, with the neck 1217 of the fluid container 1216 received between the legs 1228 of the fixed support arms 1224. The movable support arm 1226, the fixed support arms 1224, and the legs 1228 of the fixed support arms 1224 co-act with the medical fluid container 1216 to maintain the medical fluid container 1216 in the holding assembly 1214. The medical fluid container 1216 may be connected to the syringe 20 used in the loader 610 in accordance with the methods discussed previously.

Preferably, one or more hook members 1250 for supporting one or more medical fluid containers/bags 1252 such as IV bags are mounted to the mounting plate 1212. The medical fluid bags 1252 may contain, for example, saline, therapeutic drugs and the like. The mounting plate 1212 preferably extends behind the medical fluid bags 1252. In the fill station 1210 depicted in FIGS. 8–10, a shelf 1254 may extend between the hook members 1250. The shelf 1254 may be located anywhere between the holding assembly 1214 and the top edge of the mounting plate 1212. The shelf 1254 may be formed integrally with the hook members 1250. Additionally, the hook members 1250 and shelf 1254 may be formed integrally with the mounting plate 1212. The hook members 1250 and shelf 1254 may also be connected to the mounting plate 1212 by conventional mechanical fasteners or by adhesive.

Additionally, as shown in FIGS. 11 and 12, the hook members 1250 may be connected or integrally formed together and mounted to the mounting plate 1212. The hook members 1250 are connected by a connecting member or bar 1256. The connecting member 1256 is preferably mounted to a support base 1258, which is in turn connected to the mounting plate 1212. The base 1258 defines a recess 1260 that receives the connecting member 1256 extending between the hook members 1250. A mechanical fastener 1262 and/or an adhesive may be used to secure the connecting member 1256 in the recess 1260. Similarly, conventional mechanical fasteners 1264 may be used to mount the support base 1258 to the mounting plate 1212.

Figure 18:
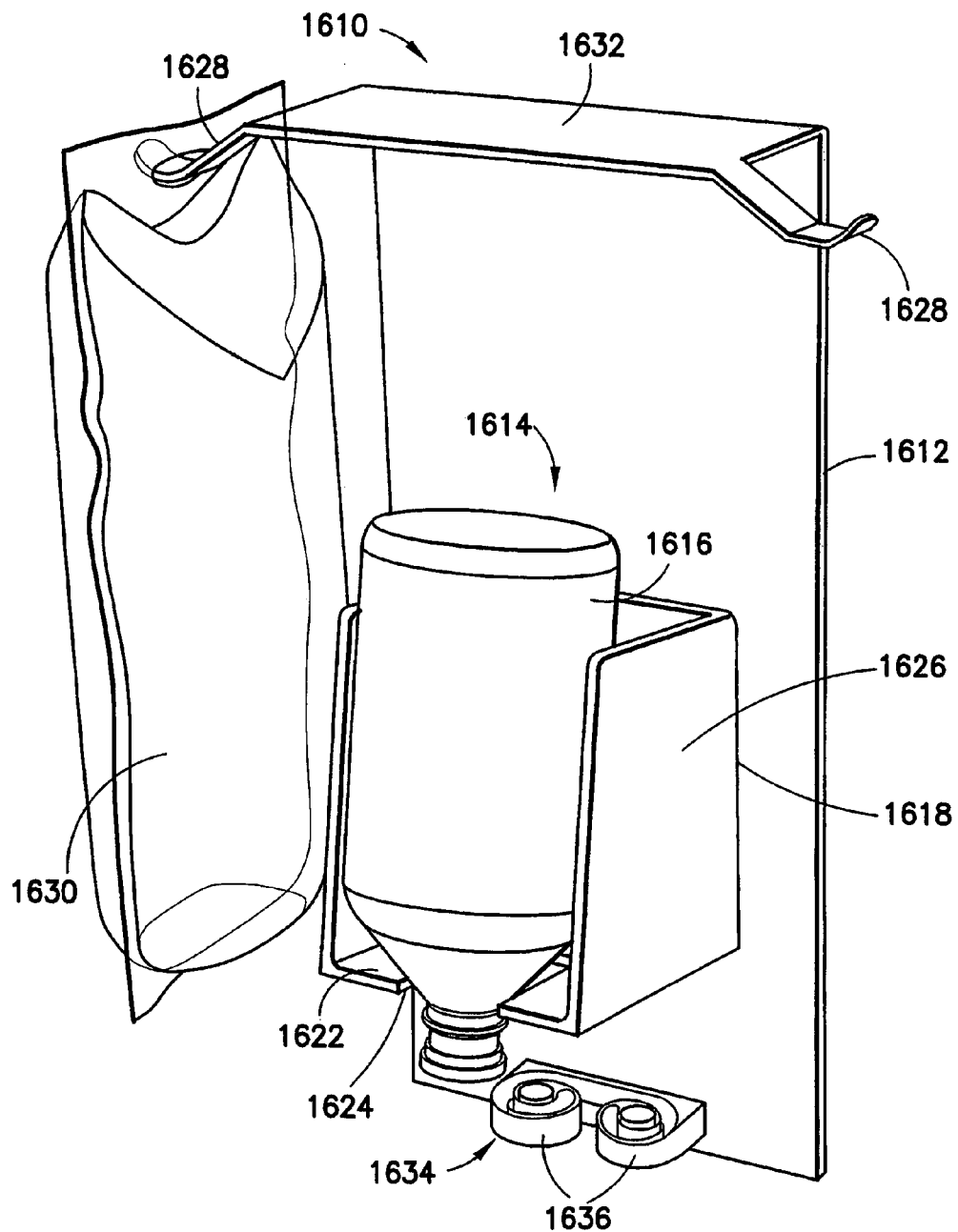
FIG. 18 is a perspective view of yet another embodiment of a fill station adapted for use in the syringe loading system of FIGS. 8 and 9.
Figure 19:
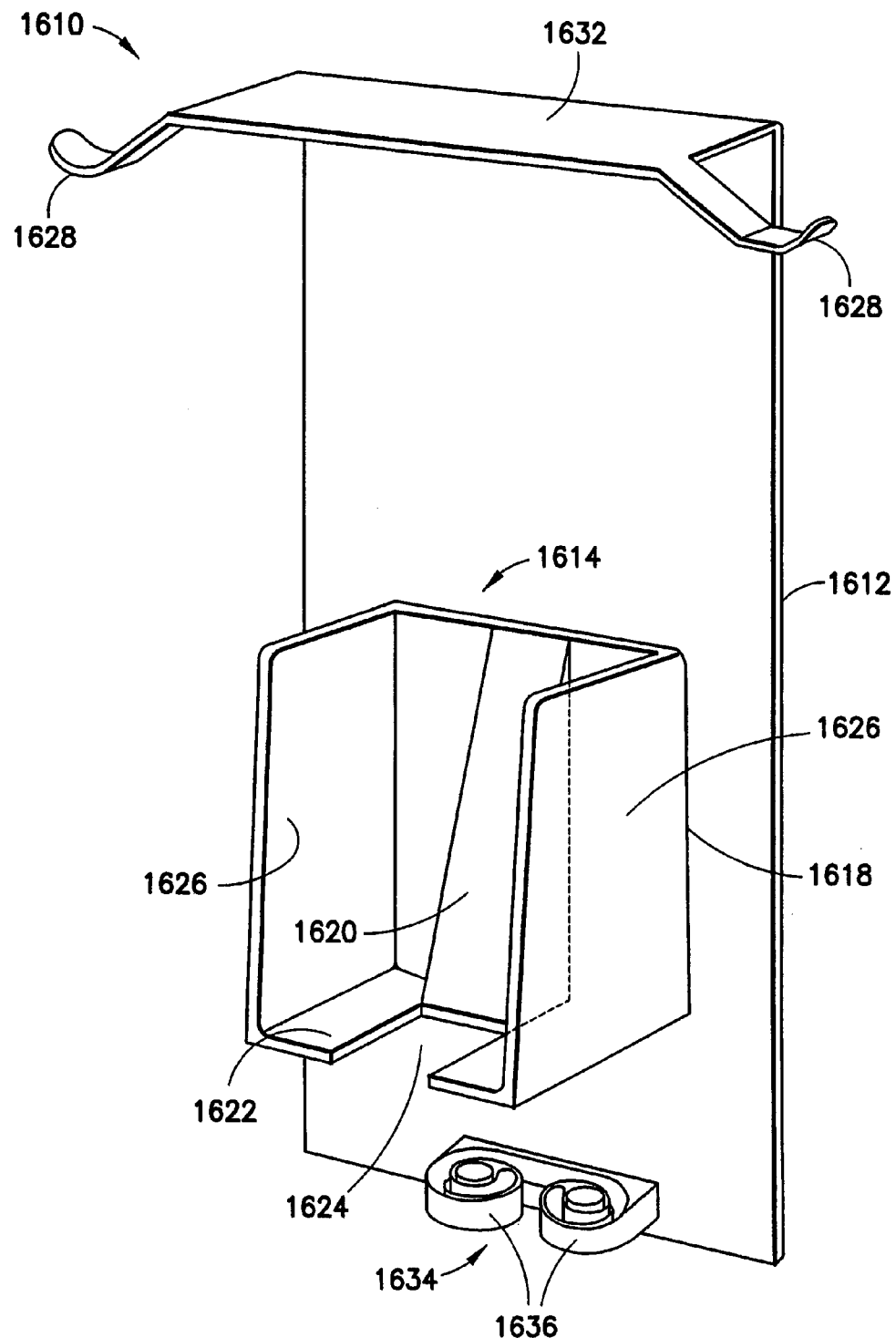
FIG. 19 is a perspective view of the fill station of FIG. 18, with the fluid container illustrated in FIG. 18 removed for clarity.
Figure 20:
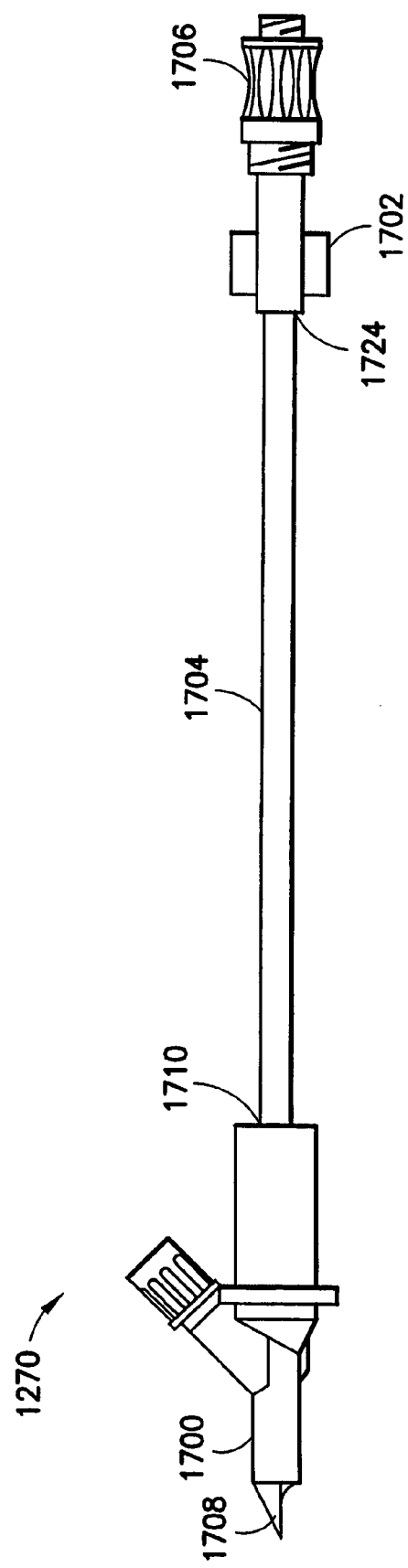
FIG. 20 is a side view of a fluid transfer set of the present invention used to connect a medical container associated with the loading devices of FIGS. 3-7 and medical fluid container associated with the various embodiments of the fill station shown in FIGS. 8-19.

A retaining clip 1266 may be connected to the mounting plate 1212 for restraining fluid transfer tubing that may be used to connect the medical fluid container 1216 and/or medical fluid bag(s) 1252 to the syringe 20 or other medical container used in the loader 610. The retaining clip 1266 is preferably located along the bottom edge of the mounting plate 1212 and centered below the holding assembly 1214. As discussed in detail herein, the present invention is further directed to a fluid transfer set 1270, which is preferably used to connect the medical fluid container 1216 to the syringe 20 or other medical container used in the loader 610. The retaining clip 1266 may be conventional in the art. An alternative configuration of the retaining clip 1266 is shown in FIGS. 18 and 19, wherein the retaining clip 1266 is formed with two coils that are adapted to restrain the tubing of the fluid transfer set 1270. The retaining clip 1266 may be made of plastic and affixed to the mounting plate 1212 by mechanical methods (i.e., fasteners) or by an adhesive.

Figure 13:
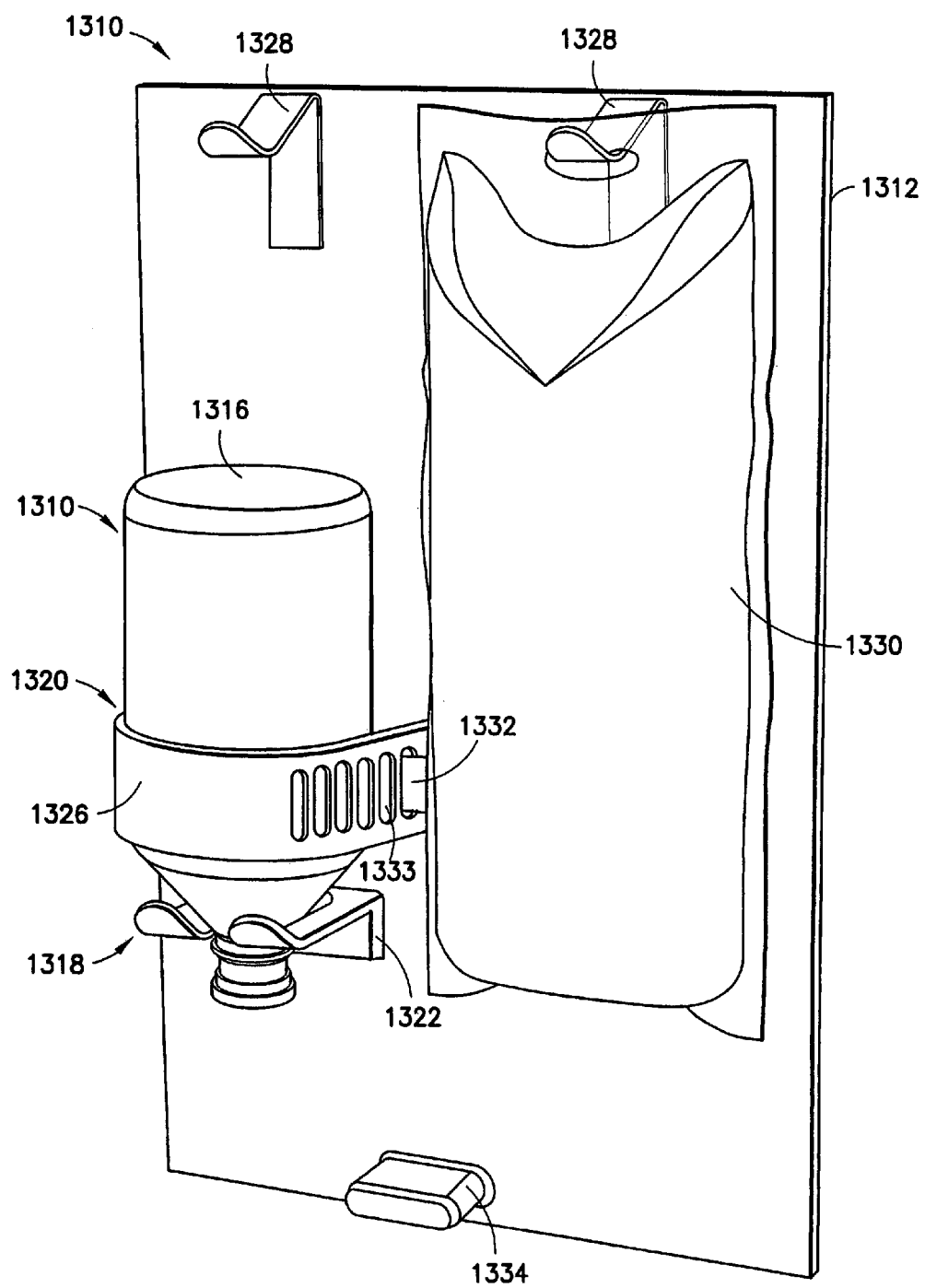
FIG. 13 is a perspective view of another embodiment of a fill station adapted for use in the syringe loading system of FIGS. 8 and 9.
Figure 14:
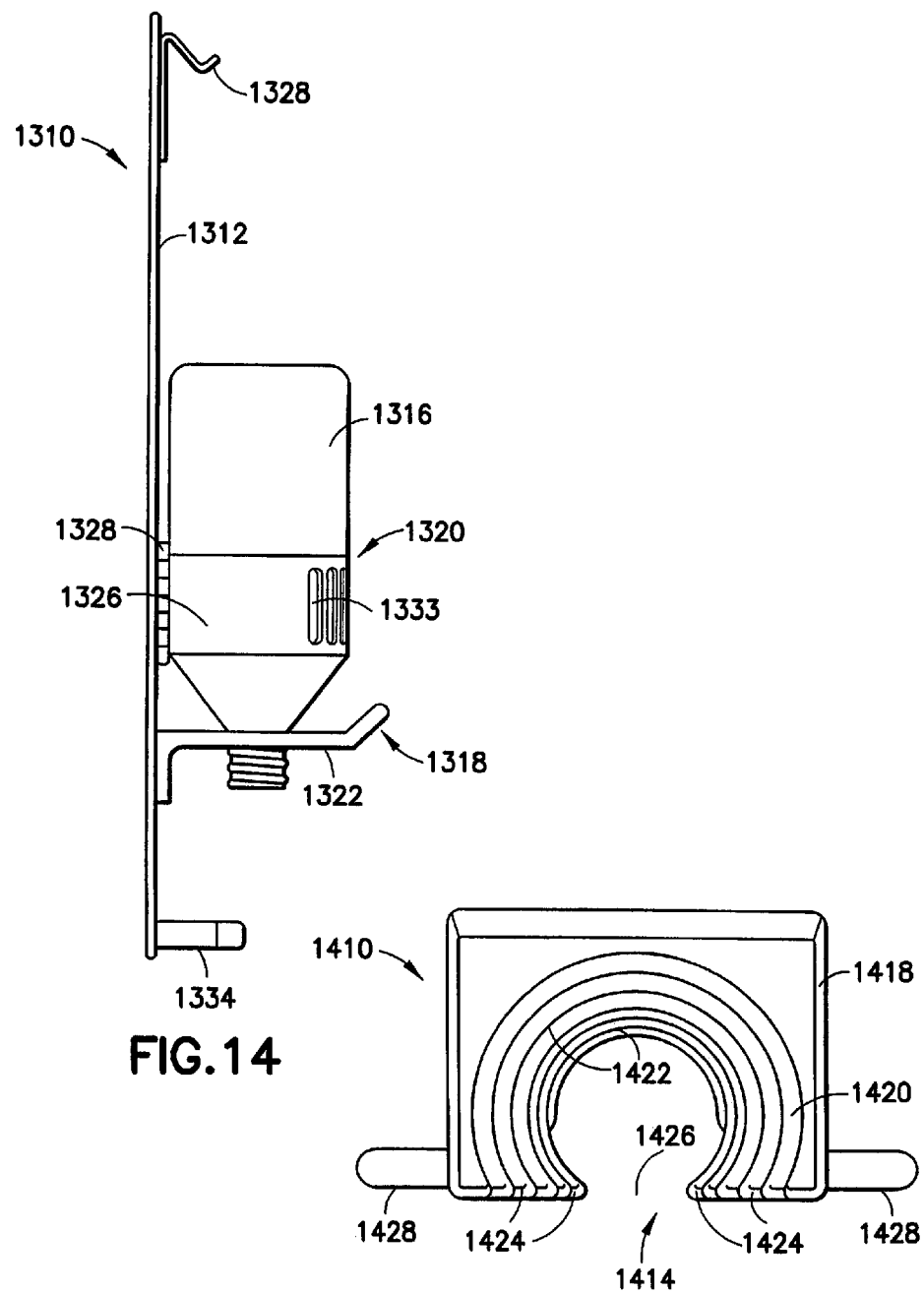
FIG. 14 is a side view of the fill station shown in FIG. 13.

Referring to FIGS. 13 and 14, another embodiment of a fill station 1310 adapted for use in the loading system 1200 of FIGS. 8 and 9 is shown. The fill station 1310 includes a mounting plate 1312 and a holding assembly 1314 that supports a medical fluid container 1316. The holding assembly 1314 is also comprised of a fixed support 1318 and a movable support 1320. The fixed support 1318 includes a U-shaped bracket 1322 connected to mounting plate 1312. Any of the mounting methods discussed previously in connection with the fixed support 1218 may be used to attach the fixed support 1318 to the mounting plate 1312. The movable support 1320 includes an adjustable strap 1326, which is preferably hingedly connected to the mounting plate 1312 as shown in FIG. 14. In particular, the adjustable strap 1326 is connected by a hinge 1328 to the mounting plate 1312. The mounting plate 1312 has two hook members 1328 located at the top edge or end of the mounting plate 1312 for hanging medical fluid containers/bags 1330.

As stated, the adjustable strap 1326 is preferably hingedly connected to the mounting plate 1312, whereby the adjustable strap 1326 is movable between an engaged position directly contacting and located proximate to the medical fluid container 1316 to support the medical fluid container 1316 in lateral directions, and a disengaged position generally out of contact with the fluid container 1316. A tab member 1332 is connected to the mounting plate 1312 and cooperates with openings 1333 formed in the adjustable strap 1326 to allow the adjustable strap 1326 to receive and restrain different sized medical fluid containers 1316. The tab member 1332 may be secured to the mounting plate 1312 by mechanical methods (i.e., fasteners) or by adhesive. The mounting plate 1312, U-shaped bracket 1322, adjustable strap 1326, and hook members 1328 are preferably formed of plastic and, preferably, a medical grade plastic.

A retaining clip 1334 is located at the bottom edge of the mounting plate 1312 to restrain the fluid transfer tubing used in association with the medical fluid container 1316. The medical fluid container 1316 and medical fluid bag 1330 shown in FIGS. 13 and 14 may be placed in fluid communication with the syringe 20 or other medical container associated with the loader 610 by the fluid transfer set 1270, the details of which are discussed hereinafter. The retaining clip 1334 may be made of plastic and affixed to the mounting plate 1212 by mechanical methods (i.e., fasteners) or by an adhesive.

Figure 15:
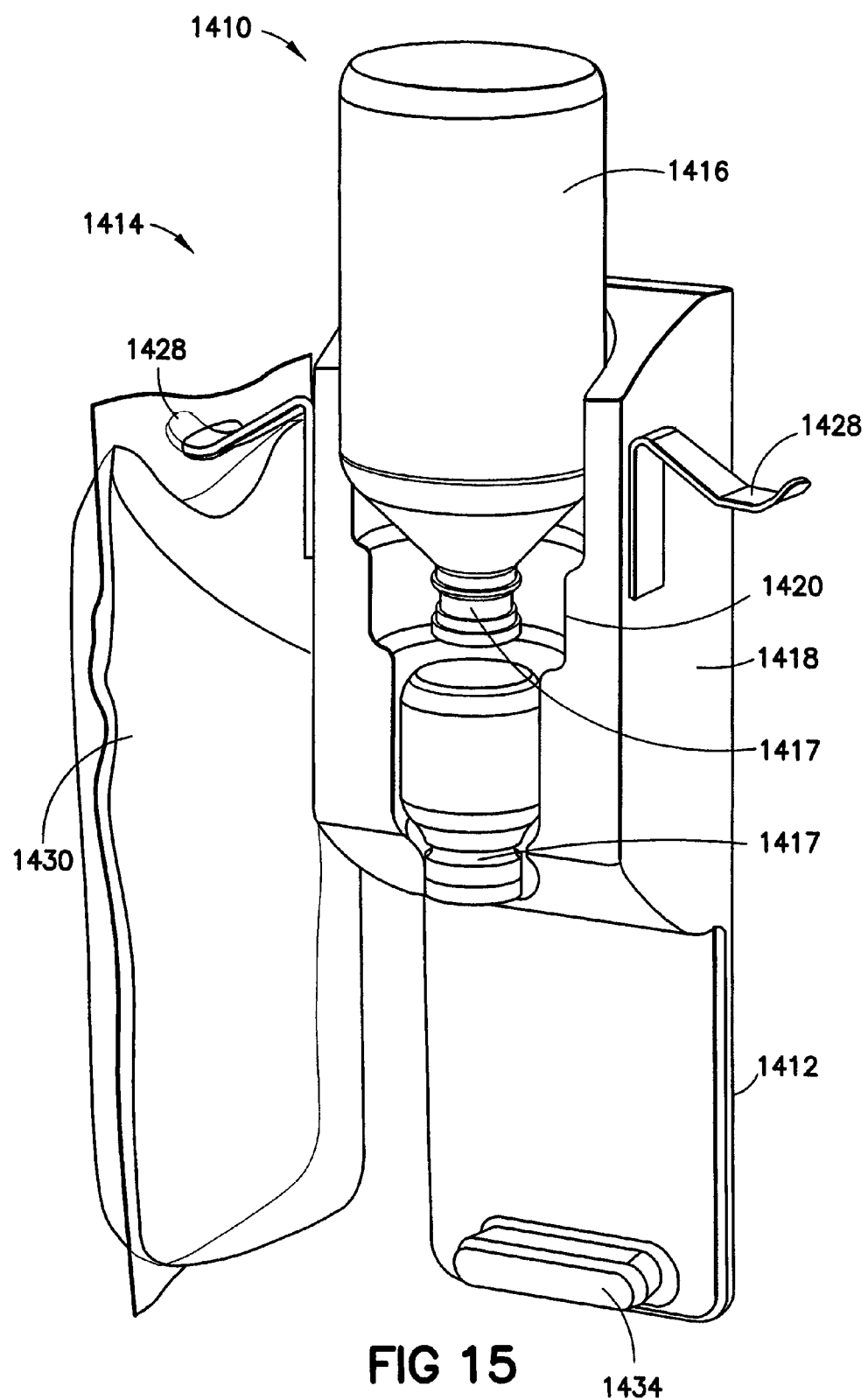
FIG. 15 is a perspective view of another embodiment of a fill station adapted for use in the syringe loading system of FIGS. 8 and 9.

Referring to FIGS. 15 and 16, an additional embodiment of a fill station 1410 adapted for use in connection with the loading system 1200 of FIGS. 8 and 9 is shown. The fill station 1410 includes a mounting plate 1412 and a holding assembly 1414 that supports a medical fluid container 1416. The holding assembly 1414 now includes a single fixed support 1418. In the fill station 1410 shown in FIGS. 15 and 16, the fixed support 1418 is substantially funnel-shaped and connected directly to the mounting plate 1412. The fixed support 1418 may also be formed integrally with the mounting plate 1412 or mounted to the mounting plate 1412 by conventional means (i.e., mechanical fasteners or adhesive). As shown in FIGS. 15 and 16, an inner wall 1420 of the funnel-shaped fixed support 1418 is stepped to accommodate different sized medical fluid containers 1416, each having, for example, different sized necks 1417. The stepped inner wall 1420 defines multiple ridges 1422 that cooperate with the shoulder and body 1421 of the medical fluid container 1416. Preferably, the stepped inner wall 1418 extends greater than 180° around the circumference of the medical fluid container 1416, which prevents the medical fluid container 1416 from displacing from the fixed support 1418 once loaded therein. As shown in FIG. 16, the stepped inner wall 1418 defines multiple pairs of opposing lips 1424, which prevent the different sized medical fluid containers 1416 from passing through a front opening 1426 in the fixed support 1418. The fixed support 1418 is preferably formed of plastic and, preferably, a medical grade plastic, and may be integrally formed of plastic with the mounting plate 1412.

The holding assembly 1414 further includes a pair of hook members 1428 that are used to support one or more medical fluid containers/bags 1430. The hook members 1428 may be connected to the sides of the fixed support 1418 by conventional means (i.e., mechanical fasteners or adhesive), or be formed integrally with the fixed support 1418. Preferably, the hook members 1428 are made of plastic. A retaining clip 1434, similar to the retaining clips 1266 and 1334 discussed previously, may be located at the bottom edge of the mounting plate 1412. Once again, the medical fluid container 1416 may be placed in fluid communication with the syringe 20 or other medical container used in the loader 610 by the fluid transfer set 1270 to be discussed herein in connection with FIGS. 20-26. The mounting plate 1412 may be made to extend behind the medical fluid bags 1430 supported by the hook members 1428.

Figure 17:
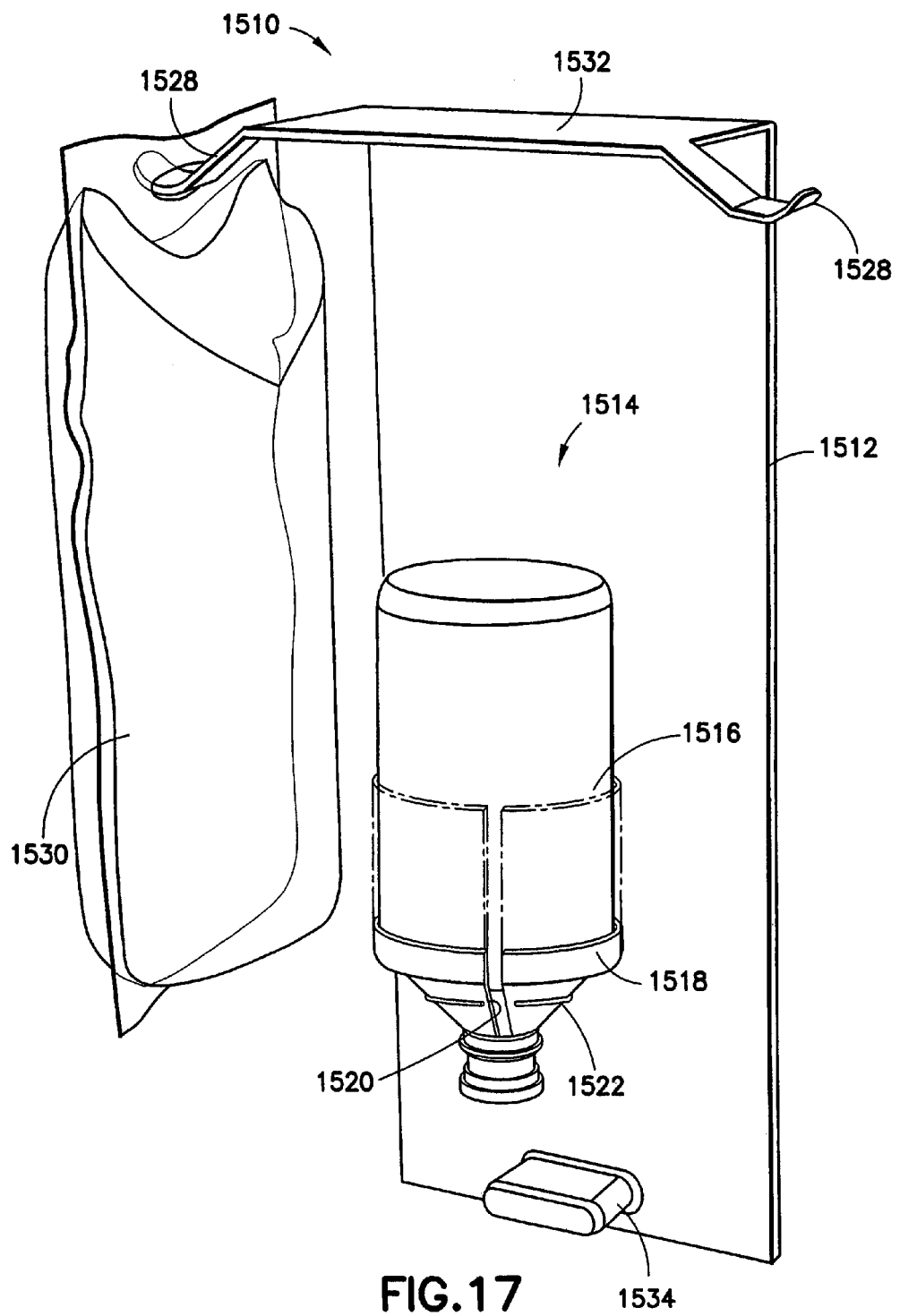
FIG. 17 is a perspective view of another embodiment of a fill station adapted for use in the syringe loading system of FIGS. 8 and 9.

FIG. 17 shows a further embodiment of a fill station 1510 adapted for use in the loading system 1200 of FIGS. 8 and 9. The fill station 1510 includes a mounting plate 1512 and a holding assembly 1514 that supports a medical fluid container 1516. The holding assembly 1514 is also comprised of a single fixed support 1518 in a similar manner to the holding assembly 1414 discussed in connection with FIGS. 15 and 16. In the fill station 1510 shown in FIG. 17, the fixed support 1518 is also substantially funnel-shaped and connected to the mounting plate 1512. The fixed support 1518 may be formed integrally with the mounting plate 1512 or mounted to the mounting plate 1512 by conventional means (i.e., mechanical fasteners or adhesive). The fixed support 1518 has a tapered inner wall 1520, which forms the funnel shape of the fixed support 1518. The funnel shape of the fixed support 1518 accommodates different sized medical fluid containers 1516 in a conventional manner. The fixed support 1518 of FIG. 17 is generally in the form of a traditional funnel with a smooth and tapered inner wall 1520 for cooperating with the tapered (i.e., shoulder) portion of the fluid container 1516 in a conventional manner. A sidewall 1522 of the fixed support 1518 is preferably split to allow fluid transfer tubing to be inserted therethrough. In FIG. 17, the fixed support 1518 is illustrated as accommodating only the tapered, shoulder portion of the fluid container 1516. However, the sidewall 1522 may be extended upward in the form of a cylinder, as shown in broken lines in FIG. 17, to accommodate the cylindrical portion of the body of the fluid container 1516 and provide increased support for the fluid container 1516. The fixed support 1518 is preferably formed of plastic and, preferably, a medical grade plastic.

The fill station 1510 further includes hook members 1528 that may be used to support medical fluid containers/bags 1530, and a shelf 1532. The shelf 1532 and hook members 1528 may be formed integrally, for example from plastic, with the mounting plate 1512 or formed separately from the mounting plate 1512 and then attached to the mounting plate 1512, for example by mechanical fasteners or adhesive. The shelf 1532 and hook members 1528 are located at the upper end of the mounting plate 1512. Preferably, the hook members 1528 are made of plastic. A retaining clip 1534, similar to the retaining clips 1266, 1334–1434, discussed previously, may be located at the bottom edge of the mounting plate 1512. The retaining clip 1534 may be made of plastic and affixed to the mounting plate 1512 by mechanical methods (i.e., fasteners) or by an adhesive. The medical fluid container 1516 is placed in fluid communication with the syringe 20 or other medical container used in the loader 610 by the fluid transfer set 1270 originally illustrated in FIGS. 8 and 9 and discussed herein in connection with FIGS. 20–26.

FIGS. 18 and 19 illustrate a still further embodiment of a fill station 1610 adapted for use in the loading system 1200 of FIGS. 8 and 9. The fill station 1610 includes a mounting plate 1612 and a holding assembly 1614 that supports a medical fluid container 1616. The holding assembly 1614 is also comprised of a single fixed support 1618. In the fill station 1610 shown in FIGS. 18 and 19, the fixed support 1618 is substantially rectangular shaped and connected (i.e., mounted) directly to the mounting plate 1612. The fixed support 1618 may be formed integrally with the mounting plate 1612 or mounted to the mounting plate 1612 by conventional means, for example, mechanical fasteners or adhesive. The fixed support 1618 and mounting plate 1612 are preferably made of plastic, and preferably a medical grade plastic. The fixed support 1618 has a tapered inner wall or inclined inner support 1620 against which the medical fluid container 1616 rests when placed in the fixed support 1618. Thus, in the fixed support 1618, the medical fluid container 1616 is generally seated at an angle with respect to vertical. A bottom wall 1622 of the fixed support 1618 defines a U-shaped opening 1624 for receiving the neck of the fluid container 1616. Sidewalls 1626 of the fixed support 1618 may taper inward toward the fluid container 1616 to provide additional support for the fluid container 1616.

The fill station 1610 further includes hook members 1628 that may be used to support medical fluid containers/bags 1630, and a shelf 1632. The shelf 1632 and hook members 1628 may be formed integrally with the mounting plate 1612 or formed separately from the mounting plate 1612 and then attached to the mounting plate 1612, for example, by mechanical fasteners or adhesive. Preferably, the hook members 1628 and shelf 1632 are formed of plastic and fixedly connected to the mounting plate 1612. The shelf 1632 and hook members 1628 are located at the upper end of the mounting plate 1612. A retaining clip 1634 may be located at the bottom edge of the mounting plate 1612. The retaining clip 1634 is formed slightly differently from the clips 1266 and 1334–1534 discussed previously and is now defined by a pair of spiral or coil members 1636. The retaining clip 1634 and, more preferably, the coil members 1636 are preferably made of plastic for resiliency. The medical fluid container 1616 is placed in fluid communication with the syringe 20 or other medical container used in the loader 610 by the fluid transfer set 1270 discussed herein.

Referring to FIGS. 20–26, the fluid transfer set 1270 used for connecting the syringe 20 or other medical container received in the loading device 610 to the medical fluid container 1216-1616 received in the respective fill stations 1210–1610 described hereinabove is illustrated. The fluid transfer set 1270 is generally comprised of a spike member 1700, a luer connection 1702, a fluid transfer tube 1704, and a valve 1706. The spike member 1700 has a distal end 1708 preferably formed to puncture the lid of the medical fluid container 1216–1616 and a proximal end 1710 configured to receive one end of the tube 1704. The tube 1704 is preferably adhesively secured within the proximal end 1710 of the spike member 1700 by a medical grade adhesive.

Figure 21:
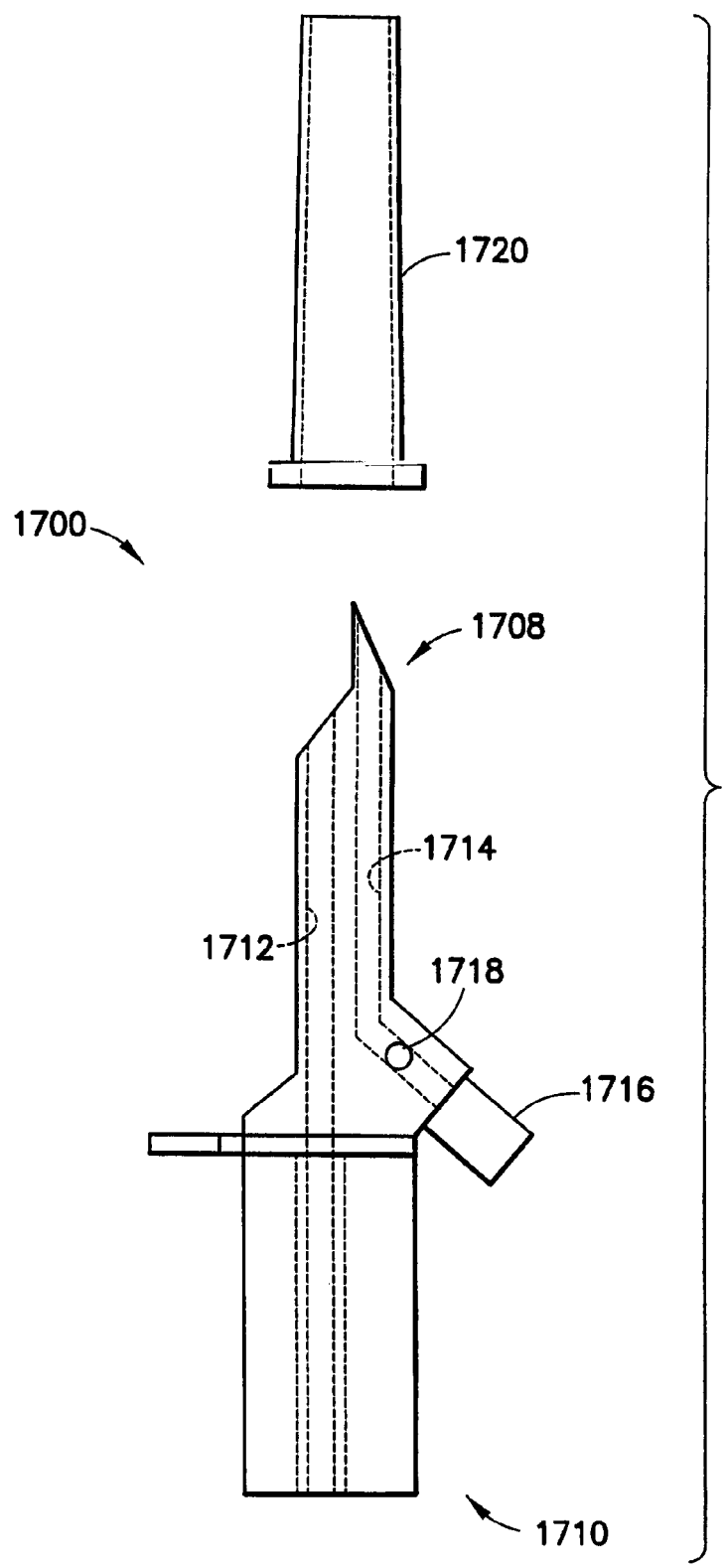
FIG. 21 is an exploded view of a spike member and tip guard of the fluid transfer set of FIG. 20 showing hidden lines.
Figure 22:
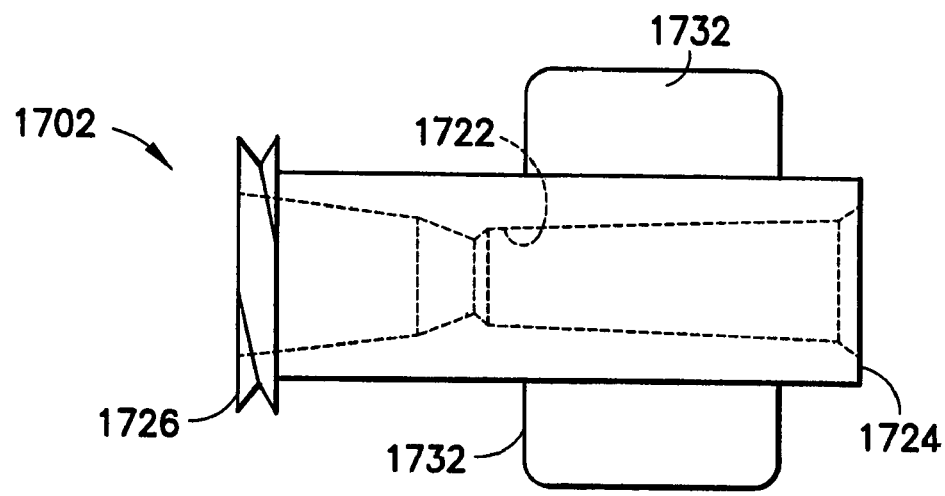
FIG. 22 is a plan view of a luer connection of the fluid transfer set of FIG. 20 showing hidden lines.
Figure 23:
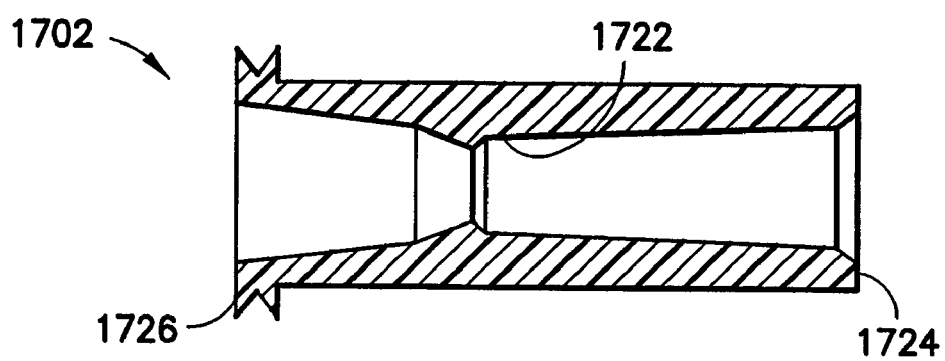
FIG. 23 is a cross sectional view of the luer connection of FIG. 22 taken along a longitudinal axis of the luer connection.
Figure 24:
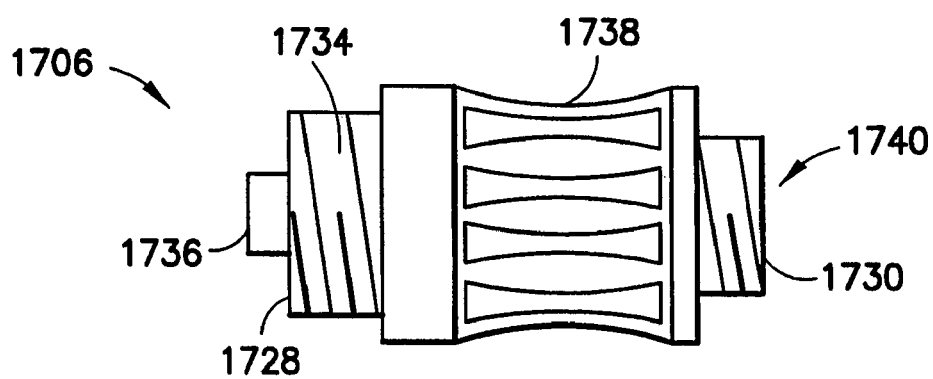
FIG. 24 is a side view of a valve of the fluid transfer set of FIG. 20.
Figure 25:
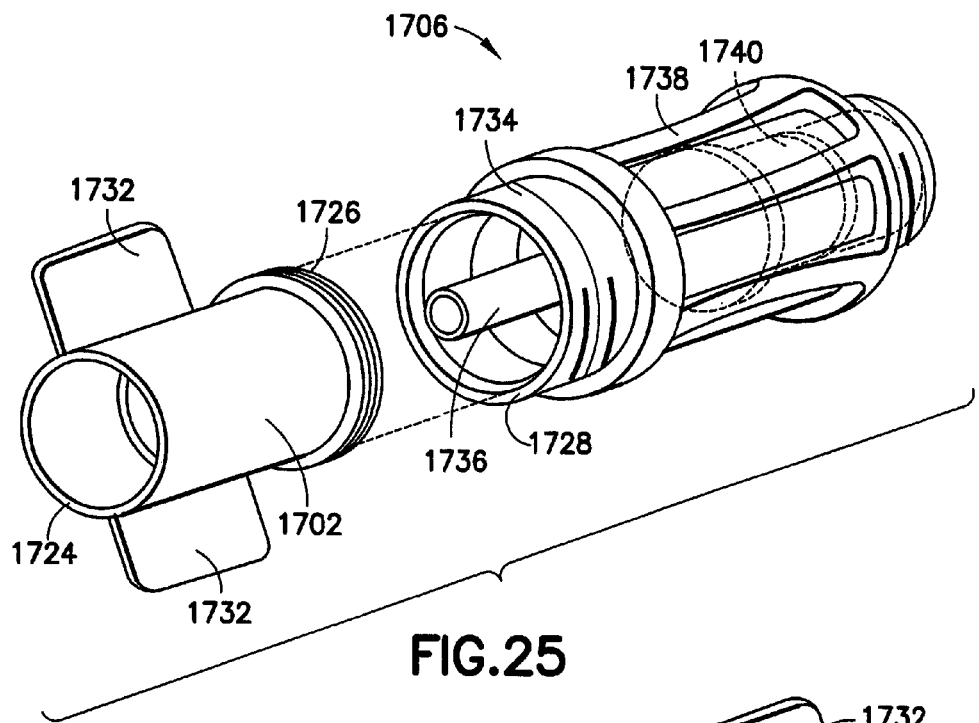
FIG. 25 in an exploded perspective view of the valve and luer connection shown in FIG. 20 viewed from one end of the valve-luer connection.
Figure 26:
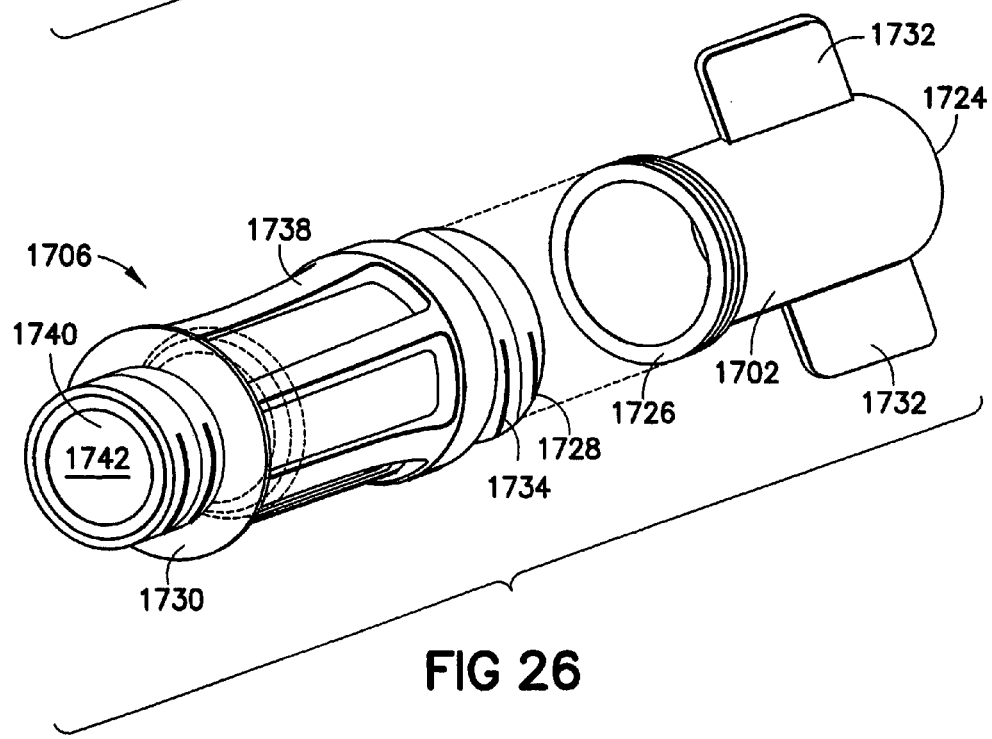
FIG. 26 is an exploded perspective view of the valve-luer connection shown in FIG. 20 viewed from the opposite end.

As shown in FIG. 21, the spike member 1700 defines a main conduit 1712 extending longitudinally therethrough, which is used to transfer fluid from the medical fluid container 1216–1616 to the tube 1704. The spike member 1700 further defines a branch conduit 1714, which has a filter cap assembly 1716 at one end. A stainless steel ball 1718 is located within the branch conduit 1714. The branch conduit 1714 provides a passage for air to flow into the medical fluid container 1216–1616, thereby allowing a user of the fluid transfer set 1270 to remove fluid from the medical fluid container 1216–1616 through the main conduit 1712. A tip guard 1720 may be used to enclose the sharpened distal end 1708 of the spike member 1700. The tip guard 1720 cooperates with the body of the spike member 1700 to enclose the sharpened distal end 1708 of the spike member 1700.

The luer connection 1702 is preferably a female luer connection that defines a central opening 1722 extending therethrough. The luer connection 1702 comprises a first end 1724, which connects to the tube 1704, and a second end 1726 that connects to the valve 1706. In particular, the tube 1704 is received in the first end 1724 and secured therein, preferably by a medical grade adhesive. The second end 1726 is preferably externally threaded to mate with a first end 1728 of the valve 1706. The valve 1706 further includes a second end 1730 adapted to cooperate with the syringe 20 or other medical container used in the loader 610, as discussed herein. The luer connection 1702 is preferably made of a hard plastic, such as polycarbonate, which is preferably clear to allow viewing of liquid within the body of the luer connection 1702. The luer connection 1702 may be formed with a pair of wings 1732 to facilitate grasping by the user of the fluid transfer set 1240. In lieu of the two-piece construction of the luer connection 1702 and valve 1706, the luer connection 1702 and valve 1706 may be integrally formed of plastic, such as polycarbonate.

As stated, the valve 1706 is preferably connected to the luer connection 1702 by a threaded connection. For this purpose, the first end 1728 of the valve 1706 may comprise an internally threaded portion 1734, which cooperates with the externally threaded second end 1726 of the luer connection 1702. The first end 1728 of the valve 1706 may include a tubular projection 1736, which projects into the central opening 1722 in the luer connection 1702 to facilitate fluid flow between the luer connection 1702 and valve 1706. The second end 1730 of the valve 1706 is preferably configured for a threaded connection to the syringe 20 or other medical container used in the loader 610. For this purpose, the second end 1730 is preferably internally threaded to cooperate with external threads (not shown, but known in the art) formed on the tip 26 of the syringe 20 or other medical container. Thus, the valve 1706 is connected to the syringe 20 by a threaded connection, but any equivalent mechanical connection may be used between the valve 1706 and the syringe 20 or other medical container.

The valve 1706 includes a tubular housing 1738 and an internal closure member 1740, which biases the valve 1706 to a closed position. The valve 1706 accordingly operates substantially as a shut-off or stopper valve. In alternative embodiments, however, a check-valve may be suitable for use with the fluid transfer set 1700. The tubular housing 1738 is preferably made from a hard plastic, such as polycarbonate. The first end 1728 of the valve 1706/housing 1738 defines an internally threaded portion 1734 for receiving the externally threaded second end 1726 of the luer connection 1702. The second end 1730 of the valve 1706/housing 1738 is internally threaded for cooperating with the tip 26 of the syringe 20 or other medical container. Preferably, the tip 26 of the syringe 20 or other medical container defines external threads (not shown) for cooperating with the second end 1730 of the housing 1738.

The internal closure member 1740 is a soft and pliable member that is displaced by the tip 26 of the syringe 20 or other medical container when the syringe 20 or other medical container is mated with the housing 1738. The internal closure member 1740 is displaced sufficiently to permit fluid flow through the valve 1706 and to the syringe 20 or other medical container. The internal closure member 1740 has a substantially planar exposed end 1742, which is recessed within the second end 1730 of the housing 1738. The recessed configuration of the exposed end 1742 in the second end 1730 of the housing 1738 provides an easily cleaned and sterilized body for connection to the syringe 20 or other medical container. A Q-tip® swab or other similar cleaning implement may be used to clean and sterilize the exposed end 1742 of the internal closure member 1740 and the second end 1730 of the housing 1738. While the exposed end 1742 of the internal closure member 1740 is preferably recessed within the housing 1738, the exposed end 1742 may also be formed to lie substantially flush with the end of the second end 1730 of the housing 1738. A potentially suitable valve 1706 is disclosed and described in U.S. Pat. No. 6,471,674, the contents of which are incorporated herein by reference.

Referring to FIGS. 8–20, the fluid transfer set 1240 is used to connect the medical fluid container 1216–1616 held within the holding assembly 1214–1614 of the fill station(s) 1210–1610 to, for example, a hand-held syringe, a syringe mounted on a medical injector or the syringe 20 located in the loader 610. In operation, the user of the loading system 1200 generally first connects the valve 1706 to the tip 26 of the syringe 20 or other medical container loaded to the loader 610. The threaded engagement between the valve 1706 and the tip 26 of the syringe 20 or other medical container opens the internal closure member 1740 within the valve 1706, allowing fluid to flow through the valve 1706. The user of the fluid transfer set 1240 may then remove the tip guard 1720 from the spike member 1700. The spike member 1700 is then used to puncture the medical fluid container 1216–1616 held within the holding assembly 1214–1614 of the fill station(s) 1210–1610. Fluid from the medical fluid container 1216–1616 may now flow from the medical fluid container 1216–1616 to the syringe 20 or other medical container. The syringe 20 or other medical container is then loaded with fluid in the manner discussed previously. Once the syringe 20 or other medical container is loaded, the valve 1706 may be disengaged from the tip 26 of the syringe 20 or other medical container. The valve 1706 is normally bias to a closed position by the internal closure member 1740, which closes the valve 1706 automatically once the housing 1738 is unthreaded from the syringe 20 or other medical container. The valve 1706 operates as a "stopper valve". The syringe 20 or other medical container may then be removed from the loader 610 and used in an injection procedure as discussed previously.

The foregoing description and accompanying drawings set forth the preferred embodiments of the invention at the present time. Various modifications, additions and alternative designs will, of course, become apparent to those skilled in the art in light of the foregoing teachings without departing from the scope of the disclosed invention. The scope of the invention is indicated by the following claims rather than by the foregoing description. All changes and variations that come within the meaning and range of equivalency of the claims are to be embraced within their scope.

What is claimed is:

1. A fill station comprising:
   a mounting plate; and
   a holding assembly connected to the mounting plate for supporting a medical fluid container, the holding assembly comprising a fixed support and a movable support, the movable support movable between an engaged position supporting the body of the at least one medical fluid container for maintaining the medical fluid container in the holding assembly and a disengaged position out of contact with the body of the medical fluid container,
   wherein at least a portion of the moveable support is disposed within the fixed support.

2. The fill station of claim 1, further comprising a hook member connected to the mounting plate for supporting a medical fluid bag.

3. The fill station of claim 1, wherein the mounting plate is configured to be wall-mounted.

4. The fill station of claim 1, further comprising a shelf connected to the mounting plate.

5. The fill station of claim 4, further comprising a hook member connected to the shelf for supporting a medical fluid bag.

6. The fill station of claim 1, further comprising a clip connected to the mounting plate and configured to receive and restrain fluid transfer tubing used with the medical fluid container.

7. The fill station of claim 1, the fixed support comprising a U-shaped bracket connected to the mounting plate for receiving a neck of the medical fluid container.

8. The fill station of claim 1, the fixed support further comprising a pair of support arms connected to the mounting plate, wherein the movable support and the support arms, in combination, are adapted to maintain the medical fluid container in the holding assembly.

9. The fill station of claim 1, wherein the movable support comprises an adjustable strap.

10. A fill station comprising:
    a mounting plate;
    a holding assembly connected to the mounting plate for supporting a medical fluid container, the holding assembly comprising a substantially funnel-shaped fixed support connected to the mounting plate for receiving and supporting the medical fluid container; and
    a hook member connected to one of the mounting plate for supporting a medical fluid bag or the fixed support for supporting a medical fluid bag.

11. The fill station of claim 10, wherein the mounting plate is configured to be wall-mounted.

12. The fill station of claim 10, further comprising a shelf connected to the mounting plate.

13. The fill station of claim 12, further comprising a hook member connected to the shelf for supporting a medical fluid bag.

14. The fill station of claim 10, further comprising a clip connected to the mounting plate and configured to receive and restrain fluid transfer tubing used with the medical fluid container.

15. The fill station of claim 10, wherein the mounting plate and fixed support are formed integrally from plastic.

16. The fill station of claim 10, wherein the fixed support comprises a split sidewall for passing fluid transfer tubing therethrough.

17. A fill station comprising:
    a mounting plate; and
    a holding assembly connected to the mounting plate for supporting a medical fluid container, the holding assembly comprising a substantially funnel-shaped fixed support connected to the mounting plate for receiving and supporting the medical fluid container,
    wherein an inner wall of the fixed support is stepped to accommodate different sized medical fluid containers.

18. A fill station comprising:
    a mounting plate; and
    a holding assembly connected to the mounting plate for supporting a medical fluid container, the holding assembly comprising a substantially rectangular shaped fixed support connected to the mounting plate for receiving and supporting the medical fluid container, the fixed support comprising an inclined inner support for supporting the body of the medical fluid container.

19. The fill station of claim 18, further comprising a hook member connected to the mounting plate for supporting a medical fluid bag.

20. The fill station of claim 18, wherein the mounting plate is configured to be wall-mounted.

21. The fill station of claim 18, further comprising a shelf connected to the mounting plate.

22. The fill station of claim 18, further comprising a clip connected to the mounting plate and configured to receive and restrain fluid transfer tubing used with the medical fluid container.

23. The fill station of claim 18, wherein the mounting plate and the fixed support are formed integrally from plastic.

24. A fill station comprising:
    a mounting plate; and
    a holding assembly connected to the mounting plate for supporting a medical fluid container, the holding assembly comprising a fixed support and a movable support, the movable support adapted to engage the body of the medical fluid container to maintain the medical fluid container in the holding assembly, wherein the fixed support and the movable support are each mounted to a base plate connected to the mounting plate.

25. The fill station of claim 24, wherein the movable support comprises a resiliently biased support arm.

26. The fill station of claim 25, wherein the support arm defines a central recess formed to cooperate with the body of the medical fluid container.

27. The fill station of claim 25, wherein the support arm is supported on a pivot pin and resiliently biased by torsion springs.

28. The fill station of claim 24, wherein the fixed support comprises a pair of support arms connected to the base plate, and wherein the movable support and the support arms, in combination, are adapted to maintain the medical fluid container in the holding assembly.

29. The fill station of claim 28, wherein the support arms define apertures for viewing contents of the medical fluid container.

30. The fill station of claim 24, wherein the support arms curve inward and further comprise integral support legs for supporting the body of the medical fluid container.

31. The fill station of claim 24, further comprising a hook assembly connected to the mounting plate, the hook assembly comprising a hook member mounted to a support base connected to the mounting plate.

32. The fill station of claim 24, further comprising a clip connected to the mounting plate and configured to receive and restrain fluid transfer tubing used with the medical fluid container.

33. The fill station of claim 24, wherein the mounting plate is configured to be wall-mounted.

34. A fill station comprising:
a mounting plate;
a holding assembly connected to the mounting plate for supporting a medical fluid container, the holding assembly comprising a fixed support and a movable support, the movable support movable between an engaged position supporting the body of the at least one medical fluid container for maintaining the medical fluid container in the holding assembly and a disengaged position out of contact with the body of the medical fluid container; and
a hook member connected to the mounting plate for supporting a medical fluid bag.

35. A fill station comprising:
a mounting plate;
a holding assembly connected to the mounting plate for supporting a medical fluid container, the holding assembly comprising a fixed support and a movable support, the movable support movable between an engaged position supporting the body of the at least one medical fluid container for maintaining the medical fluid container in the holding assembly and a disengaged position out of contact with the body of the medical fluid container; and
a clip connected to the mounting plate and configured to receive and restrain fluid transfer tubing used with the medical fluid container.

\* \* \* \* \*